(12) United States Patent
Pavlovskaia et al.

(10) Patent No.: US 10,675,063 B2
(45) Date of Patent: *Jun. 9, 2020

(54) SYSTEM AND METHOD FOR IMAGE SEGMENTATION IN GENERATING COMPUTER MODELS OF A JOINT TO UNDERGO ARTHROPLASTY

(71) Applicant: Howmedica Osteonics Corporation, Mahwah, NJ (US)

(72) Inventors: Elena Pavlovskaia, San Francisco, CA (US); Oleg Mishin, Foster City, CA (US); Boris E. Shpungin, Pleasanton, CA (US)

(73) Assignee: HOWMEDICA OSTEONICS CORPORATION, Mahwah, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/229,997

(22) Filed: Dec. 21, 2018

(65) Prior Publication Data
US 2019/0117268 A1 Apr. 25, 2019

Related U.S. Application Data

(63) Continuation of application No. 15/581,974, filed on Apr. 28, 2017, now Pat. No. 10,159,513, which is a
(Continued)

(51) Int. Cl.
G06K 9/00 (2006.01)
A61B 17/70 (2006.01)
(Continued)

(52) U.S. Cl.
CPC .......... A61B 17/7013 (2013.01); A61B 5/055 (2013.01); A61B 6/032 (2013.01);
(Continued)

(58) Field of Classification Search
USPC ........................................................ 382/131
See application file for complete search history.

(56) References Cited

U.S. PATENT DOCUMENTS 5,568,384 A 10/1996 Robb et al.
5,587,912 A 12/1996 Andersson et al.
(Continued)

FOREIGN PATENT DOCUMENTS

EP 2280671 A1 2/2011
WO WO 03/107275 A2 12/2003
WO WO 2009/019617 A2 2/2009

OTHER PUBLICATIONS

Seim H et al. "Segmentation of Bony structures with Ligament Attachment Sites." Springer, Apr. 6, 2008, pp. 207-211.
(Continued)

Primary Examiner — Rodney E Fuller
(74) Attorney, Agent, or Firm — Polsinelli PC

(57) ABSTRACT

A custom arthroplasty guide and a method of manufacturing such a guide are disclosed herein. The method of manufacturing the custom arthroplasty guide includes: a) generating medical imaging slices of the portion of the patient bone; b) identifying landmarks on bone boundaries in the medical imaging slices; c) providing model data including image data associated with a bone other than the patient bone; d) adjusting the model data to match the landmarks; e) using the adjusted model data to generate a three dimensional computer model of the portion of the patient bone; f) using the three dimensional computer model to generate design data associated with the custom arthroplasty guide; and g) using the design data in manufacturing the custom arthroplasty guide.

20 Claims, 75 Drawing Sheets

Related U.S. Application Data continuation of application No. 14/946,106, filed on Nov. 19, 2015, now Pat. No. 9,687,259, which is a continuation of application No. 13/731,697, filed on Dec. 31, 2012, now Pat. No. 9,208,263, which is a continuation of application No. 13/374,960, filed on Jan. 25, 2012, now Pat. No. 8,532,361, which is a continuation of application No. 13/066,568, filed on Apr. 18, 2011, now Pat. No. 8,160,345, which is a continuation-in-part of application No. 12/386,105, filed on Apr. 14, 2009, now Pat. No. 8,311,306.

(60) Provisional application No. 61/126,102, filed on Apr. 30, 2008.

(51) Int. Cl.

| | | |
|---|---|---|
| *B33Y 50/00* | (2015.01) | |
| *B33Y 80/00* | (2015.01) | |
| *G06T 7/12* | (2017.01) | |
| *G06T 7/13* | (2017.01) | |
| *G06K 9/48* | (2006.01) | |
| *G06T 17/00* | (2006.01) | |
| *G06F 30/00* | (2020.01) | |
| *G06F 30/20* | (2020.01) | |
| *A61B 5/055* | (2006.01) | |
| *A61B 6/03* | (2006.01) | |
| *A61B 17/16* | (2006.01) | |
| *A61B 17/17* | (2006.01) | |
| *G06K 9/20* | (2006.01) | |
| *G06T 17/20* | (2006.01) | |
| *A61B 34/10* | (2016.01) | |
| *B33Y 10/00* | (2015.01) | |
| *B33Y 50/02* | (2015.01) | |
| *A61B 90/00* | (2016.01) | |
| *G16H 50/50* | (2018.01) | |
| *G06T 7/00* | (2017.01) | |
| *G06F 19/00* | (2018.01) | |
| *A61B 17/15* | (2006.01) | |
| *G06T 7/70* | (2017.01) | |

(52) U.S. Cl.
CPC ...... *A61B 17/1675* (2013.01); *A61B 17/1703* (2013.01); *A61B 34/10* (2016.02); *A61B 90/37* (2016.02); *B33Y 10/00* (2014.12); *B33Y 50/00* (2014.12); *B33Y 50/02* (2014.12); *B33Y 80/00* (2014.12); *G06F 19/00* (2013.01); *G06F 30/00* (2020.01); *G06F 30/20* (2020.01); *G06K 9/2063* (2013.01); *G06K 9/48* (2013.01); *G06T 7/0012* (2013.01); *G06T 7/12* (2017.01); *G06T 7/13* (2017.01); *G06T 17/00* (2013.01); *G06T 17/20* (2013.01); *G16H 50/50* (2018.01); *A61B 17/155* (2013.01); *A61B 17/157* (2013.01); *A61B 2017/1602* (2013.01); *A61B 2034/105* (2016.02); *A61B 2034/107* (2016.02); *A61B 2034/108* (2016.02); *A61B 2090/374* (2016.02); *A61B 2090/3762* (2016.02); *G06K 2009/484* (2013.01); *G06K 2209/055* (2013.01); *G06T 7/70* (2017.01); *G06T 2200/08* (2013.01); *G06T 2207/30008* (2013.01); *Y10T 29/49826* (2015.01)

(56) References Cited

U.S. PATENT DOCUMENTS

| | | |
|---|---|---|
| 5,768,413 A | 6/1998 | Levin et al. |
| 5,880,962 A | 3/1999 | Andersson et al. |
| 5,970,182 A | 10/1999 | Goris |
| 6,345,112 B1 | 2/2002 | Summers et al. |
| 6,556,696 B1 | 4/2003 | Summers et al. |
| 6,771,262 B2 | 8/2004 | Krishnan |
| 6,813,373 B1 | 11/2004 | Suri et al. |
| 7,024,027 B1 | 4/2006 | Suri et al. |
| 7,149,564 B2 | 12/2006 | Vining et al. |
| 7,457,444 B2 | 11/2008 | Geiger et al. |
| 7,630,550 B2 | 12/2009 | Maroy et al. |
| 7,653,229 B2 | 1/2010 | Kaufhold et al. |
| 7,822,244 B2 | 10/2010 | Blumhofer |
| 7,831,078 B2 | 11/2010 | Unal et al. |
| 7,837,621 B2 | 11/2010 | Krause et al. |
| 7,853,310 B2 | 12/2010 | Vining et al. |
| 7,873,403 B2 | 1/2011 | Lachner et al. |
| 7,894,647 B2 | 2/2011 | Zhou et al. |
| 7,952,595 B2 | 5/2011 | Schiwietz et al. |
| 8,050,473 B2 | 11/2011 | Udupa et al. |
| 8,055,046 B2 | 11/2011 | Feilkas et al. |
| 8,073,216 B2 | 12/2011 | Dawant et al. |
| 8,078,440 B2 | 12/2011 | Otto |
| 8,098,909 B2 | 1/2012 | Hibbard et al. |
| 8,131,038 B2 | 3/2012 | Saddi et al. |
| 8,135,186 B2 | 3/2012 | Bouman et al. |
| 8,140,144 B2 | 3/2012 | Dale et al. |
| 8,160,325 B2 | 4/2012 | Zug et al. |
| 8,160,326 B2 | 4/2012 | Zug et al. |
| 8,160,345 B2 * | 4/2012 | Pavlovskaia ............ G06F 19/00 382/131 |
| 8,275,446 B2 | 9/2012 | Vining et al. |
| 8,289,317 B2 | 10/2012 | Harvill |
| 8,311,306 B2 * | 11/2012 | Pavlovskaia ............ G06K 9/32 382/131 |
| 8,355,553 B2 | 1/2013 | Fidrich et al. |
| 8,379,957 B2 | 2/2013 | Slabaugh et al. |
| 8,384,716 B2 | 2/2013 | Young et al. |
| 8,463,007 B2 | 6/2013 | Steinberg et al. |
| 8,532,361 B2 * | 9/2013 | Pavlovskaia ............ G06F 19/00 382/131 |
| 8,577,107 B2 | 11/2013 | Hibbard et al. |
| 8,698,795 B2 | 4/2014 | Grewer et al. |
| 8,724,881 B2 | 5/2014 | Zheng et al. |
| 8,731,258 B2 | 5/2014 | Hibbard et al. |
| 8,929,621 B2 | 1/2015 | Lathuiliere et al. |
| 8,948,472 B2 | 2/2015 | Wohlgemuth et al. |
| 9,208,263 B2 * | 12/2015 | Pavlovskaia ............ G06F 19/00 |
| 9,214,028 B2 | 12/2015 | Feilkas et al. |
| 9,289,153 B2 | 3/2016 | Lang |
| 9,292,933 B2 | 3/2016 | Madabhushi et al. |
| 9,387,079 B2 | 7/2016 | Bojarski et al. |
| 9,603,711 B2 * | 3/2017 | Bojarski ............... A61B 17/155 |
| 9,675,461 B2 | 6/2017 | Mahfouz |
| 9,687,259 B2 * | 6/2017 | Pavlovskaia ............ G06F 19/00 |
| 10,159,513 B2 * | 12/2018 | Pavlovskaia ............ G06F 19/00 |
| 2007/0198022 A1 * | 8/2007 | Lang ..................... A61B 17/154 606/88 |
| 2008/0243127 A1 * | 10/2008 | Lang ..................... A61B 5/4528 606/87 |
| 2008/0269596 A1 | 10/2008 | Revie et al. |
| 2009/0222014 A1 * | 9/2009 | Bojarski ............... A61B 17/155 606/88 |
| 2012/0041446 A1 * | 2/2012 | Wong ................. A61B 17/1703 606/96 |
| 2019/0239926 A1 | 8/2019 | Pavlovskaia et al. |
| 2019/0388123 A1 | 12/2019 | Pavlovskaia et al. |

OTHER PUBLICATIONS

European Search Report, EP17191709.9, dated Apr. 26, 2018.
Final Office Action, U.S. Appl. No. 14/776,660, dated Jun. 6, 2019.
Indian Examination Report, 3929/KOLNP/2010, dated Apr. 18, 2018.
Non-Final Office Action, U.S. Appl. No. 14/776,660, dated Oct. 26, 2018.
Non-Final Office Action, U.S. Appl. No. 16/376,362, dated Oct. 24, 2019.
Notice of Allowance, U.S. Appl. No. 16/522,281, dated Oct. 24, 2019.

(56) References Cited

OTHER PUBLICATIONS

Response to Final Office Action, U.S. Appl. No. 14/776,660, filed Dec. 6, 2019.
Response to Non-Final Office Action, U.S. Appl. No. 14/776,660, dated Feb. 27, 2019.

* cited by examiner

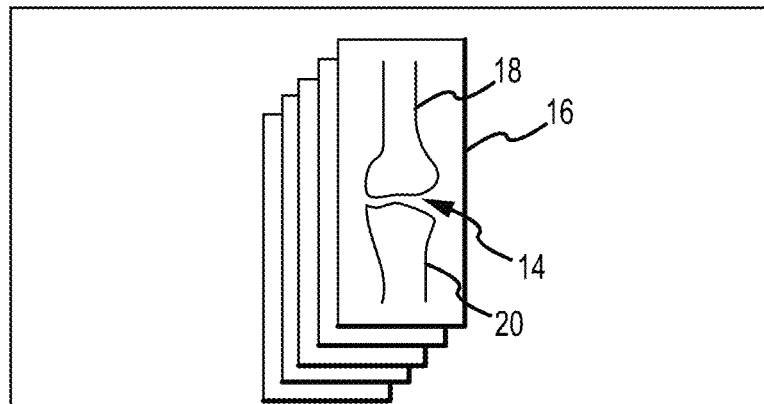
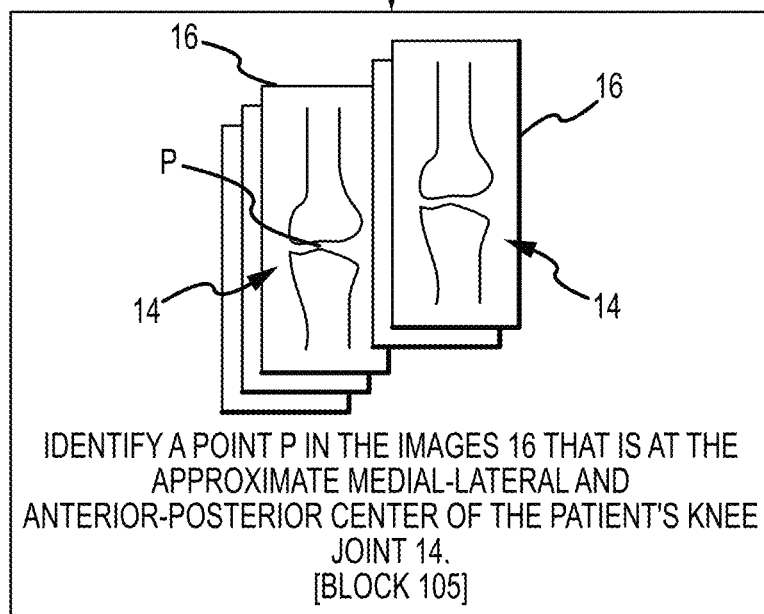
FIG.1B

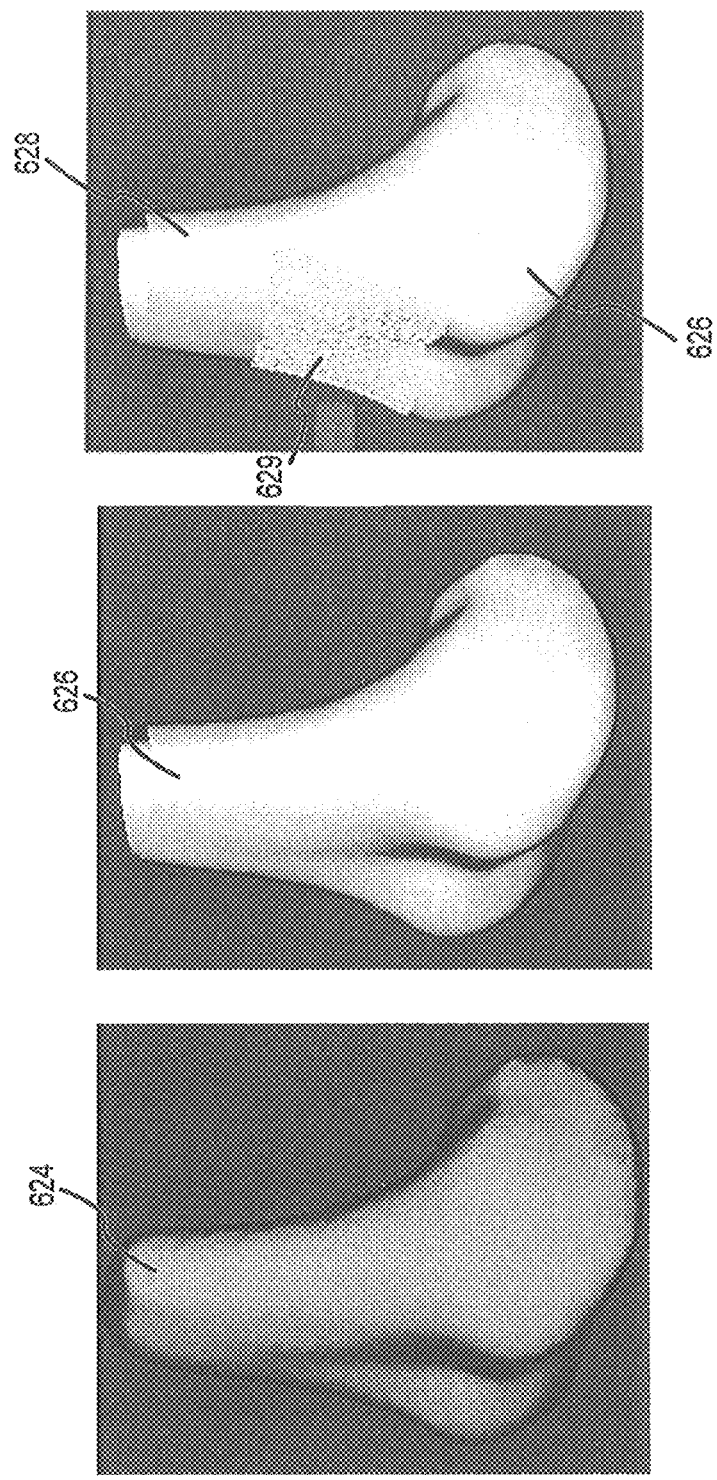

SYSTEM AND METHOD FOR IMAGE SEGMENTATION IN GENERATING COMPUTER MODELS OF A JOINT TO UNDERGO ARTHROPLASTY

CROSS REFERENCE TO RELATED APPLICATION

The present application is a continuation application of U.S. application Ser. No. 15/581,974 filed Apr. 28, 2017, which application is a continuation of U.S. application Ser. No. 14/946,106 filed Nov. 19, 2015, now U.S. Pat. No. 9,687,259, which application is a continuation of U.S. application Ser. No. 13/731,697 filed Dec. 31, 2012, now U.S. Pat. No. 9,208,263, which application is a continuation of U.S. application Ser. No. 13/374,960 filed Jan. 25, 2012, now U.S. Pat. No. 8,532,361, which application is a continuation of U.S. patent application Ser. No. 13/066,568, filed Apr. 18, 2011, now U.S. Pat. No. 8,160,345, which application is a continuation-in-part application of U.S. patent application Ser. No. 12/386,105 filed Apr. 14, 2009, now U.S. Pat. No. 8,311,306. U.S. application Ser. No. 12/386,105 claims the benefit under 35 U.S.C. § 119(e) of U.S. Provisional Patent Application No. 61/126,102, entitled "System and Method For Image Segmentation in Generating Computer Models of a Joint to Undergo Arthroplasty" filed on Apr. 30, 2008. Each of these applications is hereby incorporated by reference herein in their entireties.

FIELD OF THE INVENTION

The present invention relates to image segmentation. More specifically, the present invention relates to image segmentation in generating computer models of a joint to undergo arthroplasty, wherein the computer models may be used in the design and manufacture of arthroplasty jigs.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. Cartilage wearing down can result in fluid accumulating in the joint areas, pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on a human to "eyeball" bone models on a computer screen to determine configurations needed for the generation of the customized jigs. This "eyeballing" or manual manipulation of the bone modes on the computer screen is inefficient and unnecessarily raises the time, manpower and costs associated with producing the customized arthroplasty jigs. Furthermore, a less manual approach may improve the accuracy of the resulting jigs.

There is a need in the art for a system and method for reducing the labor associated with generating customized arthroplasty jigs. There is also a need in the art for a system and method for increasing the accuracy of customized arthroplasty jigs.

SUMMARY

Systems and methods for image segmentation in generating computer models of a joint to undergo arthroplasty are disclosed. Some embodiments may include a method of partitioning an image of a bone into a plurality of regions, where the method of partitioning may include obtaining a plurality of volumetric image slices of the bone, generating a plurality of spline curves associated with the bone, verifying that at least one of the plurality of spline curves follow a surface of the bone, and creating a three dimensional (3D) mesh representation based upon the at least one of the plurality of spline curves.

Other embodiments may include a method of generating a representation of a model bone, where the method of generating the representation may include obtaining an image scan of the representation as a plurality of slices, segmenting each slice in the plurality into one or more segmentation curves, generating a mesh of the representation, adjusting each slice in the plurality to include areas where the contact area of the bone is stable between successive image scans, and generating anchor segmentation such that the anchor segmentation follows a boundary of the representation of the model bone.

Other embodiments may include a method of segmenting a target bone using a representation of a model bone, where the method of segmenting the target bone may include registering a segmented form of the representation to an image scan of the target bone, refining the registration of the segmented form of the representation near a boundary of the target bone, generating a mesh from the segmented form of the representation, and generating a plurality of spline curves that approximate the intersection of the mesh and one or more slices from the image scan of the target bone.

Other embodiments may include a method of mapping a representation of a model bone into an image scan of a target bone, where the method of mapping may include registering a generated portion of the representation into the image scan of the target bone using a translational transformation, registering the generated portion of the representation into the image scan of the target bone using a similarity transformation, registering a boundary portion of the representation into the image scan of the target bone using an affine transformation, and registering the boundary portion of the representation into the image scan of the target bone using a spline transformation.

Other embodiments may include a method for determining a degree of correspondence between an image of a target bone and a representation of a model bone, where the method of determining correspondence may include selecting a plurality of sample points in the representation of the model bone to be registered, partitioning the plurality of sample points into a plurality of groups, sampling the image of the target bone, determining a correlation of voxel intensities between the image of the target bone and the representation of the model bone for each group in the plurality, and averaging the correlation determined for each group in the plurality.

Other embodiments may include a method for refining registration of a representation of a model bone to a target bone, where the method of refining may include transforming an anchor segmentation mesh, generating a plurality of random points around the transformed anchor segmentation mesh, determining if each point in the plurality lies inside one or more of the following meshes: InDark-OutLight, InLight-OutDark, or Dark-In-Light, determining whether one or more of the plurality of points lie within a threshold distance of the surface of the transformed anchor segmentation mesh, and adding each point in the plurality as a dark point or light point depending upon whether the point lies within the InDark-OutLight, InLight-OutDark, or Dark-In-Light meshes.

Still other embodiments may include a method for generating spline curves outlining the surface of a feature of interest of a target bone, where the method of generating spline curves may include intersecting a 3D mesh model of the feature surface with one or more slices of target data (the intersection defining a polyline curve), parameterizing the polyline curve as a function of length and tangent variation, calculating a weighted sum of the length and tangent parameterizations, and sampling the polyline using the results of the act of calculating.

A custom arthroplasty guide and a method of manufacturing such a guide are disclosed herein. The guide manufactured includes a mating region configured to matingly receive a portion of a patient bone associated with an arthroplasty procedure for which the custom arthroplasty guide is to be employed. The mating region includes a surface contour that is generally a negative of a surface contour of the portion of the patient bone. The surface contour of the mating region is configured to mate with the surface contour of the portion of the patient bone in a generally matching or interdigitating manner when the portion of the patient bone is matingly received by the mating region. The method of manufacturing the custom arthroplasty guide includes: a) generating medical imaging slices of the portion of the patient bone; b) identifying landmarks on bone boundaries in the medical imaging slices; c) providing model data including image data associated with a bone other than the patient bone; d) adjusting the model data to match the landmarks; e) using the adjusted model data to generate a three dimensional computer model of the portion of the patient bone; f) using the three dimensional computer model to generate design data associated with the custom arthroplasty guide; and g) using the design data in manufacturing the custom arthroplasty guide.

In one embodiment of the method of manufacturing the custom arthroplasty guide, operation a) includes generating at least one of MRI slices or CT slices of the portion of the patient bone.

In one embodiment of the method of manufacturing the custom arthroplasty guide, operation b) includes placing landmark points on the bone boundaries in the medical imaging slices. For example, placing the landmark points may include a user at a user interface employing at least one of a mouse, keyboard, pen-and-tablet system, touch screen system, or spatial input device to place landmark points. The bone boundaries may include lines representative in the medical imaging slices of cortical bone boundaries.

In one embodiment of the method of manufacturing the custom arthroplasty guide, the image data associated with a bone other than the patient bone may include a golden bone model. In one embodiment of the method of manufacturing the custom arthroplasty guide, the image data of operation c) may include a model of a bone that is the same bone type as the patient bone, but representative of what is considered to be generally normal with respect to the bone type for at least one of size, condition, shape, weight, age, height, race, gender or diagnosed disease condition.

In one embodiment of the method of manufacturing the custom arthroplasty guide, operation d) includes deforming a mesh to match the landmarks, wherein the mesh is associated with the model data. For example, deforming the mesh to match the landmarks may include registering the mesh to the landmarks using at least one of translation transforms, similarity transforms or affine transforms.

Deforming the mesh to match the landmarks may further include detecting image edges near the mesh. For example, detecting image edges near the mesh may include computing a signed distance image for the mesh. Detecting the image edges near the mesh may further include computing a gradient of the signed distance image. Detecting the image edges near the mesh may yet further include computing a gradient of at least one of the medical imaging slices. Detecting the image edges near the mesh may still further include computing an edges image by correcting the gradient of at least one of the medical imaging slices with the gradient of the signed distance image.

In one embodiment of the method of manufacturing the custom arthroplasty guide, deforming the mesh to match the landmarks may yet further include registering simultaneously the mesh to the landmarks and to the image edges using B-spline deformable transforms.

In one embodiment of the method of manufacturing the custom arthroplasty guide, operation d) may further include generating segmentation curves from the deformed mesh. Operation d) may yet further include approximating the segmentation curves with spline curves. Additionally, operation d) may still further include modifying the spline curves to match the landmarks.

In one embodiment of the method of manufacturing the custom arthroplasty guide, modifying the spline curves to match the landmarks may include identifying a landmark from the landmarks and computing a distance of the spline curve to the indentified landmark. Modifying the spline curves to match the landmarks may further include identifying a closest arc of the spline curve to the identified landmark and modifying the closest arc to include the identified landmark, resulting in a modified spline curve. Modifying the spline curves to match the landmarks may yet further include computing distances from other landmarks to the modified spline curve and, if the distances are worse, disregarding the modification to the closest arc that resulted in the modified spline curve.

If the modification is disregarded, then modifying the spline curves to match the landmarks may still further include identifying a point in the closest arc that is closest to the identified landmark and inserting a spline vertex at the identified point. Modifying the spline curves to match the landmarks may still further include moving the inserted vertex to the identified landmark.

In one embodiment of the method of manufacturing the custom arthroplasty guide, in operation e) the three dimensional computer model of the portion of the patient bone may include: a bone only model that represents bone surfaces but no cartilage surfaces; or a restored bone model that represents bone surfaces but no cartilage surfaces.

In one embodiment of the method of manufacturing the custom arthroplasty guide, in operation e) the three dimensional computer model of the portion of the patient bone includes an arthritic model that represents both bone and cartilage surfaces.

In one embodiment of the method of manufacturing the custom arthroplasty guide, in operation f) the data associated with the custom arthroplasty guide may include at least one of data associated with the design of the surface contour of the mating region or a resection plane associated with a resection guide surface of the custom arthroplasty guide.

In one embodiment of the method of manufacturing the custom arthroplasty guide, in operation f) the data associated with the custom arthroplasty guide includes manufacturing instructions for manufacturing the custom arthroplasty guide.

In one embodiment of the method of manufacturing the custom arthroplasty guide, operation g) may include using the design data to guide a CNC machine or SLA machine (or other analogous additive or subtractive manufacturing technologies) in manufacturing the custom arthroplasty guide.

Yet another embodiment of manufacturing the above-described custom arthroplasty guide is disclosed herein. Specifically, the method of manufacturing the custom arthroplasty guide includes: a) generating medical imaging data of the portion of the patient bone; b) identifying landmarks associated with bone boundaries in the medical imaging data; c) providing a geometrical representation of an exemplary bone that is not the patient bone but is the same bone type as the patient bone and is representative of what is considered to be generally normal with respect to the bone type for at least one of size, condition, shape, weight, age, height, race, gender or diagnosed disease condition; d) adjusting the geometrical representation of the exemplary bone to match the landmarks; e) using the adjusted geometrical representation of the exemplary bone to generate a three dimensional computer model of the portion of the patient bone; f) using the three dimensional computer model to generate design data associated with the custom arthroplasty guide; and g) using the design data in manufacturing the custom arthroplasty guide. In one version of the embodiment, the geometrical representation of an exemplary bone includes a golden femur mesh or a golden tibia mesh.

Yet still another embodiment of manufacturing the above-described custom arthroplasty guide is disclosed herein. Specifically, the method of manufacturing the custom arthroplasty guide includes: a) generating medical imaging slices of the portion of the patient bone; b) identifying landmarks on cortical bone boundaries in the medical imaging data; c) providing golden bone image data that is not of the patient bone but is of the same bone type as the patient bone and is representative of what is considered to be generally typical with respect to a characteristic of bones such as the patient bone; d) segmenting the golden bone image data and generating a golden bone mesh from the segmented golden bone image data; e) deforming the golden bone mesh to match the landmarks; f) generating at least one of segmentation curves or spline curves from the deformed golden bone mesh; g) (optional) modify the at least one of segmentation curves or spline curves to match the landmarks; h) using the modified at least one of segmentation curves or spline curves to generate a three dimensional computer model generally representative of the portion of the patient bone; i) using the three dimensional computer model to generate design data associated with the custom arthroplasty guide; and j) using the design data in manufacturing the custom arthroplasty guide. In some versions of the embodiment with respect to operation c), the characteristic includes at least one of size, condition, shape, weight, age, height, race, gender or diagnosed disease condition.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 1B-1E are flow chart diagrams outlining the jig production method disclosed herein.

FIG. 31A is an isometric view of a closed golden femur mesh.

FIG. 31B is an isometric view of an open golden femur mesh created from the closed golden femur mesh of FIG. 31A.

FIG. 31C is the open femur mesh of FIG. 31B with regions of a different precision indicated.

DETAILED DESCRIPTION

Figure 1A:
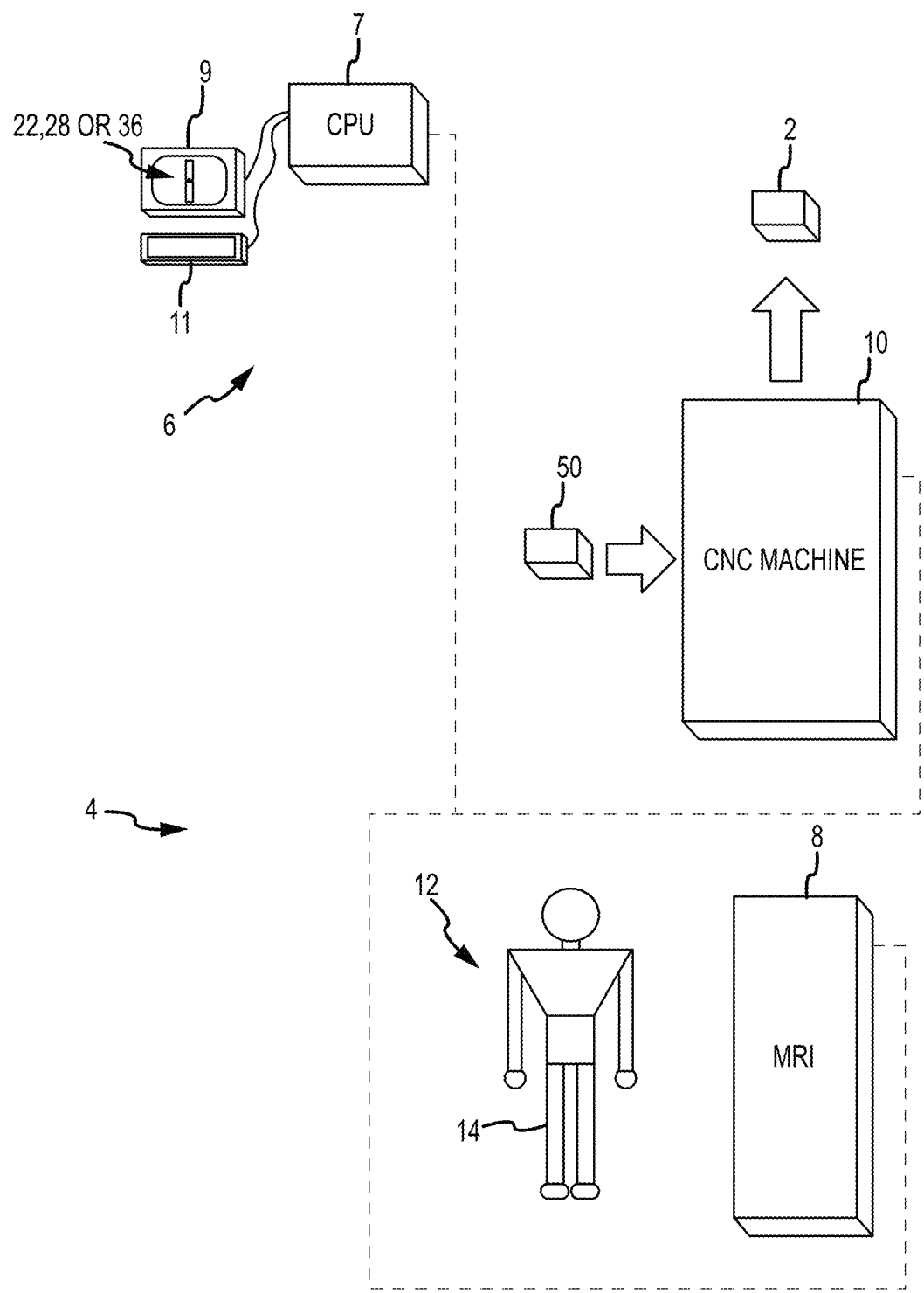
FIG. 1A is a schematic diagram of a system for employing the automated jig production method disclosed herein.

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. Patent Applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. Patent Applications are incorporated by reference in their entireties into this Detailed Description.

a. Overview of System and Method for Manufacturing Customized Arthroplasty Cutting Jigs For an overview discussion of the systems 4 for, and methods of, producing the customized arthroplasty jigs 2, reference is made to FIGS. 1A-1E. FIG. 1A is a schematic diagram of a system 4 for employing the automated jig production method disclosed herein. FIGS. 1B-1E are flow chart diagrams outlining the jig production method disclosed herein. The following overview discussion can be broken down into three sections.

The first section, which is discussed with respect to FIG. 1A and [blocks 100-125] of FIGS. 1B-1E, pertains to an example method of determining, in a three-dimensional ("3D") computer model environment, saw cut and drill hole locations 30, 32 relative to 3D computer models that are termed restored bone models 28 (also referenced as "planning models" throughout this submission.) In some embodiments, the resulting "saw cut and drill hole data" 44 is referenced to the restored bone models 28 to provide saw cuts and drill holes that will allow arthroplasty implants to restore the patient's joint to its pre-degenerated state. In other words, in some embodiments, the patient's joint may be restored to its natural alignment, whether valgus, varus or neutral.

While many of the embodiments disclosed herein are discussed with respect to allowing the arthroplasty implants to restore the patient's joint to its pre-degenerated or natural alignment state, many of the concepts disclosed herein may be applied to embodiments wherein the arthroplasty implants restore the patient's joint to a zero mechanical axis alignment such that the patient's knee joint ends up being neutral, regardless of whether the patient's predegenerated condition was varus, valgus or neutral. For example, as disclosed in U.S. patent application Ser. No. 12/760,388 to Park et al., titled "Preoperatively Planning An Arthroplasty Procedure And Generating A Corresponding Patient Specific Arthroplasty Resection Guide", filed Apr. 14, 2010, and incorporated by reference into this Detailed Description in its entirety, the system 4 for producing the customized arthroplasty jigs 2 may be such that the system initially generates the preoperative planning ("POP") associated with the jig in the context of the POP resulting in the patient's knee being restored to its natural alignment. Such a natural alignment POP is provided to the physician, and the physician determines if the POP should result in (1) natural alignment, (2) mechanical alignment, or (3) something between (1) and (2). The POP is then adjusted according to the physician's determination, the resulting jig 2 being configured such that the arthroplasty implants will restore the patient's joint to (1), (2) or (3), depending on whether the physician elected (1), (2) or (3), respectively. Accordingly, this disclosure should not be limited to methods resulting in natural alignment only, but should, where appropriate, be considered as applicable to methods resulting in natural alignment, zero mechanical axis alignment or an alignment somewhere between natural and zero mechanical axis alignment.

The second section, which is discussed with respect to FIG. 1A and [blocks 100-105 and 130-145] of FIGS. 1B-1E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

Figure 1C:
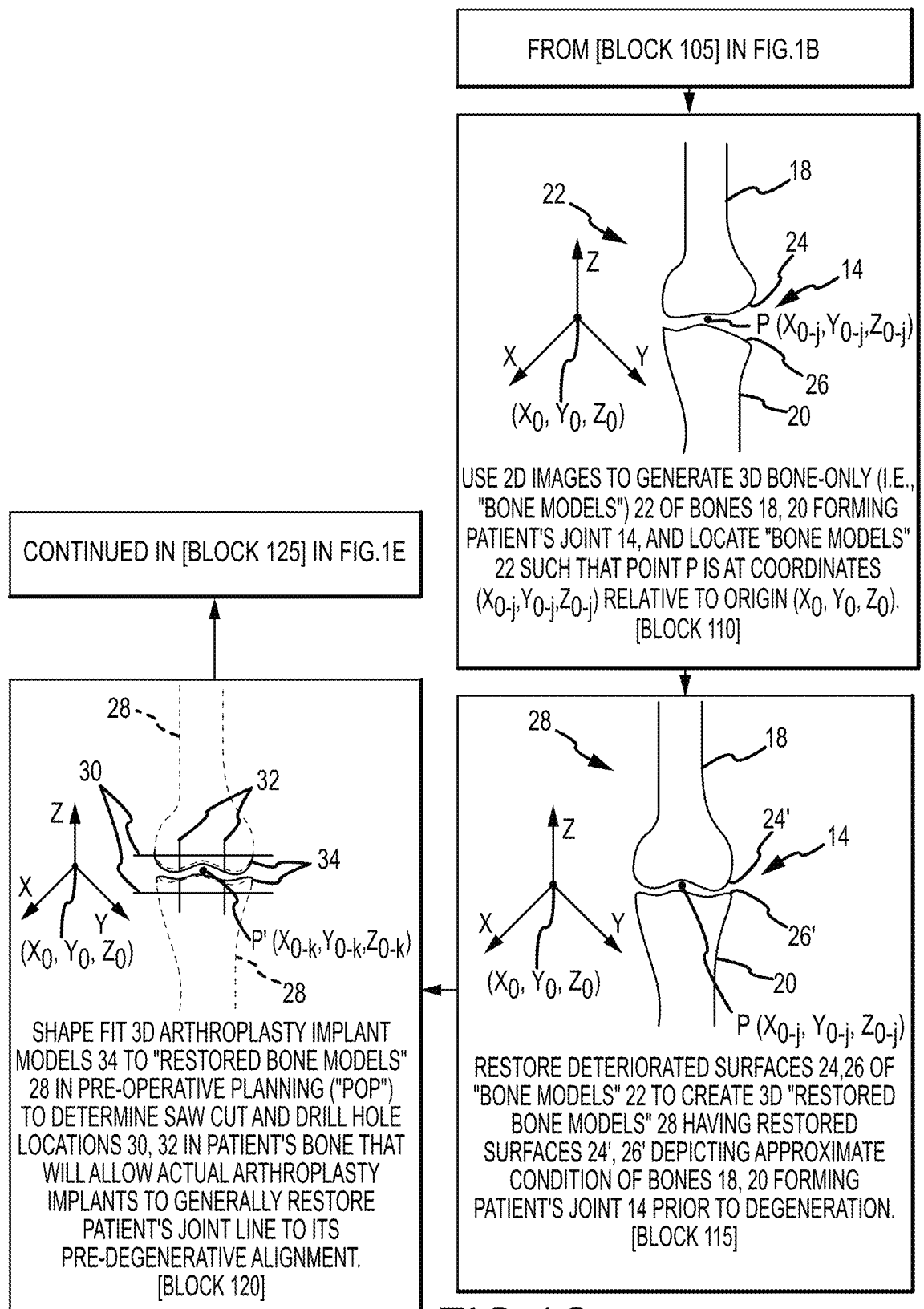
Figure 1D:
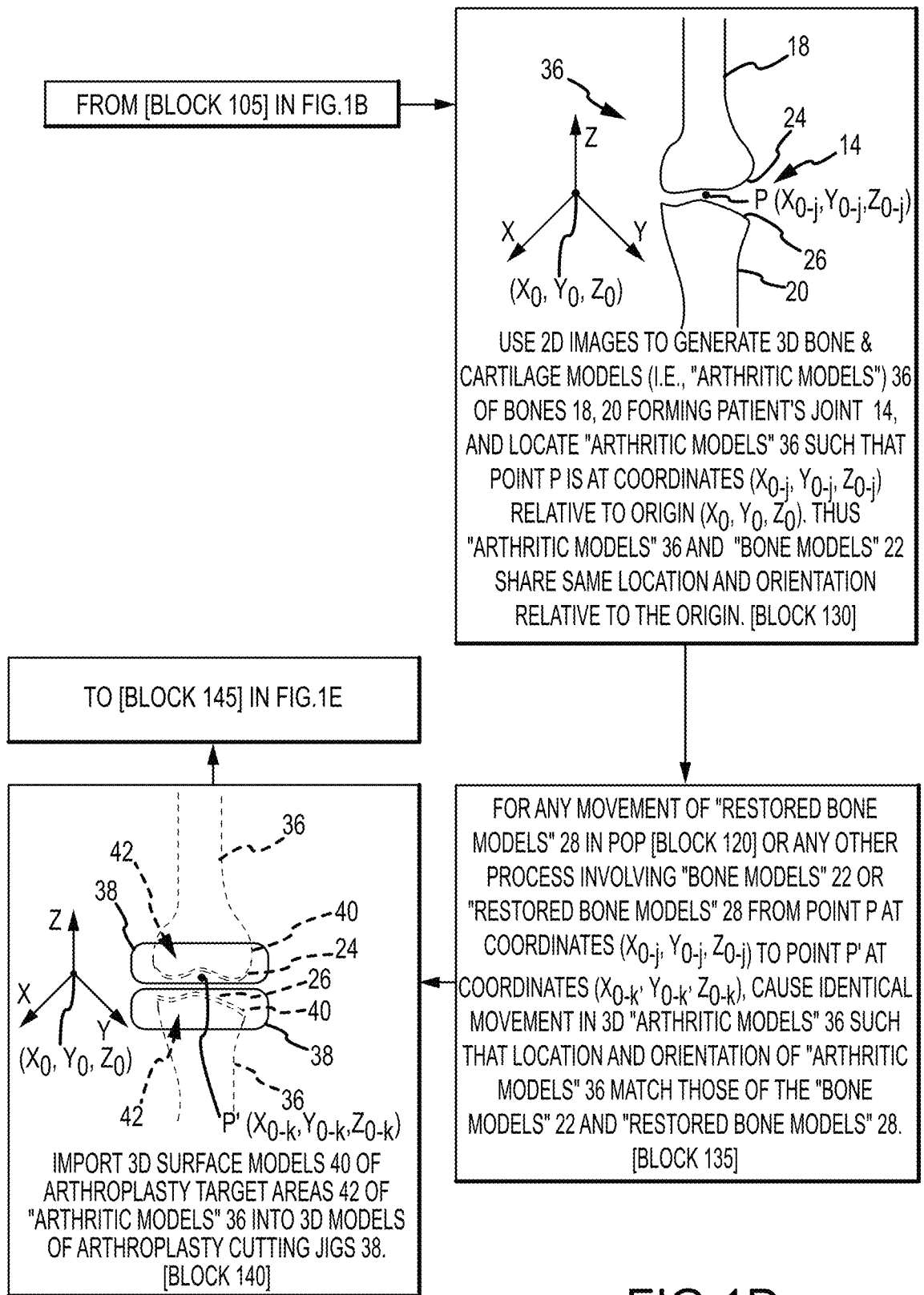
Figure 1E:
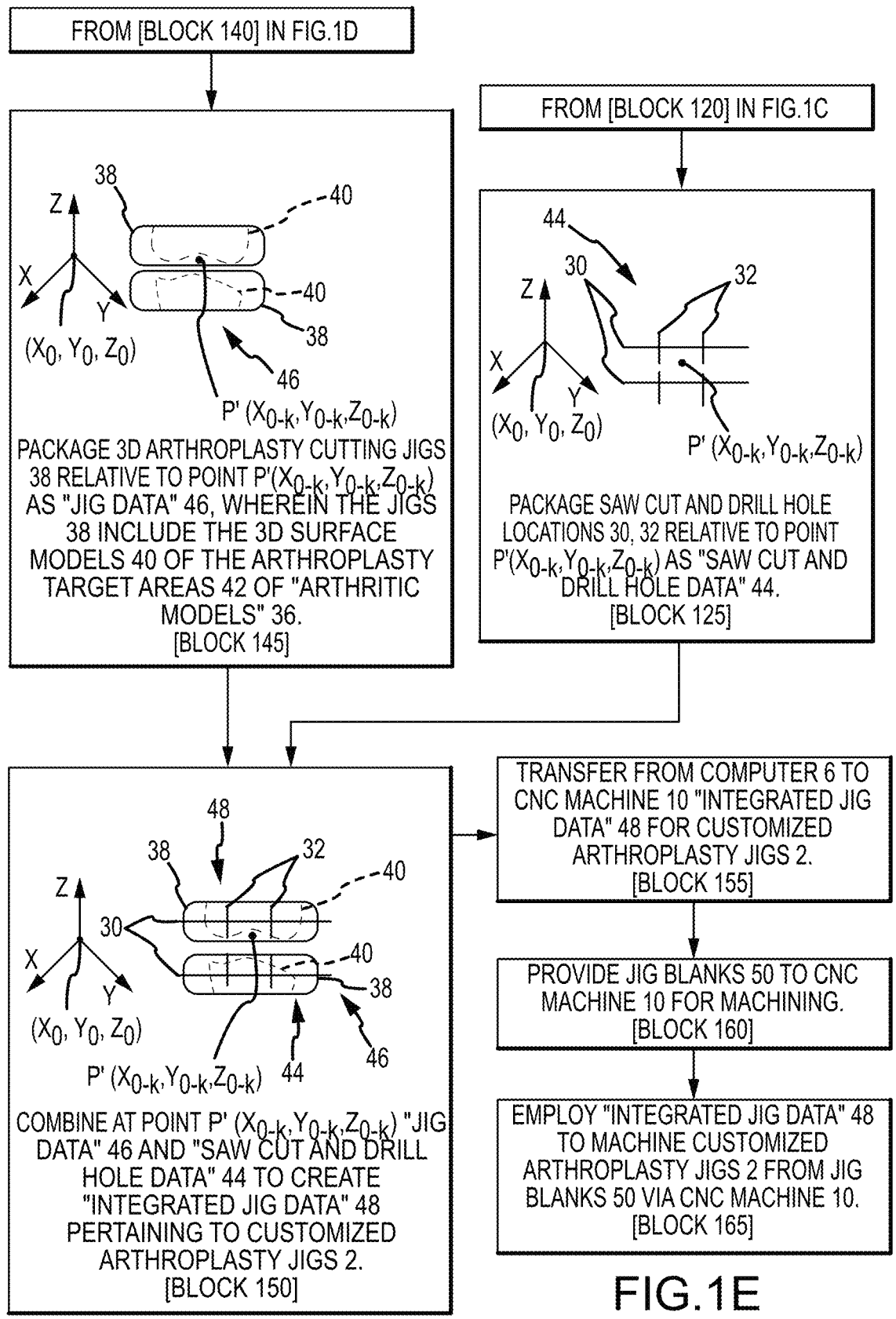

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state.

As shown in FIG. 1A, the system 4 includes one or more computers 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

In another embodiment, rather than using a single computer for the whole process, multiple computers can perform separate steps of the overall process, with each respective step managed by a respective technician skilled in that particular aspect of the overall process. The data generated in one process step on one computer can be then transferred for the next process step to another computer, for instance via a network connection.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D") images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description.

As can be understood from FIG. 1A, the 2D images are sent to the computer 6 for creating computer generated 3D models. As indicated in FIG. 1B, in one embodiment, point P is identified in the 2D images 16 [block 105]. In one embodiment, as indicated in [block 105] of FIG. 1A, point P may be at the approximate medial-lateral and anterior-posterior center of the patient's joint 14. In other embodiments, point P may be at any other location in the 2D images 16, including anywhere on, near or away from the bones 18, 20 or the joint 14 formed by the bones 18, 20.

As described later in this overview, point P may be used to locate the computer generated 3D models 22, 28, 36 created from the 2D images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D images 16.

As discussed in detail below, the 2D images 16 are segmented along bone boundaries to create bone contour lines. Also, the 2D images 16 are segmented along bone and cartilage boundaries to create bone and cartilage lines.

As shown in FIG. 1C, the segmented 2D images 16 (i.e., bone contour lines) are employed to create computer generated 3D bone-only (i.e., "bone models") 22 of the bones 18, 20 forming the patient's joint 14 [block 110]. The bone models 22 are located such that point P is at coordinates ($X_P$, $Y_P$, $Z_P$) relative to an origin ($X_0$, $Y_0$, $Z_0$) of an X-Y-Z coordinate system [block 110]. The bone models 22 depict the bones 18, 20 in the present deteriorated condition with their respective degenerated joint surfaces 24, 26, which may be a result of osteoarthritis, injury, a combination thereof, etc.

Computer programs for creating the 3D computer generated bone models 22 from the segmented 2D images 16 (i.e., bone contour lines) include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org. Further, some embodiments may use customized software such as OMSegmentation (renamed "PerForm" in later versions), developed by OtisMed, Inc. The OMSegmentation software may extensively use "ITK" and/or "VTK" (Visualization Toolkit from Kitware, Inc, available at www.vtk.org.) Some embodiments may include using a prototype of OMSegmentation, and as such may utilize InsightSNAP software.

As indicated in FIG. 1C, the 3D computer generated bone models 22 are utilized to create 3D computer generated "restored bone models" or "planning bone models" 28 wherein the degenerated surfaces 24, 26 are modified or restored to approximately their respective conditions prior to degeneration [block 115]. Thus, the bones 18, 20 of the restored bone models 28 are reflected in approximately their condition prior to degeneration. The restored bone models 28 are located such that point P is at coordinates ($X_P$, $Y_P$, $Z_P$) relative to the origin ($X_0$, $Y_0$, $Z_0$). Thus, the restored bone models 28 share the same orientation and positioning relative to the origin ($X_0$, $Y_0$, $Z_0$) as the bone models 22.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 surfaces on the 3D computer bone models 22 need to be modified to restore them to their pre-degenerated condition. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state.

In one embodiment, the bone restoration process is generally or completely automated. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state. For more detail regarding a generally or completely automated system for the bone restoration process, see U.S. patent application Ser. No. 12/111,924 to Park, which is titled "Generation of a Computerized Bone Model Representative of a Pre-Degenerated State and Usable in the Design and Manufacture of Arthroplasty Devices", was filed Apr. 29, 2008, and is incorporated by reference in its entirety into this Detailed Description.

As depicted in FIG. 1C, the restored bone models 28 are employed in a pre-operative planning ("POP") procedure to determine saw cut locations 30 and drill hole locations 32 in the patient's bones that will allow the arthroplasty joint implants to generally restore the patient's joint line to it pre-degenerative alignment [block 120].

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. By superimposing the implant models 34 over the restored bone models 28, or vice versa, the joint surfaces of the implant models 34 can be aligned or caused to correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. For example, a computer program may manipulate computer generated 3D implant models 34 (e.g., femur and tibia implants in the context of the joint being a knee) and restored bone models or planning bone models 28 relative to each other to determine the saw cut and drill hole locations 30, 32 relative to the restored bone models 28. The implant models 34 may be superimposed over the restored bone models 28, or vice versa. In one embodiment, the implant models 34 are located at point P' ($X_{P'}$, $Y_{P'}$, $Z_{P'}$) relative to the origin ($X_0$, $Y_0$, $Z_0$), and the restored bone models 28 are located at point P ($X_P$, $Y_P$, $Z_P$). To cause the joint surfaces of the models 28, 34 to correspond, the computer program may move the restored bone models 28 from point P ($X_P$, $Y_P$, $Z_P$) to point P' ($X_{P'}$, $Y_{P'}$, $Z_{P'}$), or vice versa. Once the joint surfaces of the models 28, 34 are in close proximity, the joint surfaces of the implant models 34 may be shape-matched to align or correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28. For more detail regarding a generally or completely automated system for the POP process, see U.S. patent application Ser. No. 12/563,809 to Park, which is titled Arthroplasty System and Related Methods, was filed Sep. 21, 2009, and is incorporated by reference in its entirety into this Detailed Description.

While the preceding discussion regarding the POP process is given in the context of the POP process employing the restored bone models as computer generated 3D bone models, in other embodiments, the POP process may take place without having to employ the 3D restored bone models, but instead taking placing as a series of 2D operations. For more detail regarding a generally or completely automated system for the POP process wherein the POP process does not employ the 3D restored bone models, but instead utilizes a series of 2D operations, see U.S. patent application Ser. No. 12/546,545 to Park, which is titled Arthroplasty System and Related Methods, was filed Aug. 24, 2009, and is incorporated by reference in its entirety into this Detailed Description.

As indicated in FIG. 1E, in one embodiment, the data 44 regarding the saw cut and drill hole locations 30, 32 relative to point P' ($X_{P'}$, $Y_{P'}$, $Z_{P'}$) is packaged or consolidated as the "saw cut and drill hole data" 44 [block 145]. The "saw cut and drill hole data" 44 is then used as discussed below with respect to [block 150] in FIG. 1E.

As can be understood from FIG. 1D, the 2D images 16 employed to generate the bone models 22 discussed above with respect to [block 110] of FIG. 1C are also segmented along bone and cartilage boundaries to form bone and cartilage contour lines that are used to create computer generated 3D bone and cartilage models (i.e., "arthritic models") 36 of the bones 18, 20 forming the patient's joint 14 [block 130]. Like the above-discussed bone models 22, the arthritic models 36 are located such that point P is at coordinates ($X_P$, $Y_P$, $Z_P$) relative to the origin ($X_0$, $Y_0$, $Z_0$) of the X-Y-Z axis [block 130]. Thus, the bone and arthritic models 22, 36 share the same location and orientation relative to the origin ($X_0$, $Y_0$, $Z_0$). This position/orientation relationship is generally maintained throughout the process discussed with respect to FIGS. 1B-1E. Accordingly, movements relative to the origin ($X_0$, $Y_0$, $Z_0$) of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the segmented 2D images 16 (i.e., bone and cartilage contour lines) include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org. Some embodiments may use customized software such as OMSegmentation (renamed "PerForm" in later versions), developed by OtisMed, Inc. The OMSegmentation software may extensively use "ITK" and/or "VTK" (Visualization Toolkit from Kitware, Inc, available at www.vtk.org.). Also, some embodiments may include using a prototype of OMSegmentation, and as such may utilize InsightSNAP software.

Similar to the bone models 22, the arthritic models 36 depict the bones 18, 20 in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the bone and arthritic models 36, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point P' ($X_{P'}$, $Y_{P'}$, $Z_{P'}$) can also be imported into the jig models 38, resulting in jig models 38 positioned and oriented relative to point P' ($X_{P'}$, $Y_{P'}$, $Z_{P'}$) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' ($X_P$, $Y_P$, $Z_P$) into the jig models 38, resulting in the jig models 38 being indexed to matingly receive the arthroplasty target areas 42 of the arthritic models 36. The resulting jig models 38 are also positioned and oriented relative to point P' ($X_{P'}$, $Y_{P'}$, $Z_{P'}$) to allow their integration with the bone cut and drill hole data 44 of [block 125].

In one embodiment, the arthritic models 36 may be 3D volumetric models as generated from a closed-loop process. In other embodiments, the arthritic models 36 may be 3D surface models as generated from an open-loop process.

As indicated in FIG. 1E, in one embodiment, the data regarding the jig models 38 and surface models 40 relative to point P' ($X_{P'}$, $Y_{P'}$, $Z_{P'}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state.

As can be understood from FIGS. 1A and 1E, the "integrated jig data" 44 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50.

Figure 1F:
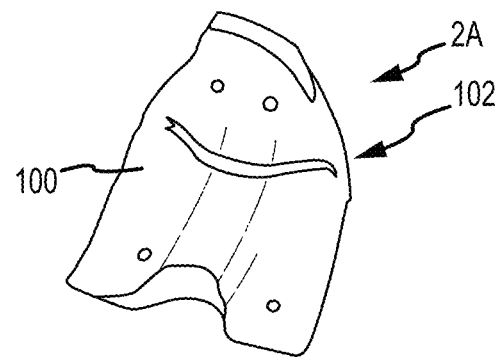
FIGS. 1F and 1G are, respectively, bottom and top perspective views of an example customized arthroplasty femur jig.
Figure 1G:
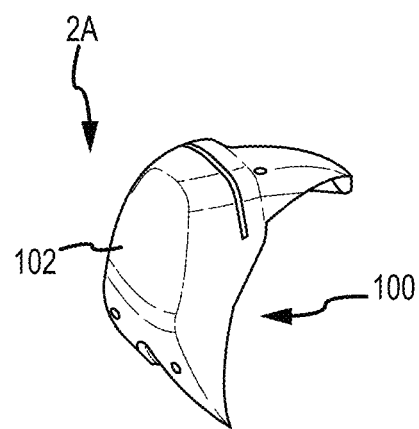
Figure 1H:
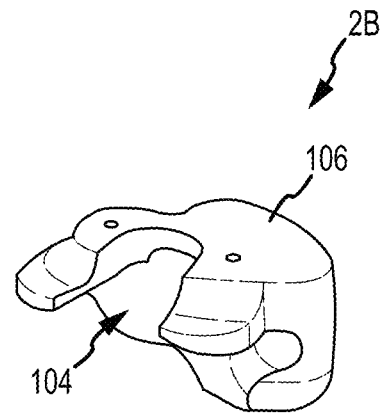
FIGS. 1H and 1I are, respectively, bottom and top perspective views of an example customized arthroplasty tibia jig.
Figure 1I:
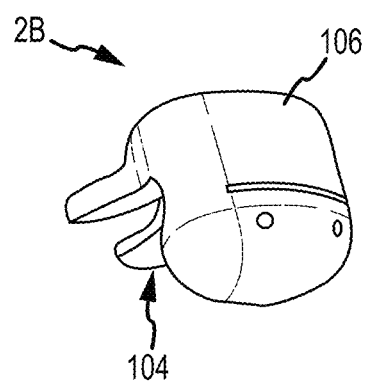

For a discussion of example customized arthroplasty cutting jigs 2 capable of being manufactured via the above-discussed process, reference is made to FIGS. 1F-1I. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 1F-1I are for total knee replacement ("TKR") or partial knee replacement ("PKR") procedures. Thus, FIGS. 1F and 1G are, respectively, bottom and top perspective views of an example customized arthroplasty femur jig 2A, and FIGS. 1H and 1I are, respectively, bottom and top perspective views of an example customized arthroplasty tibia jig 2B.

As indicated in FIGS. 1F and 1G, a femur arthroplasty jig 2A may include an interior side or portion 100 and an exterior side or portion 102. When the femur cutting jig 2A is used in a TKR or PKR procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR or PKR surgery, the surfaces of the target area 42 and the interior portion 100 match.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 1H and 1I, a tibia arthroplasty jig 2B may include an interior side or portion 104 and an exterior side or portion 106. When the tibia cutting jig 2B is used in a TKR or PKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR or PKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20.

b. Automatic Segmentation of Scanner Modality Image Data to Generate 3D Surface Model of a Patient's Bone In one embodiment as mentioned above, the 2D images 16 of the patient's joint 14 as generated via the imaging system 8 (see FIG. 1A and [block 100] of FIG. 1B) are segmented or, in other words, analyzed to identify the contour lines of the bones and/or cartilage surfaces that are of significance with respect to generating 3D models 22, 36, as discussed above with respect to [blocks 110 and 130] of FIGS. 1C and 1D. Specifically, a variety of image segmentation processes may occur with respect to the 2D images 16 and the data associated with such 2D images 16 to identify contour lines that are then compiled into 3D bone models, such as bone models 22 and arthritic models 36. A variety of processes and methods for performing image segmentation are disclosed in the remainder of this Detailed Description.

Figure 2A:
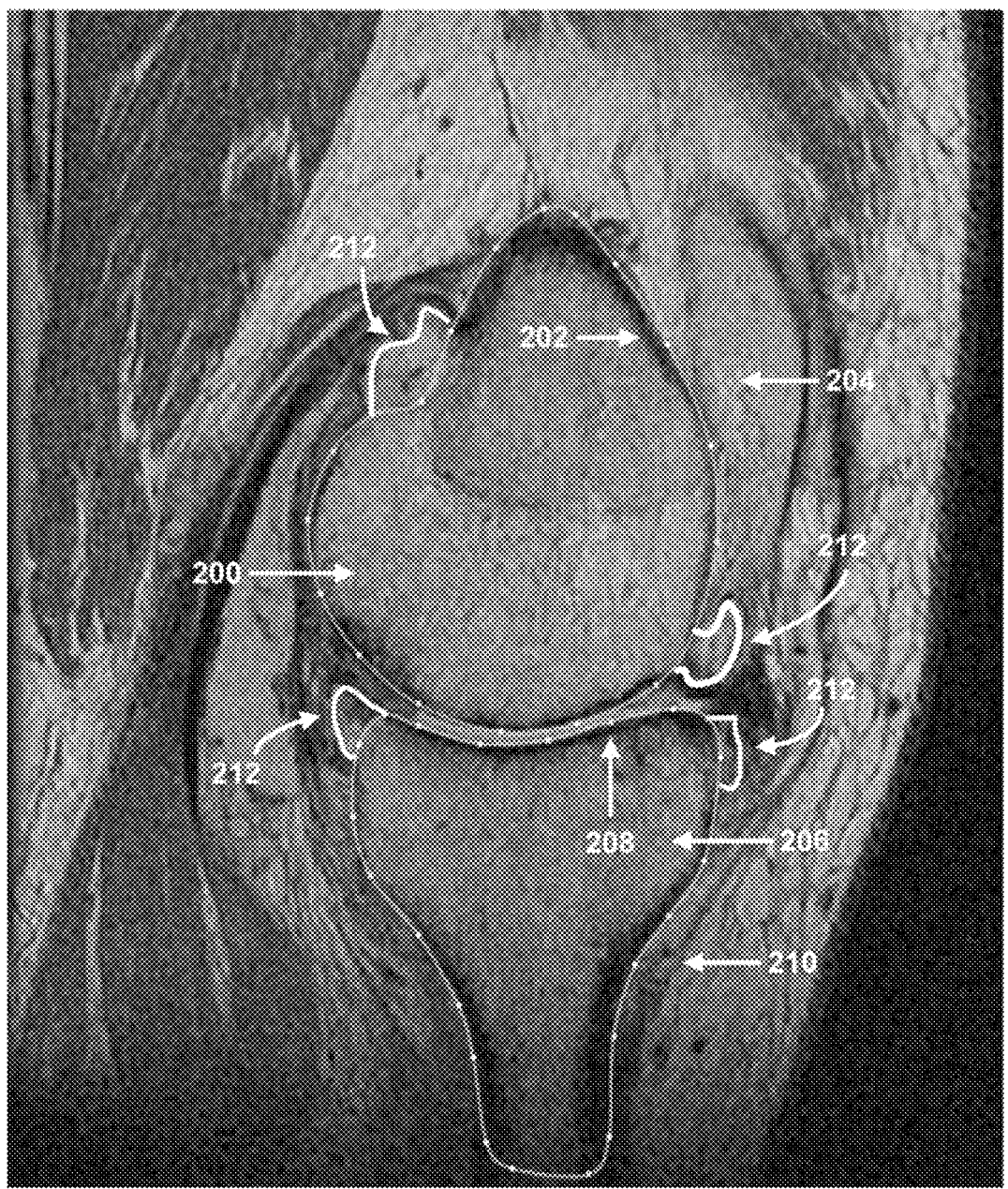
FIG. 2A is a sagittal plane image slice depicting a femur and tibia and neighboring tissue regions with similar image intensity.

The imager 8 typically generates a plurality of image slices 16 via repetitive imaging operations. Depending on whether the imager 8 is a MRI or CT imager, each image slice will be a MRI or CT slice. As shown in FIG. 2A, the image slice may depict the cancellous bone 200, the cortical bone 202 surrounding the cancellous bone, and the articular cartilage lining portions of the cortical bone 202 of an object of interest of a joint, e.g., a femur 204 in a patient's knee joint 14. The image may further depict the cancellous bone 206, the cortical bone 208 of another object of interest in the joint, e.g., a tibia 210 of the knee joint 14. In one embodiment, each image slice 16 may be a two-millimeter 2D image slice.

One embodiment may automatically segment one or more features of interest (e.g., bones) present in MRI or CT scans of a patient joint, e.g., knee, hip, elbow, etc. A typical scan of a knee joint may represent approximately a 100-millimeter by 150-millimeter by 150-millimeter volume of the joint and may include about 40 to 80 slices taken in sagittal planes. A sagittal plane is an imaginary plane that travels from the top to the bottom of the object (e.g., the human body), dividing it into medial and lateral portions. It is to be appreciated that a large inter-slice spacing may result in voxels (volume elements) with aspect ratios of about one to seven between the resolution in the sagittal plane (e.g., the y z plane) and the resolution along the x axis (i.e., each scan slice lies in the yz plane with a fixed value of x). For example, a two-millimeter slice that is 150-millimeters by 150-millimeters may be comprised of voxels that are approximately 0.3-millimeter by 0.3-millimeter by 2-millimeters (for a 512 by 512 image resolution in the sagittal plane).

In one embodiment, each slice may be a gray scale image with a resolution of 512 by 512 voxels where the voxel value represents the brightness (intensity) of the voxel. The intensity may be stored as a 16-bit integer resulting in an intensity range from 0 to 65,535, where 0 may represent black and 65,535 may represent white. The intensity of each voxel typically represents the average intensity of the voxel volume. Other embodiments may employ scans having higher or lower resolutions in the sagittal plane, different inter-slice spacing, or images where the intensity may be represented by a 24 bit vector (e.g., eight bits each for a red component, green component and blue component). Additionally, other embodiments may store intensity values as 32-bit signed integers or floating point values.

Figure 2B:
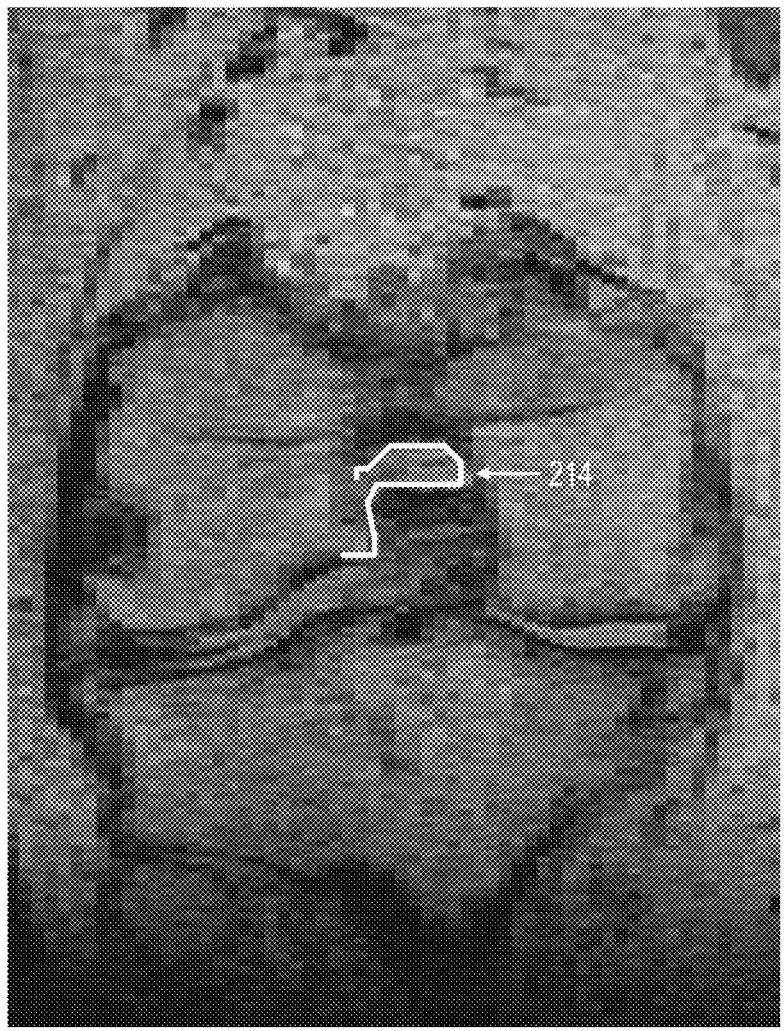
FIG. 2B is a sagittal plane image slice depicting a region extending into the slice from an adjacent image slice.
Figure 2C:
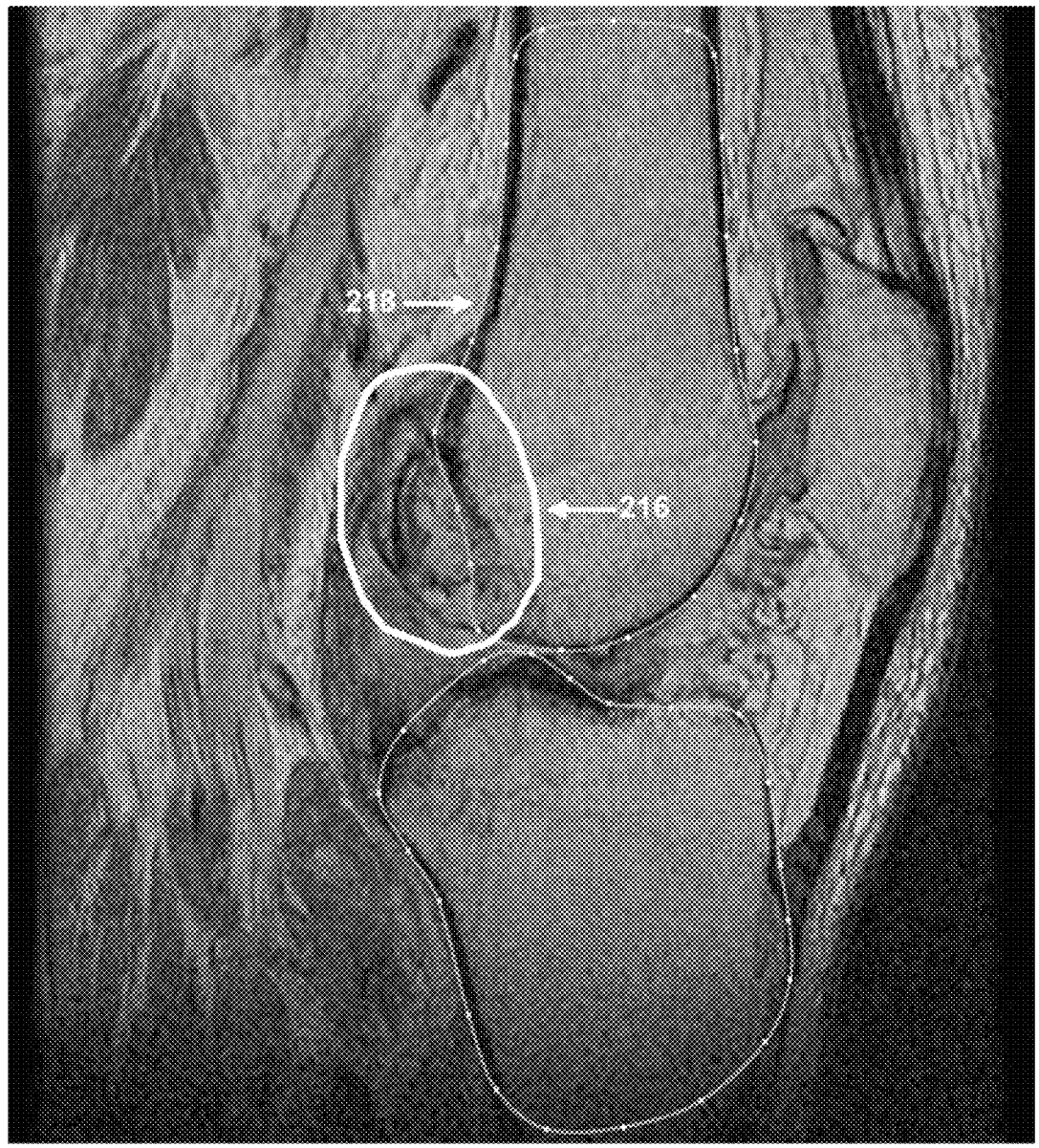
FIG. 2C is a sagittal plane image slice depicting a region of a femur that is approximately tangent to the image slice.

Typical MRI and CT scan data generally provide images where parts of a bone boundary of interest may be well defined while other parts of the bone boundary may be difficult to determine due to voxel volume averaging, the presence of osteophyte growth, the presence of tissue having similar image intensities in neighboring areas to the object to be segmented, amongst other things. Such poor definition of parts of the bone boundary in the images may cause traditional automated segmentation techniques to fail. For example, FIG. 2A depicts regions 212 within a slice where an object boundary may not be visible due to neighboring tissue having about the same intensity as the feature of interest. Depicted in FIG. 2B are regions 214 that may be extended into the slice from adjacent slices due to a high voxel aspect ratio. Depicted in FIG. 2C is a region 216 of the bone boundary 218 that may disappear or lose regularity when the bone boundary 218 is approximately tangent to the slice.

One embodiment may employ image segmentation techniques using a golden template to segment bone boundaries and provide improved segmentation results over traditional automated segmentation techniques. Such techniques may be used to segment an image when similarity between pixels within an object to be identified may not exist. That is, the pixels within a region to be segmented may not be similar with respect to some characteristic or computed property such as a color, intensity or texture that may be employed to associate similar pixels into regions. Instead, a spatial relationship of the object with respect to other objects may be used to identify the object of interest. In one embodiment, a 3D golden template of a feature of interest to be segmented may be used during the segmentation process to locate the target feature in a target scan. For example, when segmenting a scan of a knee joint, a typical 3D image of a known good femur (referred to as a golden femur template) may be used to locate and outline (i.e., segment) a femur in a target scan.

Generally, much of the tissues surrounding the cancellous and cortical matter of the bone to be segmented may vary from one MRI scan to another MRI scan. This may be due to disease and/or patient joint position (e.g., a patient may not be able to straighten the joint of interest because of pain). By using surrounding regions that have a stable connection with the bone (e.g., the grown golden and boundary golden regions of the template as described in more detail below), the registration may be improved. Additionally, use of these regions allows the bone geometry of interest to be captured during the segmentation rather than other features not of interest. Further, the segmentation takes advantage of the higher resolution of features of interest in certain directions of the scan data through the use of a combination of 2D and 3D techniques, that selectively increases the precision of the segmentation as described in more detail below with respect to refining the bone registration using an artificially generated image.

Figure 3A:
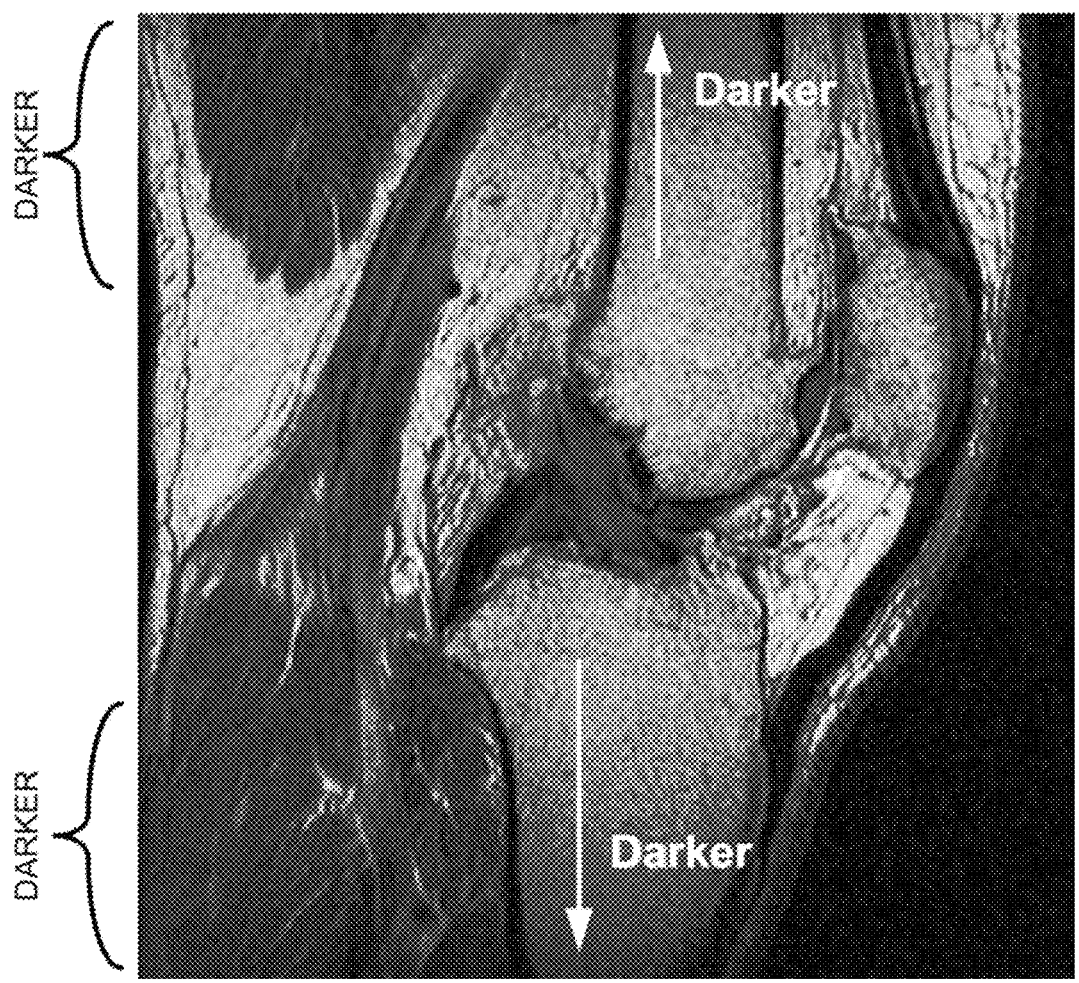
FIG. 3A is a sagittal plane image slice depicting an intensity gradient across the slice.
Figure 3B:
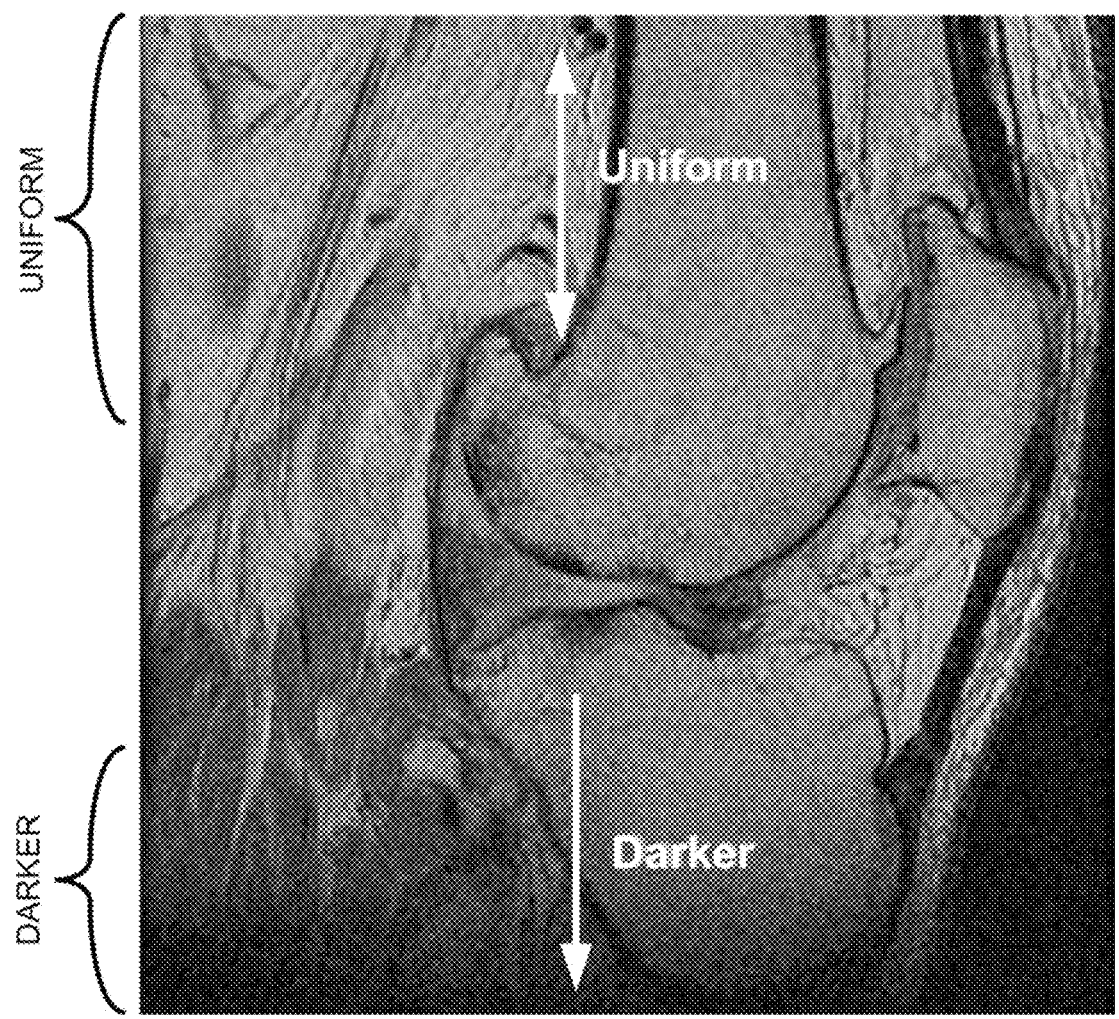
FIG. 3B is a sagittal plane image slice depicting another intensity gradient across the slice.
Figure 3C:
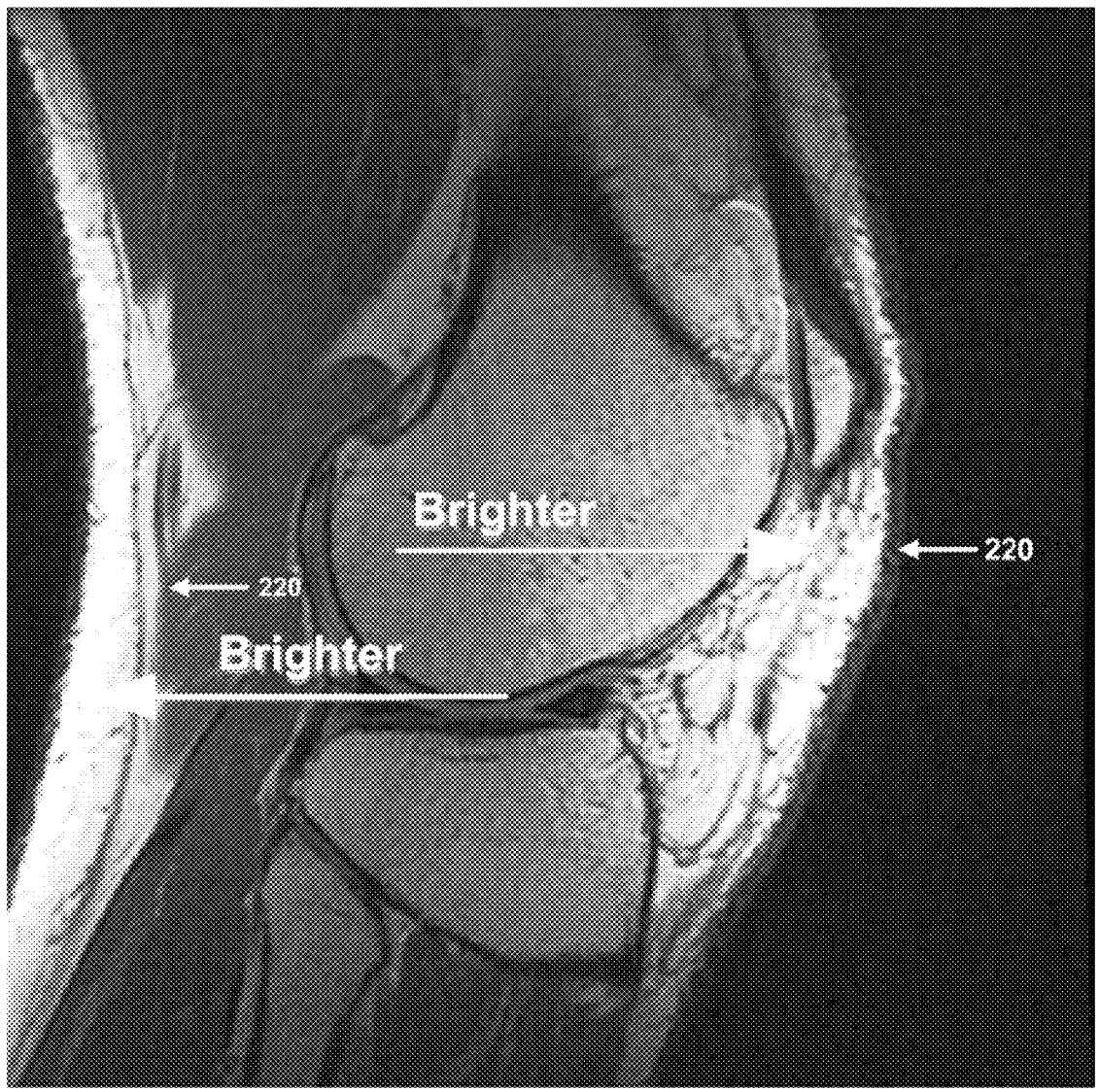
FIG. 3C is a sagittal plane image slice depicting another intensity gradient across the slice.
Figure 4A:
FIG. 4A depicts a sagittal plane image slice with a high noise level.
Figure 4B:
FIG. 4B depicts a sagittal plane image slice with a low noise level.

The segmentation method employed by one embodiment may accommodate a variety of intensity gradients across the scan data. FIGS. 3A-C depict intensity gradients (i.e., the intensity varies non-uniformly across the image) in slices (an intensity gradient that is darker on the top and bottom as depicted in FIG. 3A, an intensity gradient that is darker on the bottom as depicted in FIG. 3B, and an intensity gradient 220 that is brighter on the sides as depicted in FIG. 3C) that may be segmented by one embodiment. Further, the embodiment generally does not require approximately constant noise in the slices to be segmented. The embodiment may accommodate different noise levels, e.g., high noise levels as depicted in FIG. 4A as well as low noise levels as depicted in FIG. 4B. The decreased sensitivity to intensity gradients and noise level typically is due to image registration techniques using a golden template, allowing features of interest to be identified even though the feature may include voxels with differing intensities and noise levels.

Segmentation generally refers to the process of partitioning a digital image into multiple regions (e.g., sets of pixels for a 2D image or sets of voxels in a 3D image). Segmentation may be used to locate features of interest (bones, cartilage, ligaments, etc.) and boundaries (lines, curves, etc. that represent the bone boundary or surface) in an image. In one embodiment, the output of the automatic segmentation of the scan data may be a set of images (scan slices 16) where each image 16 includes a set of extracted closed contours representing bone outlines that identify respective bone location and shape for bones of interest (e.g., the shape and location of the tibia and femur in the scan data of a knee joint). The generation of a 3D model correspondent to the above closed contours may be additionally included into the segmentation process. The automatic or semi-automatic segmentation of a joint, using image slices 16 to create 3D models (e.g., bone models 22 and arthritic models 36) of the surface of the bones in the joint, may reduce the time required to manufacture customized arthroplasty cutting jigs 2. It is to be appreciated that certain embodiments may generate open contours of the bone shapes of interest to further reduce time associated with the process.

In one embodiment, scan protocols may be chosen to provide good definition in areas where precise geometry reconstruction is required and to provide lower definition in areas that are not as important for geometry reconstruction. The automatic or semi-automatic image segmentation of one embodiment employs components whose parameters may be tuned for the characteristics of the image modality used as input to the automatic segmentation and for the features of the anatomical structure to be segmented, as described in more detail below.

In one embodiment, a General Electric 3T MRI scanner may be used to obtain the scan data. The scanner settings may be set as follows: pulse sequence: FRFSE-XL Sagittal PD; 3 Pane Locator—Scout Scan Thickness: 4-millimeters; Imaging Options: TRF, Fast, FR; Gradient Mode: Whole; TE: approximately 31; TR: approximately 2100; Echo Train Length: 8; Bandwidth: 50 Hz; FOV: 16 centimeters, centered at the joint line; Phase FOV: 0.8 or 0.9; Slice Thickness: 2 millimeters; Spacing: Interleave; Matrix: 384×192; NEX: 2; Frequency: SI; and Phase Correct: On. It is to be appreciated that other scanners and settings may be used to generate the scan data.

Typically, the voxel aspect ratio of the scan data is a function of how many scan slices may be obtained while a patient remains immobile. In one embodiment, a two-millimeter inter-slice spacing may be used during a scan of a patient's knee joint. This inter-slice spacing provides sufficient resolution for constructing 3D bone models of the patient's knee joint, while allowing sufficiently rapid completion of scan before the patient moves.

Figure 5:
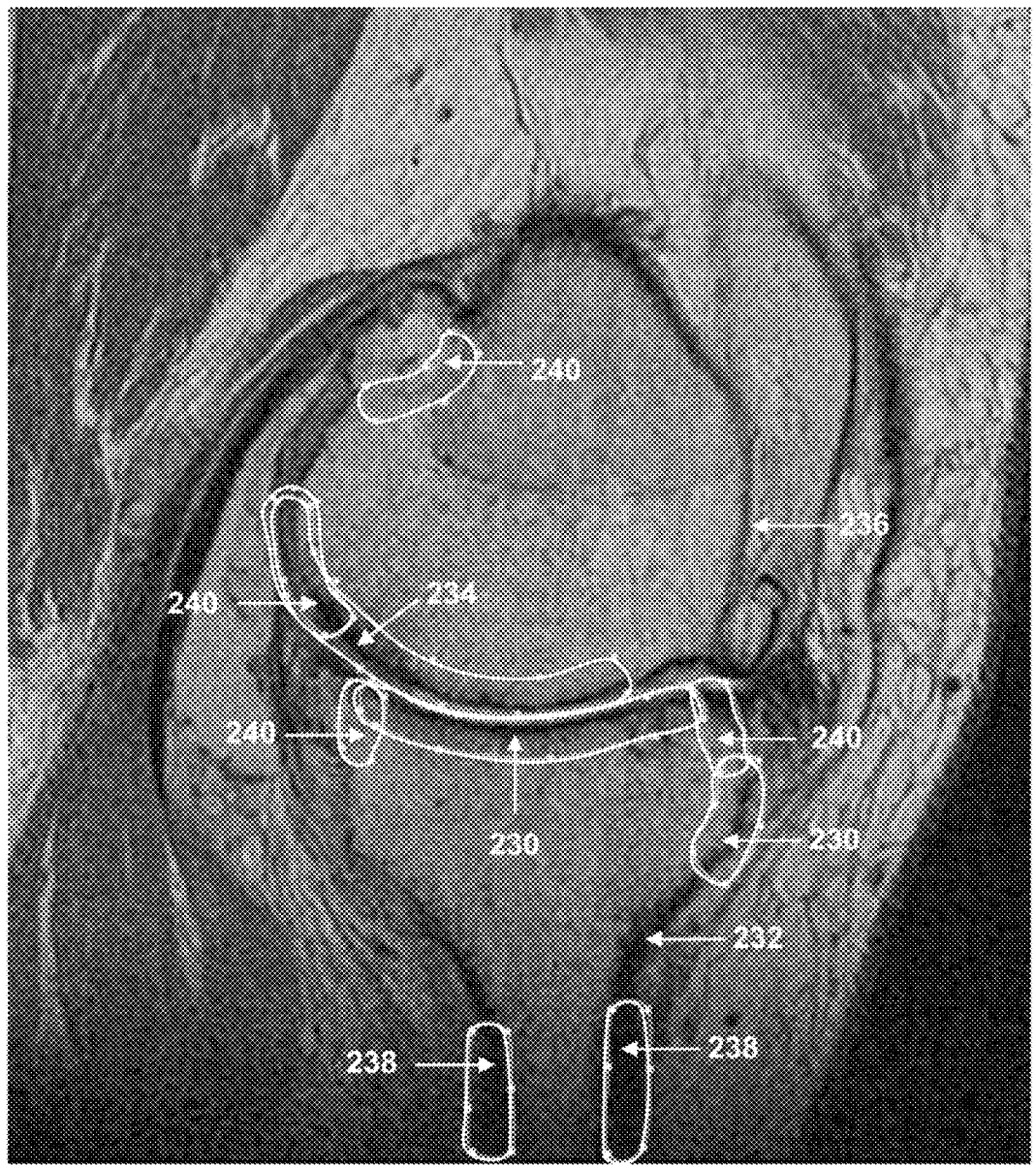
FIG. 5 is a sagittal plane image slice of a femur and tibia depicting regions where good definition may be needed during automatic segmentation of the femur and tibia.

FIG. 5 depicts a MRI scan slice that illustrates image regions where good definition may be needed during automatic segmentation of the image. Typically, this may be areas where the bones come in contact during knee motion, in the anterior shaft area next to the joint and areas located at about a 10- to 30-millimeter distance from the joint. Good definition may be needed in regions 230 of the tibia 232 and regions 234 of the femur 236. Regions 238 depict areas where the tibia is almost tangent to the slice and boundary information may be lost due to voxel volume averaging.

Voxel volume averaging may occur during the data acquisition process when the voxel size is larger than a feature detail to be distinguished. For example, the detail may have a black intensity while the surrounding region may have a white intensity. When the average of the contiguous data enclosed in the voxel is taken, the average voxel intensity value may be gray. Thus, it may not be possible to determine in what part of the voxel the detail belongs.

Regions 240 depict areas where the interface between the cortical bone and cartilage is not clear (because the intensities are similar), or where the bone is damaged and may need to be restored, or regions where the interface between the cancellous bone and surrounding region may be unclear due to the presence of a disease formation (e.g., an osteophyte growth which has an image intensity similar to the adjacent region).

Figure 6:
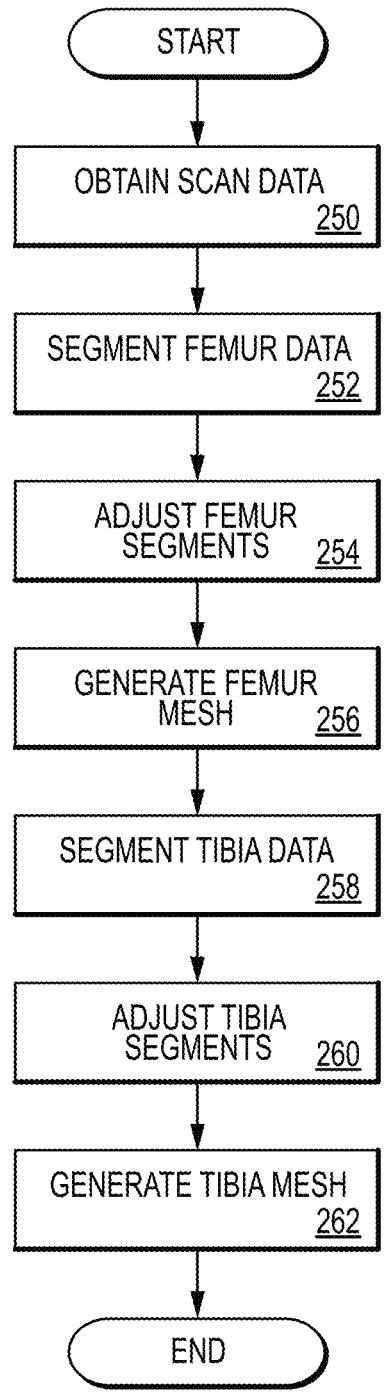
FIG. 6 depicts a flowchart illustrating one method for automatic segmentation of an image modality scan of a patient's knee joint.
Figure 7A:
FIG. 7A is a sagittal plane image slice of a segmented femur.
Figure 7B:
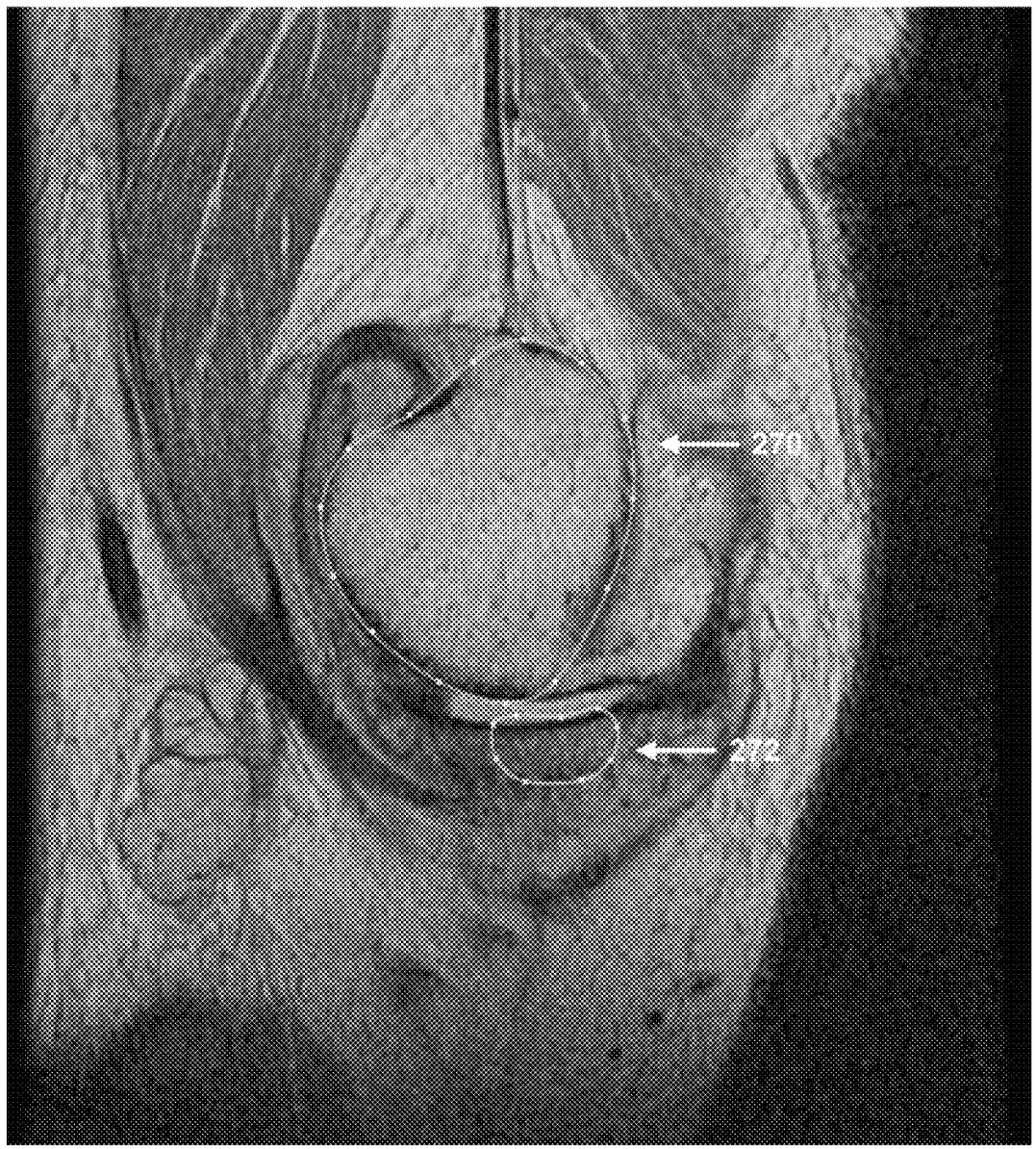
FIG. 7B is a sagittal plane image slice of a segmented femur and tibia.
Figure 7C:
FIG. 7C is another sagittal plane image slice of a segmented femur and tibia.
Figure 7D:
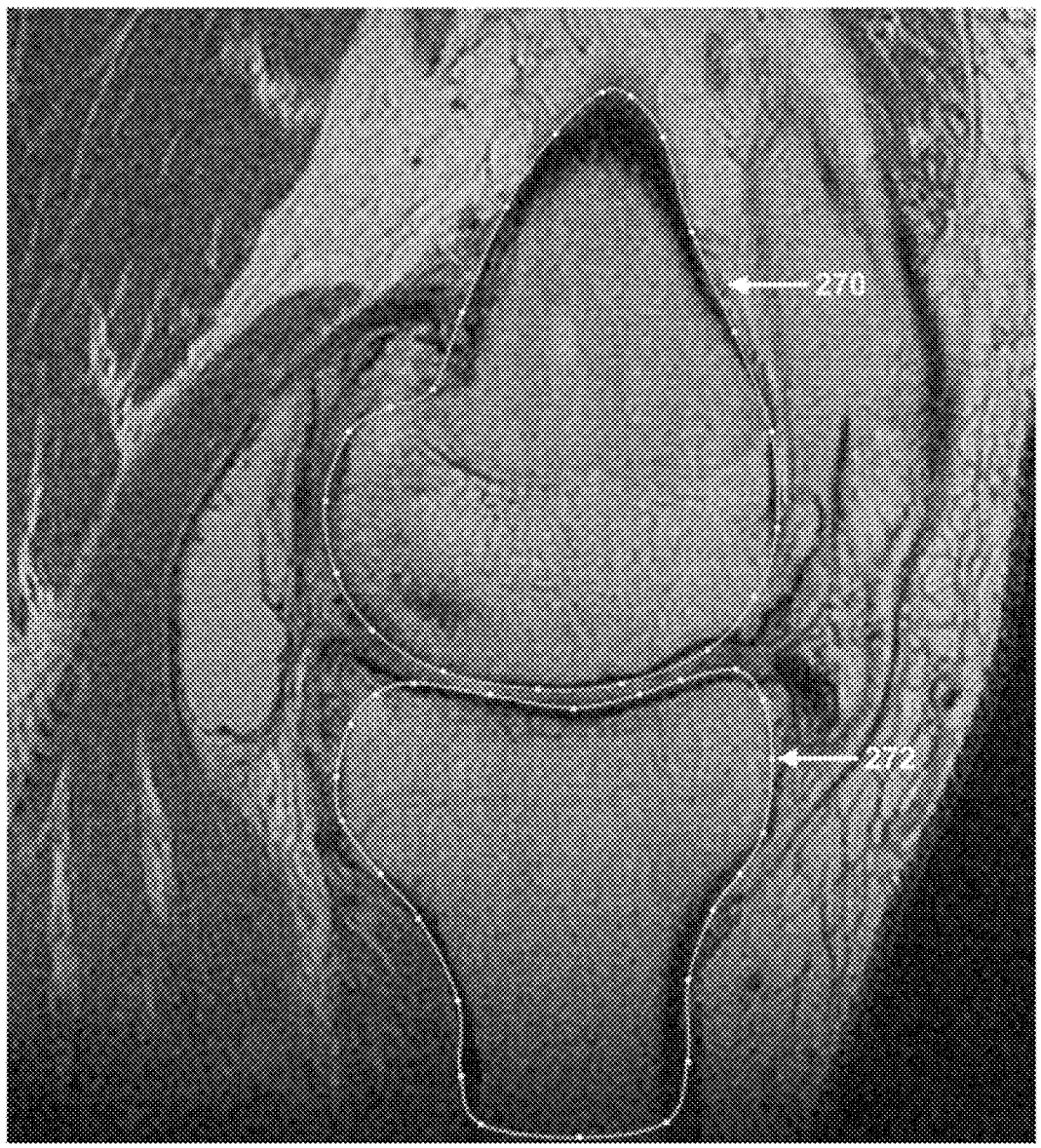
FIG. 7D is another sagittal plane image slice of a segmented femur and tibia.
Figure 7E:
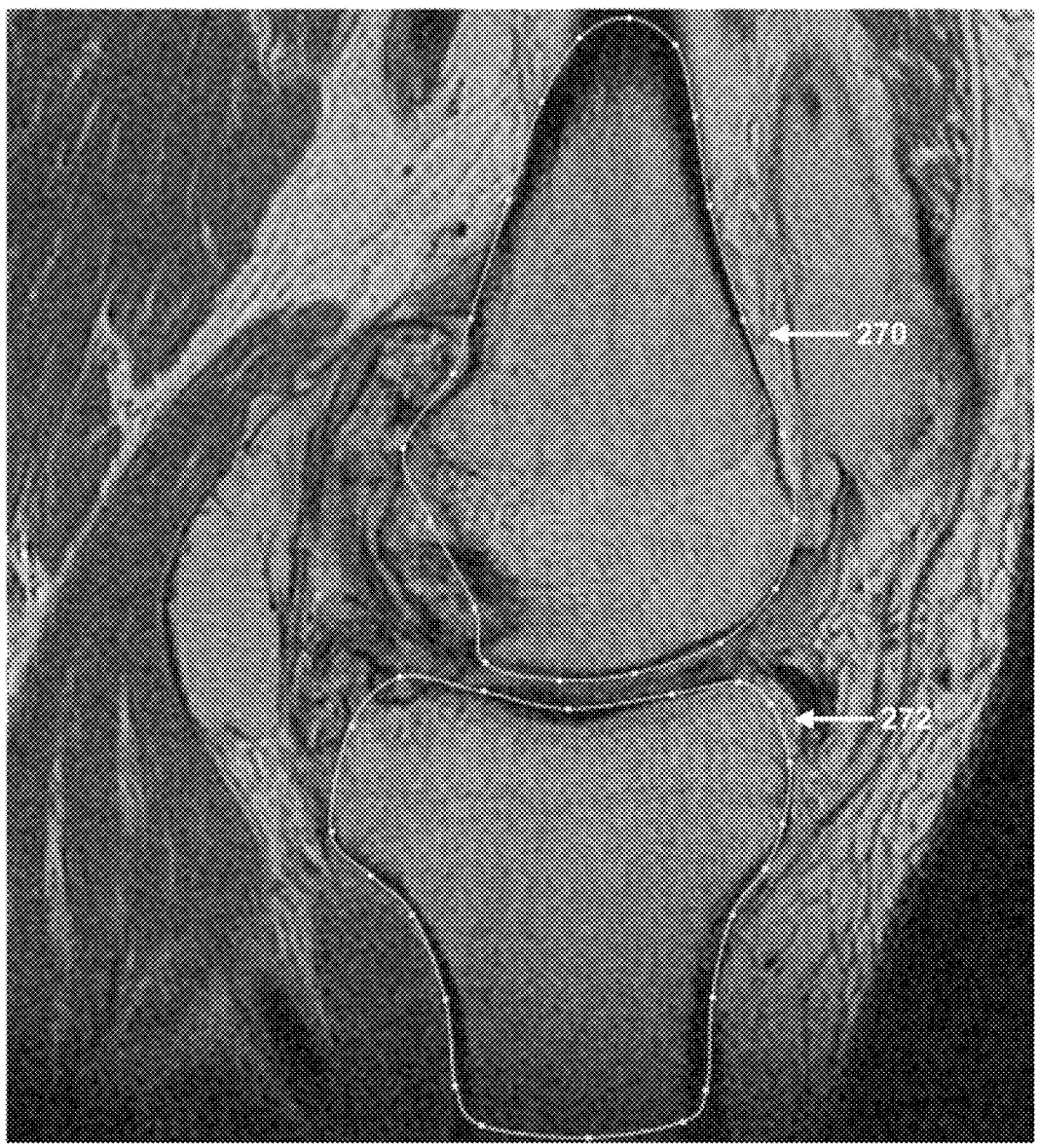
FIG. 7E is another sagittal plane image slice of a segmented femur and tibia.
Figure 7F:
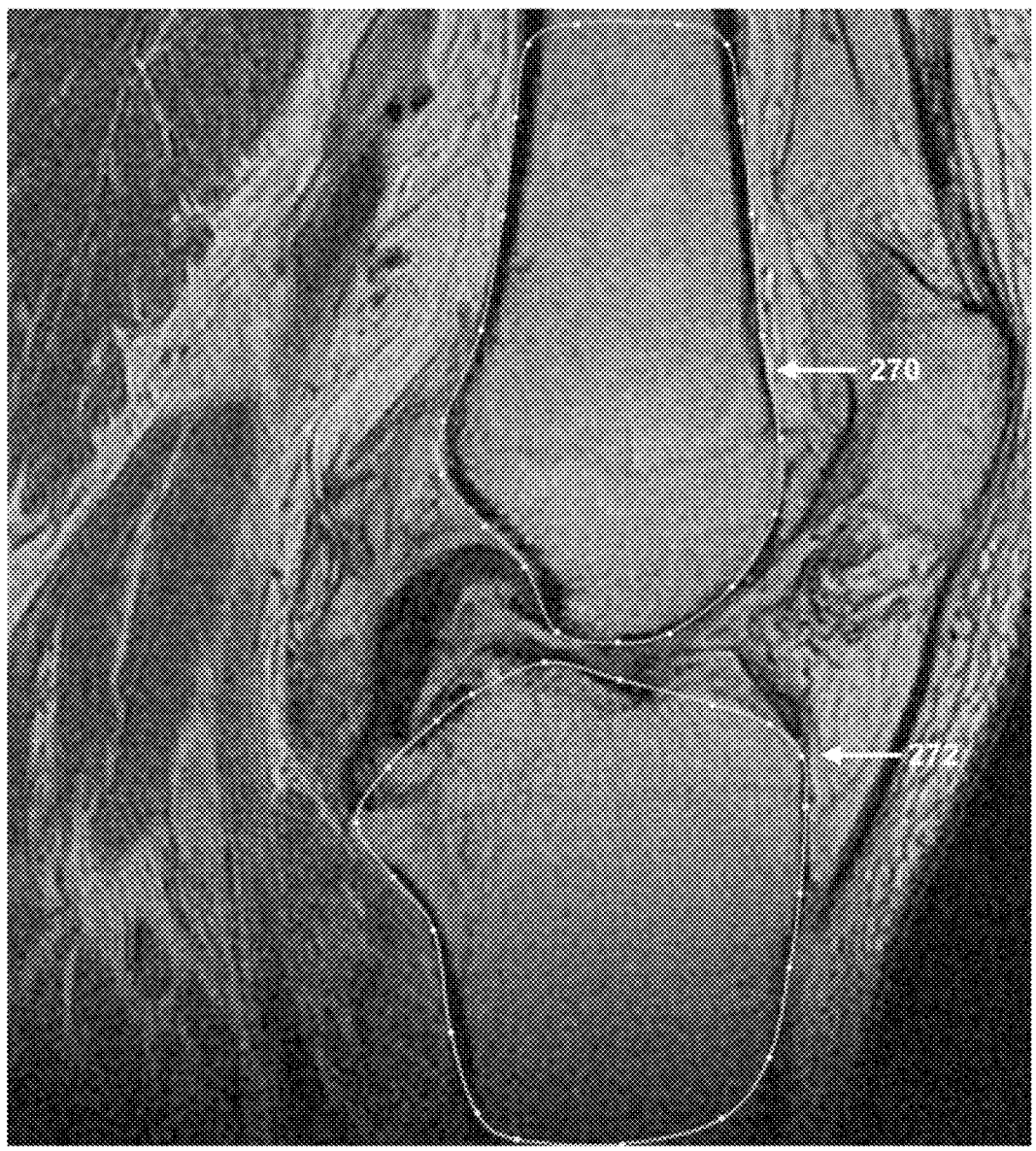
FIG. 7F is another sagittal plane image slice of a segmented femur and tibia.
Figure 7G:
FIG. 7G is another sagittal plane image slice of a segmented femur and tibia.
Figure 7H:
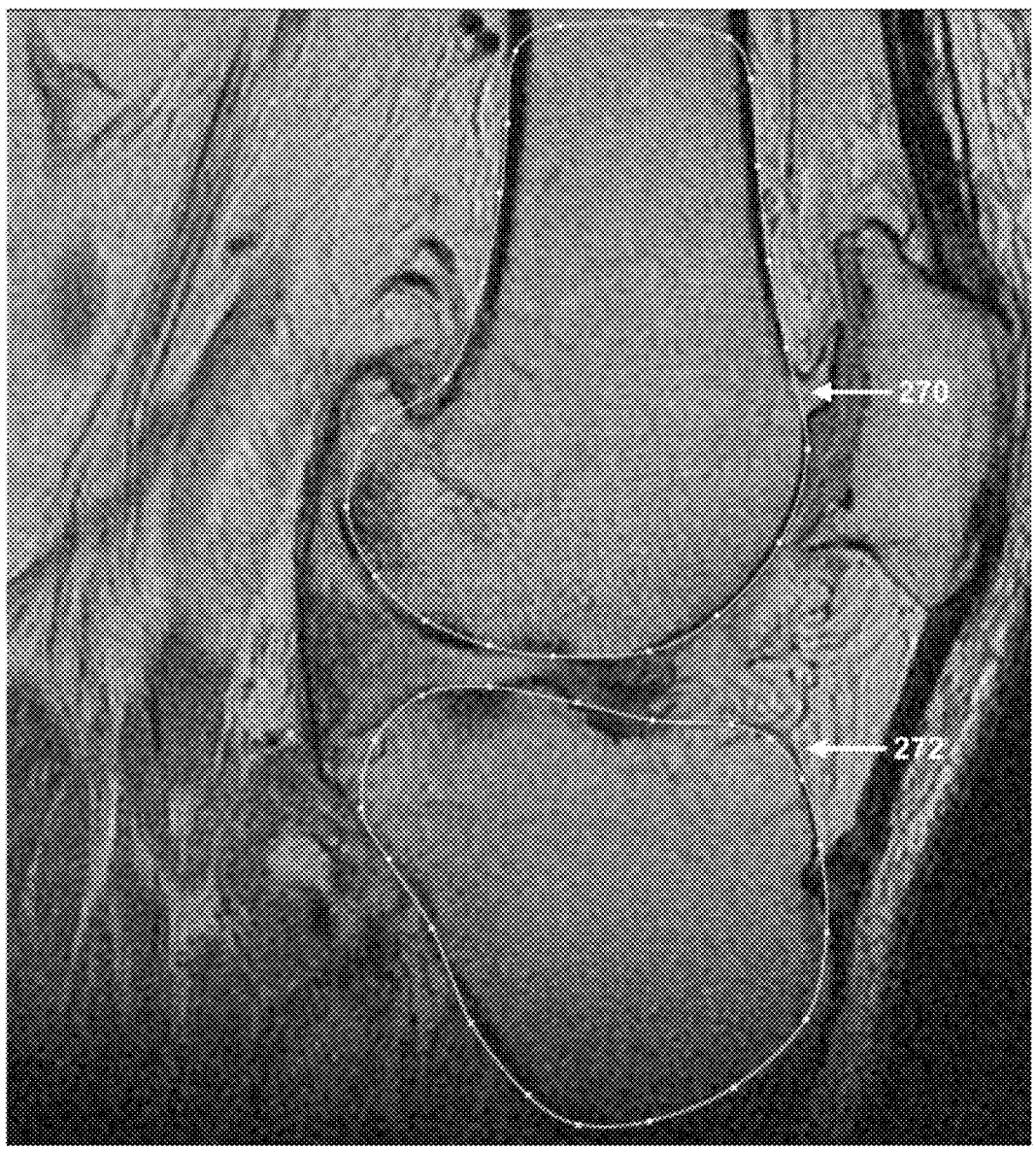
FIG. 7H is another sagittal plane image slice of a segmented femur and tibia.
Figure 7I:
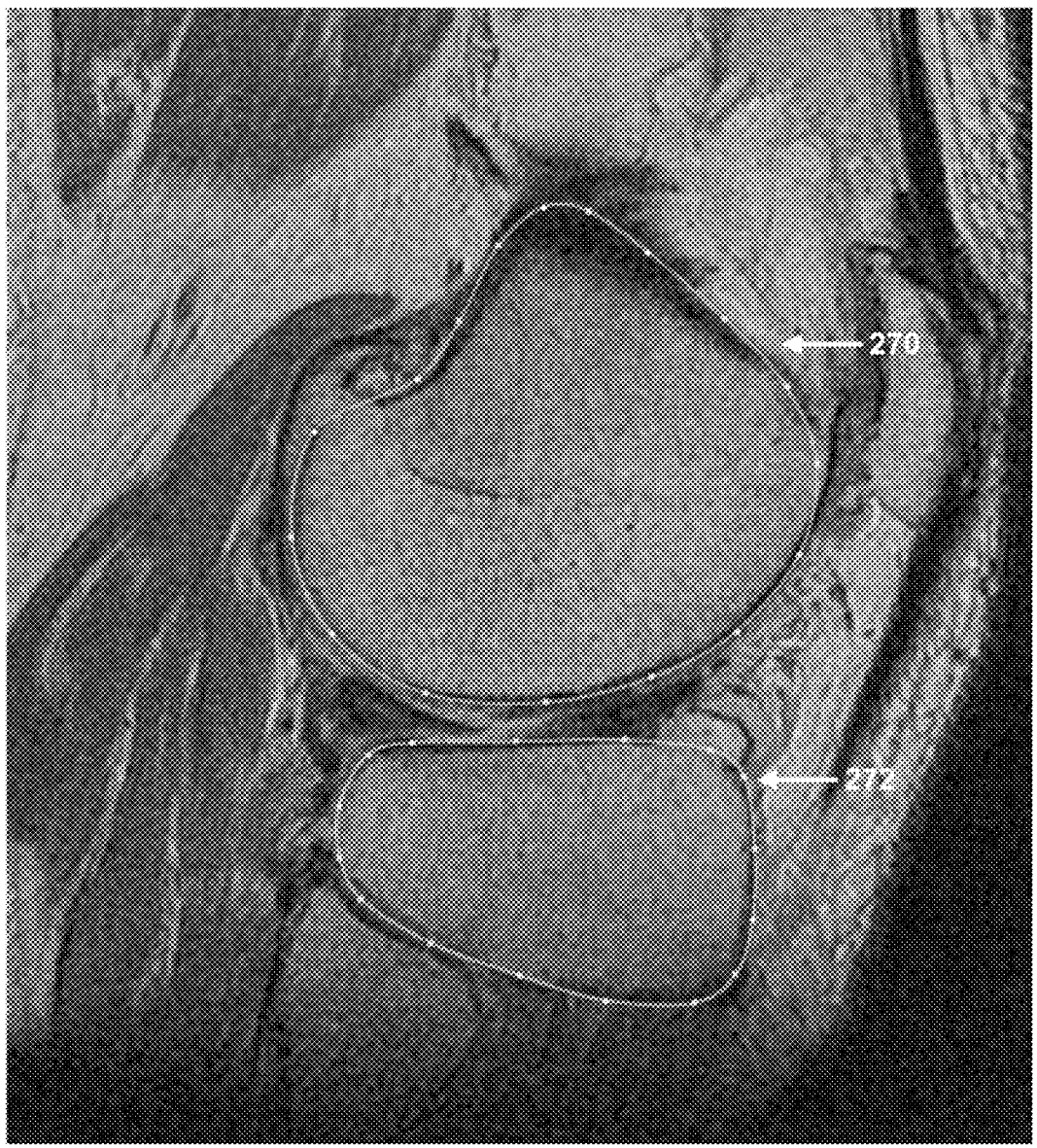
FIG. 7I is another sagittal plane image slice of a segmented femur and tibia.
Figure 7J:
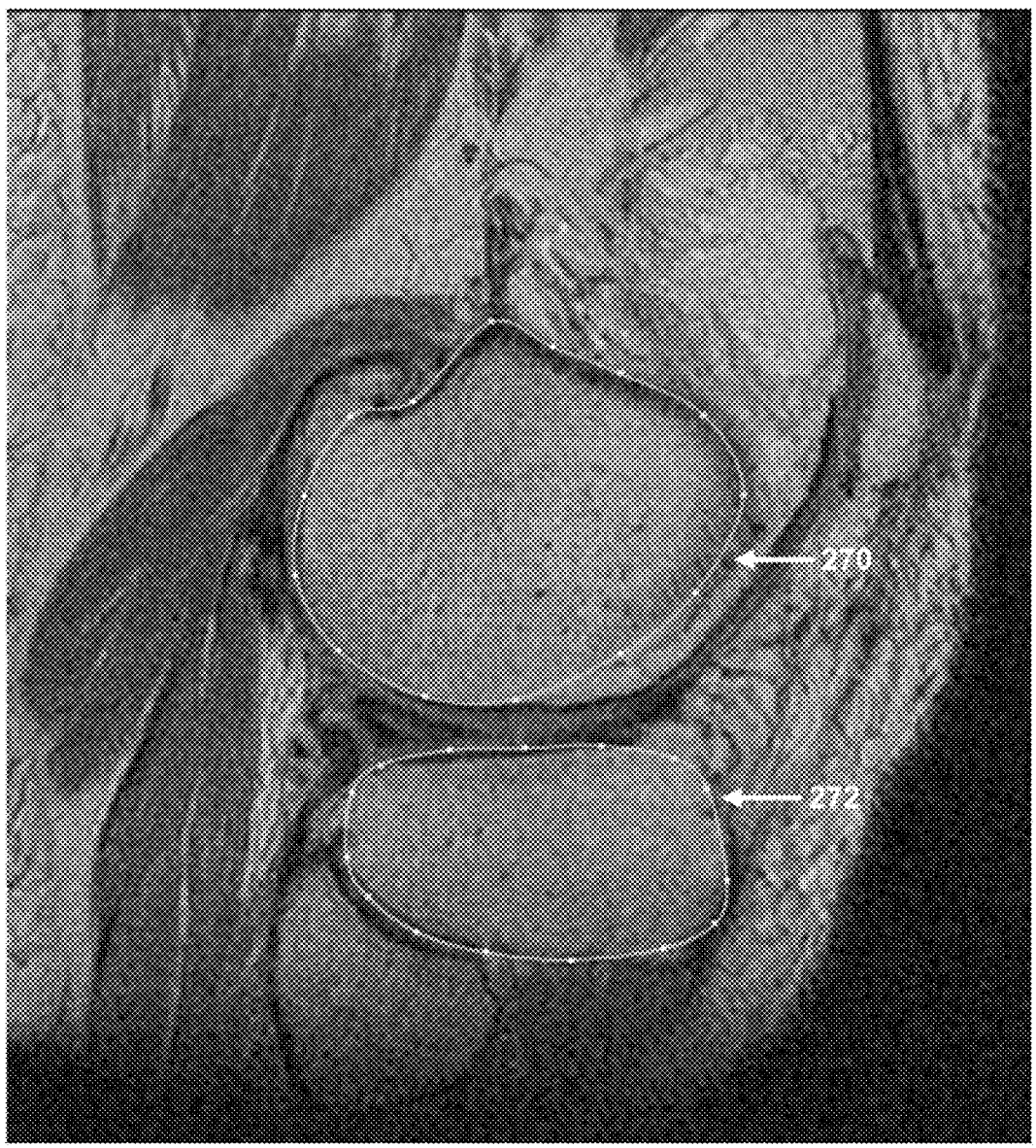
FIG. 7J is another sagittal plane image slice of a segmented femur and tibia.
Figure 7K:
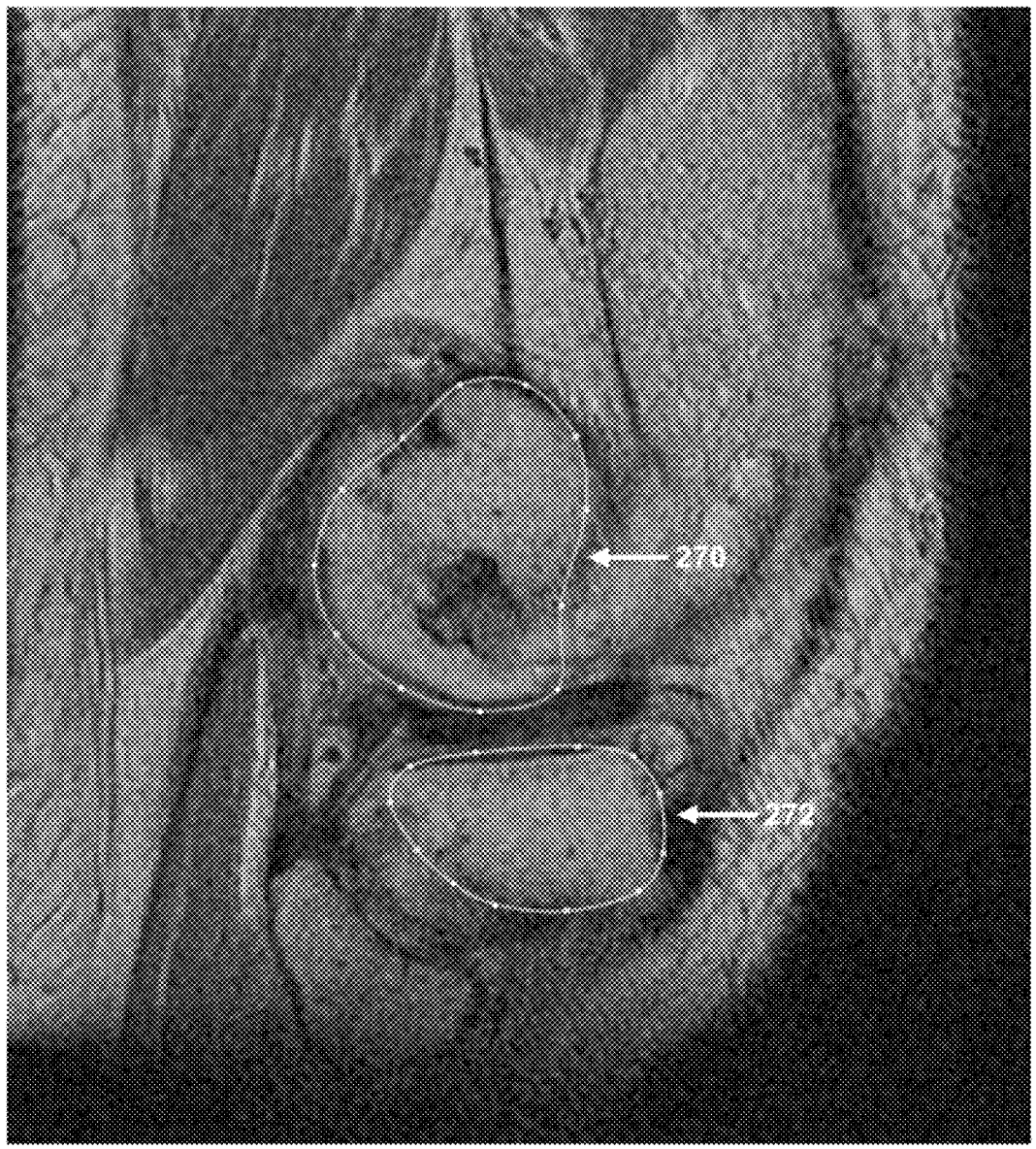
FIG. 7K is another sagittal plane image slice of a segmented femur and tibia.

FIG. 6 depicts a flowchart illustrating one method for automatic or semi-automatic segmentation of Femur and Tibia Planning models of an image modality scan (e.g., an MRI scan) of a patient's knee joint. Initially, operation 250 obtains a scan of the patient's knee joint. In one embodiment, the scan may include about 50 sagittal slices. Other embodiments may use more or fewer slices. Each slice may be a gray scale image having a resolution of 512 by 512 voxels. The scan may represent approximately a 100-millimeter by 150-millimeter by 150-millimeter volume of the patient's knee. While the invention will be described for an MRI scan of a knee joint, this is by way of illustration and not limitation. The invention may be used to segment other types of image modality scans such as computed tomography (CT) scans, ultrasound scans, positron emission tomography (PET) scans, etc., as well as other joints including, but not limited to, hip joints, elbow joints, etc. Further, the resolution of each slice may be higher or lower and the images may be in color rather than gray scale. It is to be appreciated that transversal or coronal slices may be used in other embodiments.

After operation 250 obtains scan data (e.g., scan images 16) generated by imager 8, operation 252 may be performed to segment the femur data of the scan data. During this operation, the femur may be located and spline curves 270 may be generated to outline the femur shape or contour lines in the scan slices, as depicted in FIGS. 7A-7K. It should be appreciated that one or more spline curves may be generated in each slice to outline the femur contour depending on the shape and curvature of the femur as well as the femur orientation relative to the slice direction.

Figure 8:
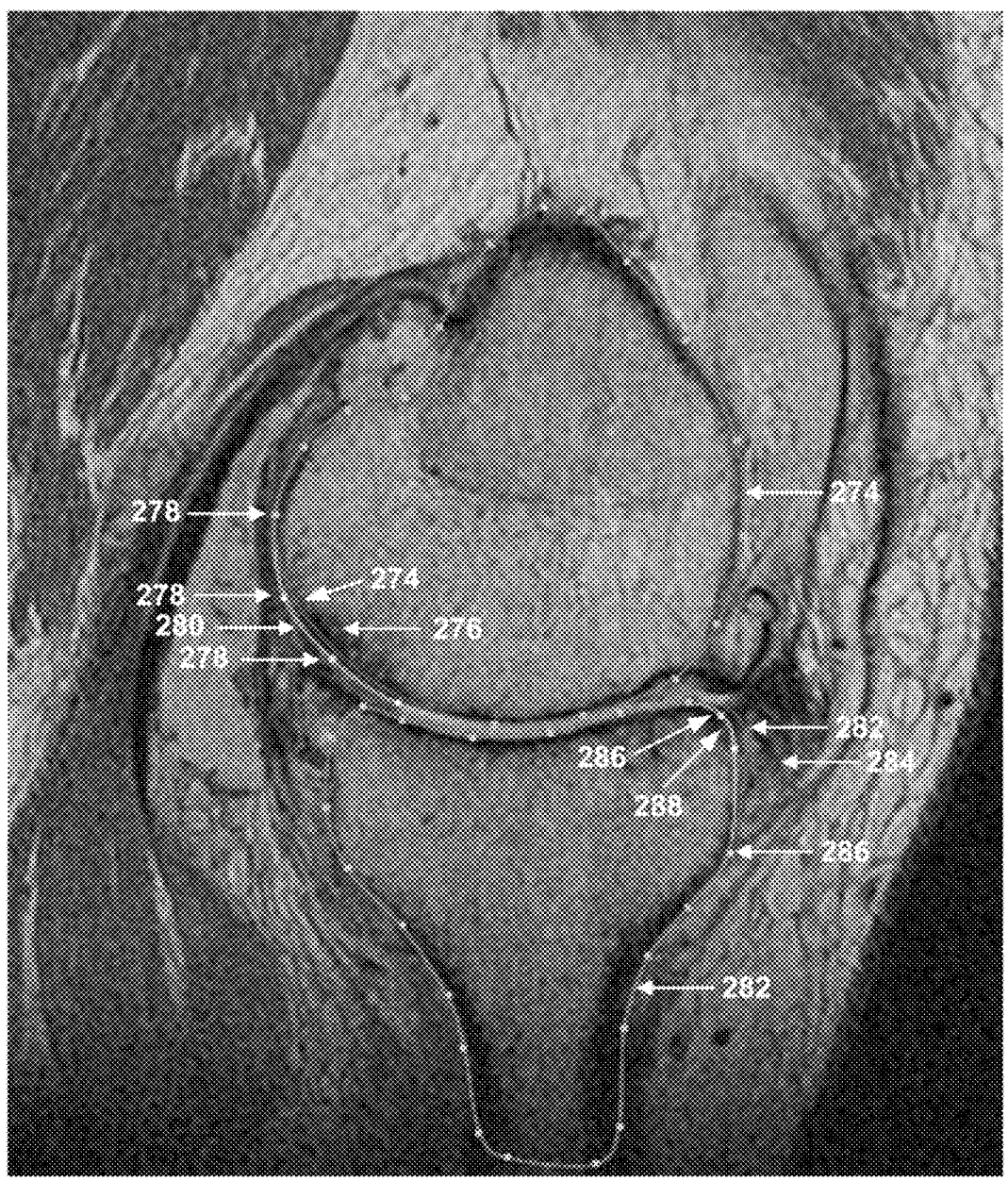
FIG. 8 is a sagittal plane image slice depicting automatically generated slice curves of a femur and a tibia.

Next, in operation 254, a trained technician may verify that the contours of the femur spline curves generated during operation 252 follow the surface of the femur bone. The technician may determine that a spline curve does not follow the bone shape in a particular slice. For example, FIG. 8 depicts an automatically generated femur spline curve 274. The technician may determine that the curve should be enlarged in the lower left part 276 of the femur. There may be various reasons why the technician may decide that the curve needs to be modified. For example, a technician may want to generate a pre-deteriorated bone shape, yet the bone may be worn out in this region and may need reconstruction. The technician may determine this by examining the overall 3D shape of the segmented femur and also by comparing lateral and medial parts of the scan data. The segmented region of the slice may be enlarged by dragging one or more control points 278 located on the spline curve 274 to adjust the curve to more closely follow the femur boundary as determined by the technician, as shown by adjusted curve 280. The number of control points on a spline curve may be dependent on the curve length and curvature variations. Typically, 10-25 control points may be associated with a spline curve for spline modification.

Figure 9:
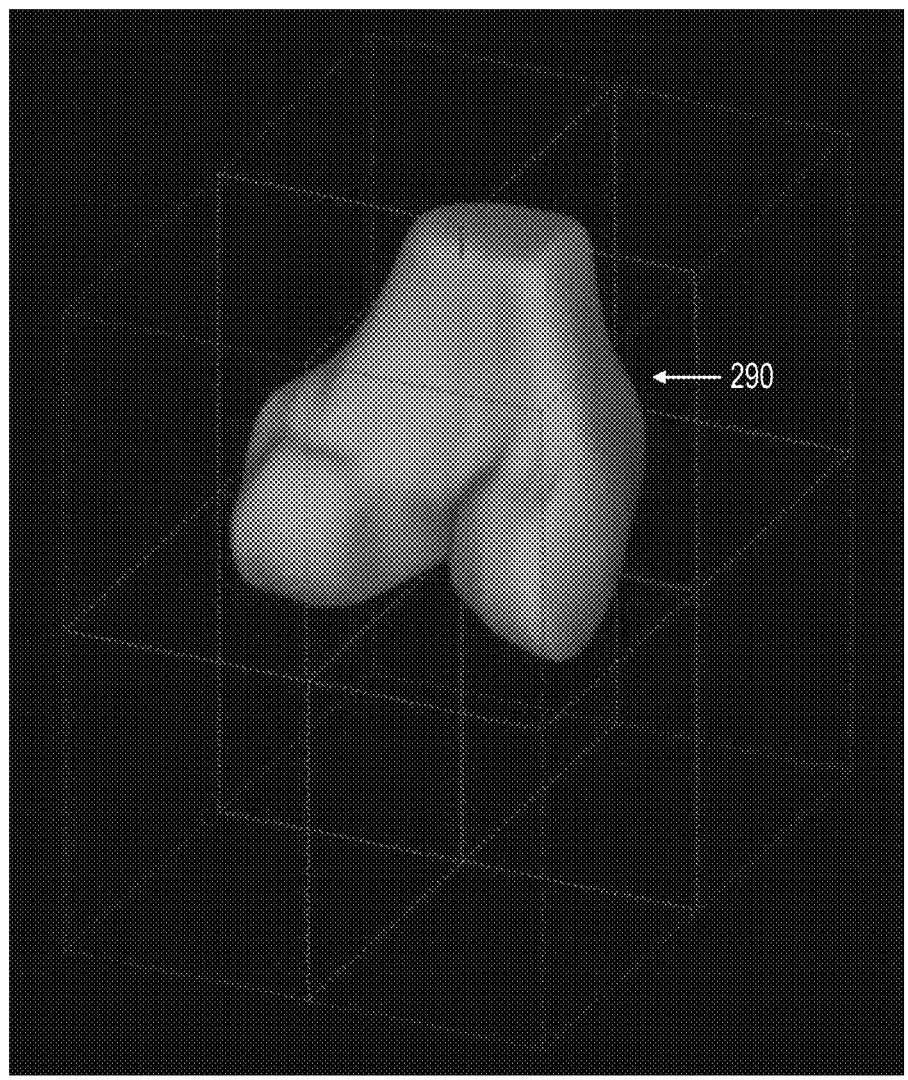
FIG. 9 depicts a 3D mesh geometry of a femur.

Once the technician is satisfied with all of the femur spline curves in the scan slices, operation 256 generates a watertight triangular mesh geometry from the femur segmentation that approximates the 3D surface of the femur. The mesh closely follows the femur spline curves 270 and smoothly interpolates between them to generate a 3D surface model of the femur. FIG. 9 depicts typical 3D mesh geometry 290 of a target femur generated by one embodiment. Such a 3D model may be a 3D surface model or 3D volume model resulting from open-loop contour lines or closed loop contour lines, respectively. In one embodiment, such a 3D model as depicted in FIG. 9 may be a bone model 22 or an arthritic model 36.

After operation 256, operation 258 may be performed to segment the tibia data in the scan data. During this operation, the tibia is located and spline curves may be generated to locate and outline the shape of the tibia found in the scan slices, as depicted by tibia spline curves 272 in FIGS. 7A-7K. It should be appreciated that one or more spline curves may be generated in each slice to outline the tibia depending on the shape and curvature of the tibia as well as the tibia orientation relative to the slice direction.

Next, in operation 260, the technician may verify the tibia spline curves generated during operation 258. The technician may determine that a spline curve does not follow the tibia in a particular slice. For example, referring back to FIG. 8, an automatically generated tibia spline curve 282 is depicted that may not follow the tibia in the right part of the tibia due to the presence of an osteophyte growth 284. The presence of the osteophyte growth 284 may be determined by examining neighboring slices. In this case, the segmented region may be reduced by dragging one or more control points 286 located on the spline curve to modify the tibia spline curve 282 to obtain the adjusted tibia spline curve 288. As previously discussed, each spline curve may have approximately 10-25 control points depending on the length and curvature variation of the spline curve.

When the purpose of the segmentation is generating bone models that will be shown to a surgeon in the images where they are overlapped by implants, a technician will not need to restore the segmentation model to its pre-deteriorated bone shape, and thus will not need to spend time on adjusting splines to follow the pre-deteriorated bone shape. Also there is no need to get highly precise segmentation in the bone areas that are to be replaced with implant. So there is no need to spend time on adjusting the non-perfect curves in the "to be replaced" areas.

Figure 10:
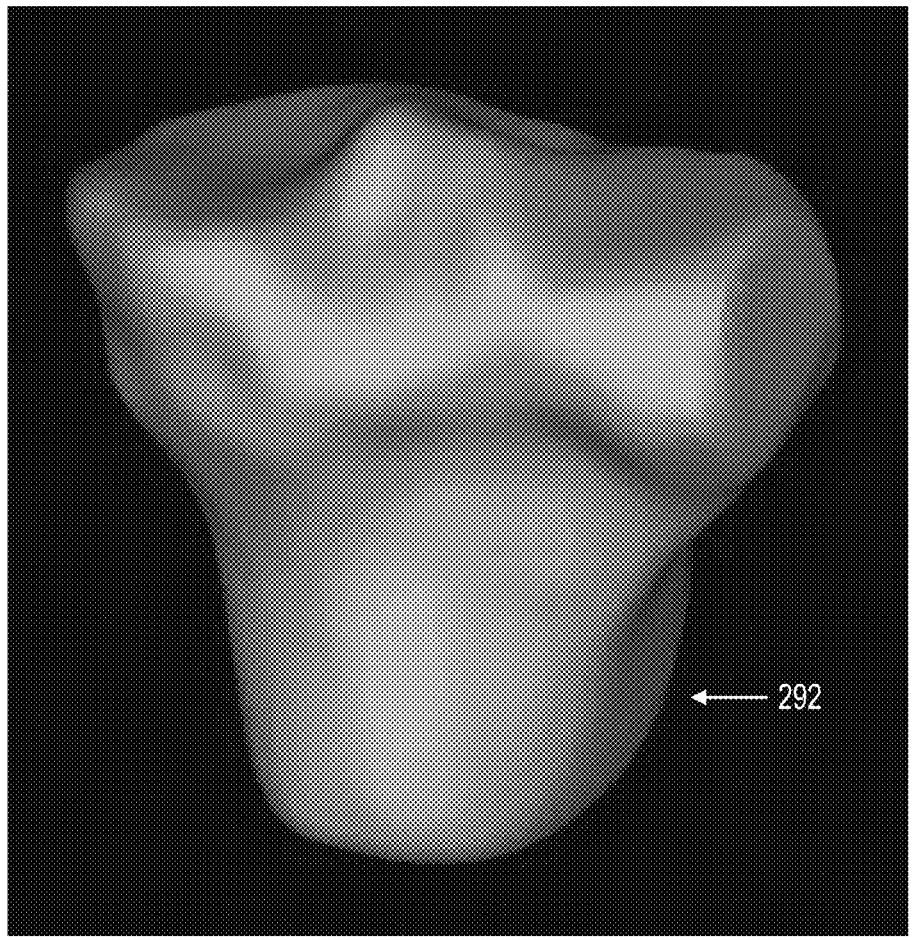
FIG. 10 depicts a 3D mesh geometry of a tibia.

Once the technician is satisfied with all of the tibia spline curves in the scan slices, operation 262 generates a watertight triangular mesh geometry from the tibia segmentation. The mesh closely follows the spline curves and smoothly interpolates between them to generate a 3D surface model of the tibia. FIG. 10 depicts a typical 3D mesh geometry 292 of a target tibia generated by one embodiment. Such a 3D model may be a 3D surface model or 3D volume model resulting from open-loop contour lines or closed loop contour lines, respectively. In one embodiment, such a 3D model as depicted in FIG. 10 may be a bone model 22 or an arthritic model 36.

Because the objects to be located in the scan data typically cannot be segmented by grouping similar voxels into regions, a golden template representative of a typical size and shape of the feature of interest may be employed during the segmentation process to locate the target feature of interest.

Figure 11:
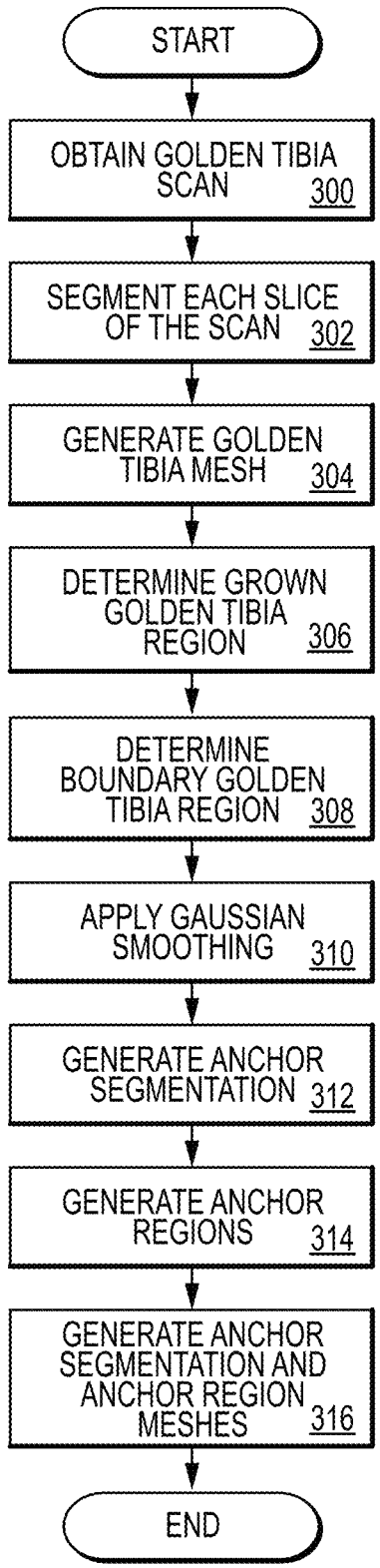
FIG. 11 depicts a flowchart illustrating one method for generating a golden template.

FIG. 11 depicts a flowchart illustrating one method for generating a golden template. The method will be described for generating a golden template of a tibia by way of illustration and not limitation. The method may be used to generate golden templates of other bones including, but not limited to a femur bone, a hip bone, etc.

Initially, operation 300 obtains a scan of a tibia that is not damaged or diseased. The appropriate tibia scan may be chosen by screening multiple MRI tibia scans to locate a MRI tibia scan having a tibia that does not have damaged cancellous and cortical matter (i.e., no damage in tibia regions that will be used as fixed images to locate a corresponding target tibia in a target scan during segmentation), which has good MRI image quality, and which has a relatively average shape, e.g., the shaft width relative to the largest part is not out of proportion (which may be estimated by eye-balling the images). This tibia scan data, referred to herein as a golden tibia scan, may be used to create a golden tibia template. It is to be appreciated that several MRI scans of a tibia (or other bone of interest) may be selected, a template generated for each scan, statistics gathered on the success rate when using each template to segment target MRI scans, and the one with the highest success rate selected as the golden tibia template.

In other embodiments, a catalog of golden models may be generated for any given feature, with distinct variants of the feature depending on various patient attributes, such as (but not limited to) weight, height, race, gender, age, and diagnosed disease condition. The appropriate golden mesh would then be selected for each feature based on a given patient's characteristics.

Figure 12A:
FIG. 12A is a sagittal plane image slice depicting a contour curve outlining a golden tibia region, a contour curve outlining a grown tibia region and a contour curve outlining a boundary golden tibia region.

Then, in operation 302 the tibia is segmented in each scan slice. Each segmentation region includes the cancellous matter 322 and cortical matter 324 of the tibia, but excludes any cartilage matter to form a golden tibia region, outlined by a contour curve 320, as depicted in FIG. 12A.

Figure 13A:
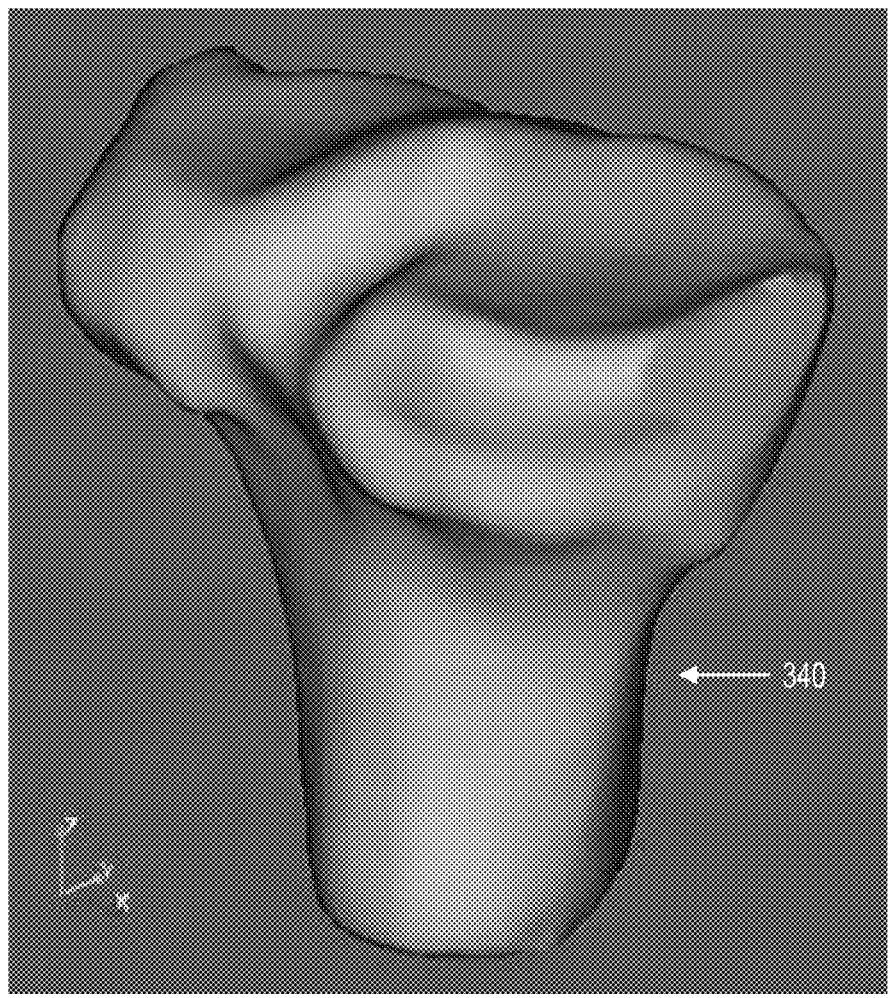
FIG. 13A depicts a golden tibia 3D mesh.

Next, operation 304 generates a golden tibia mesh 340 from the accumulated golden tibia contours of the image slices, as illustrated in FIG. 13A.

Next, operation 306 increases the segmented region in each slice by growing the region to include boundaries between the tibia and adjacent structures where the contact area is generally relatively stable from one MRI scan to another MRI scan. This grown region may be referred to herein as a grown golden tibia region, outlined by contour curve 328, as depicted in FIG. 12A.

The grown golden region may be used to find the surface that separates the hard bone (cancellous and cortical) from the outside matter (cartilage, tendons, water, etc.). The changes in voxel intensities when going from inside the surface to outside of the surface may be used to define the surface. The grown golden region may allow the registration process to find intensity changes in the target scan that are similar to the golden template intensity changes near the surface. Unfortunately, the golden segmentation region does not have stable intensity changes (e.g., near the articular surface) or may not have much of an intensity change. Thus, the grown region typically does not include such regions because they do not provide additional information and may slow down the registration due to an increased number of points to be registered.

Finally, use of a grown golden region may increase the distance where the metric function detects a feature during the registration process. When local optimization is used, the registration may be moved in a particular direction only when a small movement in that direction improves the metric function. When a golden template feature is farther away from the corresponding target bone feature (e.g., when there is a significant shape difference), the metric typically will not move toward that feature. Use of the larger grown region may allow the metric to detect the feature and move toward it.

Next, operation 308 cuts off most of the inner part of the grown golden tibia region to obtain a boundary golden tibia region 330 depicted in FIG. 12A. The boundary golden tibia region 330 is bounded on the inside by contour curve 332 and the outside by contour curve 328.

The boundary region may be used to obtain a more precise registration of the target bone by using the interface from the cancellous bone to the cortical bone. This may be done so that intensity variations in other areas (e.g., intensity variations deep inside the bone) that may move the registration toward wrong features and decrease the precision of locating the hard bone surface are not used during the registration.

Then, operation 310 applies Gaussian smoothing with a standard deviation of two pixels to every slice of the golden tibia scan. In one embodiment, a vtkImageGaussianSmooth filter (part of Visualization Toolkit, a free open source software package) may be used to perform the Gaussian smoothing by setting the parameter "Standard Deviation" to a value of two.

Then, operation 312 generates an anchor segmentation. The anchor segmentation typically follows the original segmentation where the tibia boundary is well defined in most MRI scans. In areas where the tibia boundary may be poorly defined, but where there is another well defined feature close to the tibia boundary, the anchor segmentation may follow that feature instead. For example, in an area where a healthy bone normally has cartilage, a damaged bone may or may not have cartilage. If cartilage is present in this damaged bone region, the bone boundary separates the dark cortical bone from the gray cartilage matter. If cartilage is not present in this area of the damaged bone, there may be white liquid matter next to the dark cortical bone or there may be another dark cortical bone next to the damaged bone area. Thus, the interface from the cortical bone to the outside matter in this region of the damaged bone typically varies from MRI scan to MRI scan. In such areas, the interface between the cortical and the inner cancellous bone may be used. These curves may be smoothly connected together in the remaining tibia areas to obtain the tibia anchor segmentation curve 358, depicted in FIG. 14A.

Figure 14A:
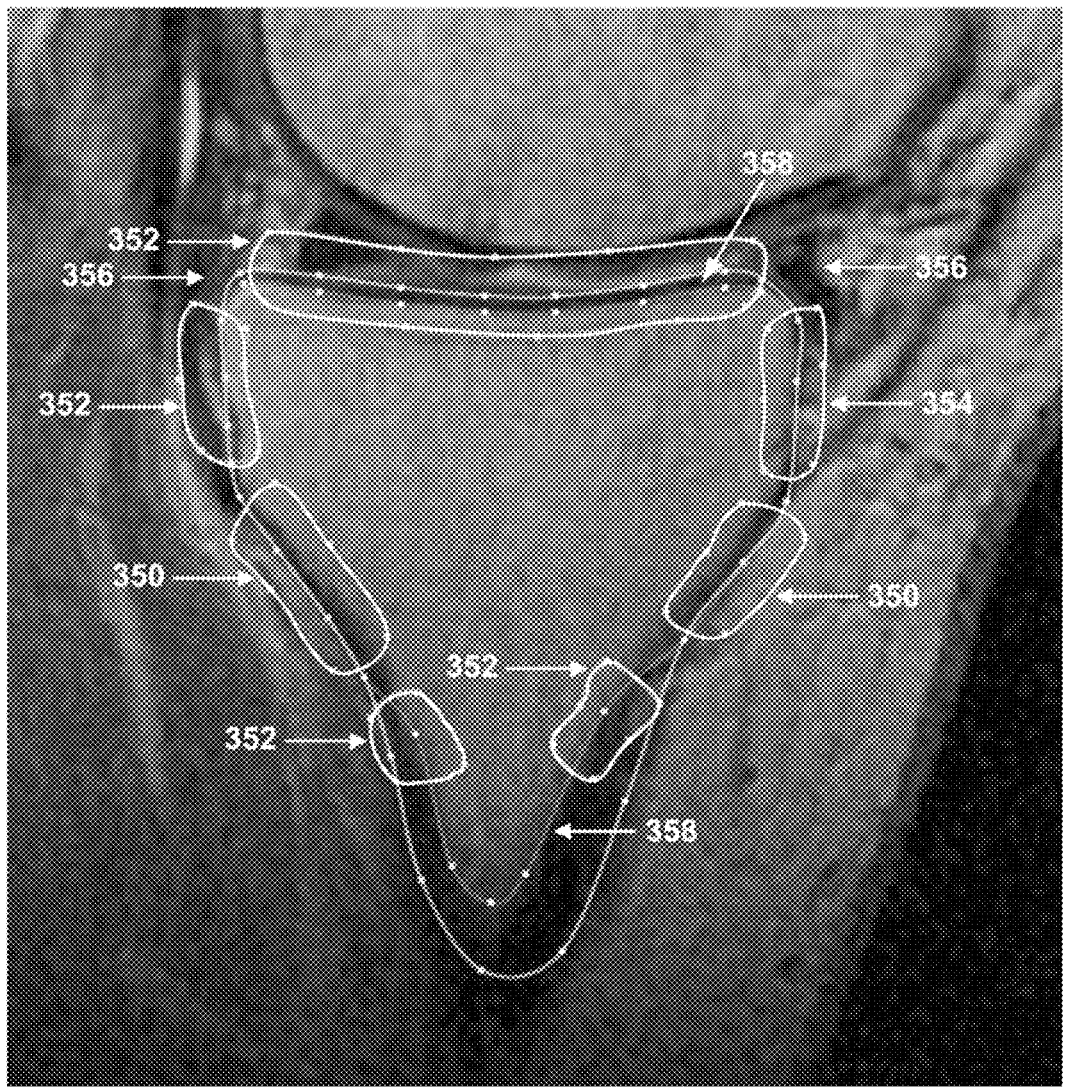
FIG. 14A is a sagittal plane image slice depicting anchor segmentation regions of a tibia.

Then, operation 314 may determine three disjoint regions along the anchor segmentation boundary. Each of these regions is generally well defined in most MRI scans. FIG. 14A depicts these three disjoint regions for a particular image slice. The first region 350, referred to herein as the tibia InDark-OutLight region, depicts a region where the anchor segmentation boundary separates the inside dark intensity cortical matter voxels from the outside light intensity voxels. The second region 352, referred to herein as the tibia InLight-OutDark region, depicts a region where the boundary separates the inside light intensity cancellous matter voxels from the outside dark intensity cortical matter voxels. Finally, region 354, referred to herein as the tibia Dark-in-Light region, depicts a region that has a very thin layer of dark intensity cortical matter voxels along the boundary, but which has light intensity matter voxels away from the boundary (i.e., on both sides of the boundary). Generally, the other regions along the anchor segmentation boundary vary from scan to scan or may not be clear in most of the scans, as depicted by regions 356. Such regions may be an osteophyte growth with an arbitrary shape but which has about the same intensity as the region next to it. Thus, such regions typically are not used as anchor regions in one embodiment of the invention.

Figure 15A:
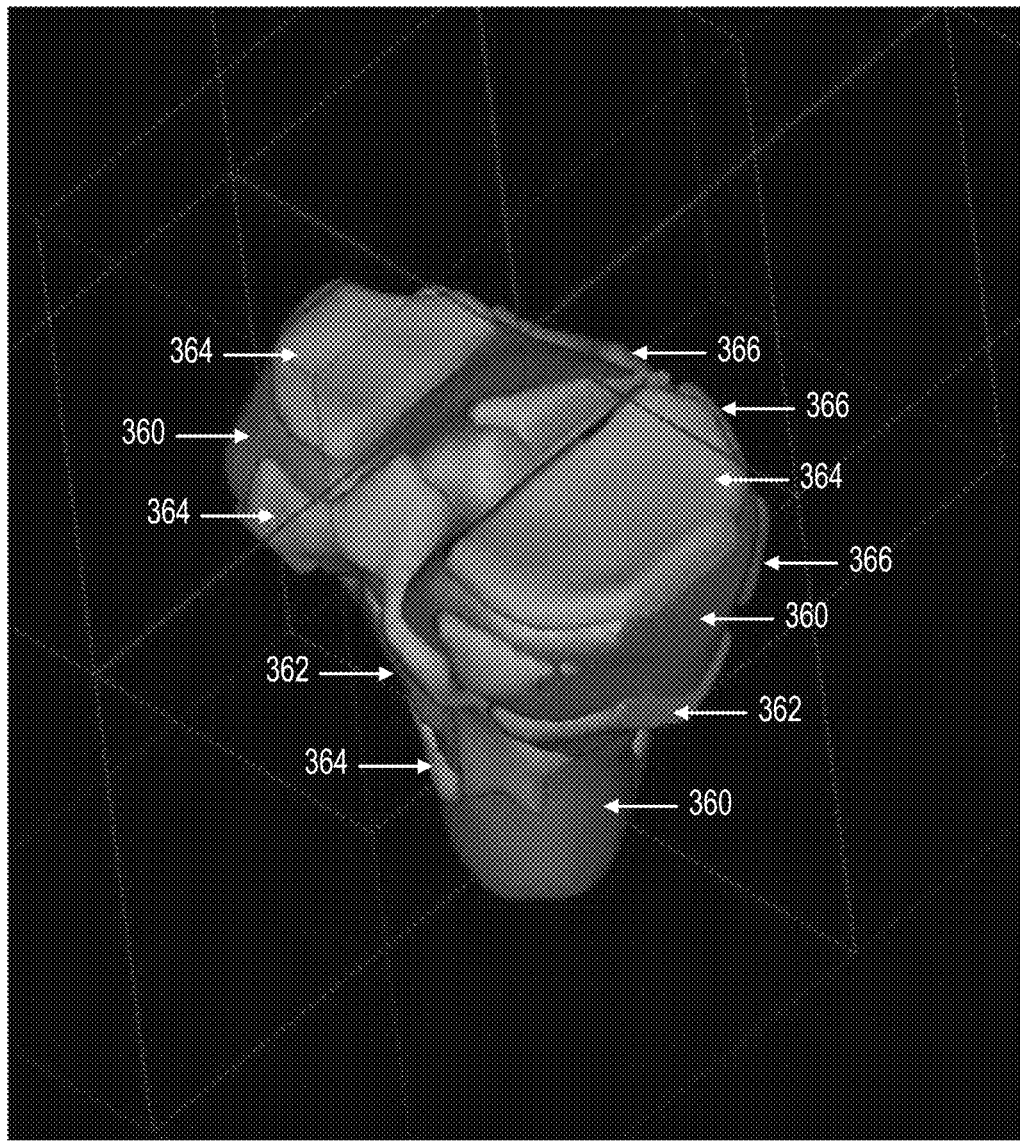
FIG. 15A is a 3D mesh geometry depicting the anchor segmentation mesh, the InDark-OutLight anchor mesh, the InLight-OutDark anchor mesh, and the Dark-In-Light anchor mesh of a tibia.

Finally, operation 316 generates a mesh corresponding to the anchor segmentation and also generates a mesh for each anchor region. FIG. 15A depicts the anchor segmentation mesh 360, the InDark-OutLight anchor region mesh 362, the InLight-OutDark anchor region mesh 364 and the Dark-in-Light anchor region mesh 366 for the tibia. These 3D meshes model the surface of the golden tibia in the specified regions. It is to be appreciated that the 3D meshes are distinct and generally are not combined to create a composite mesh. These meshes may be used to create an artificial fixed image that is used during the registration process as described in more detail below.

Figure 12B:
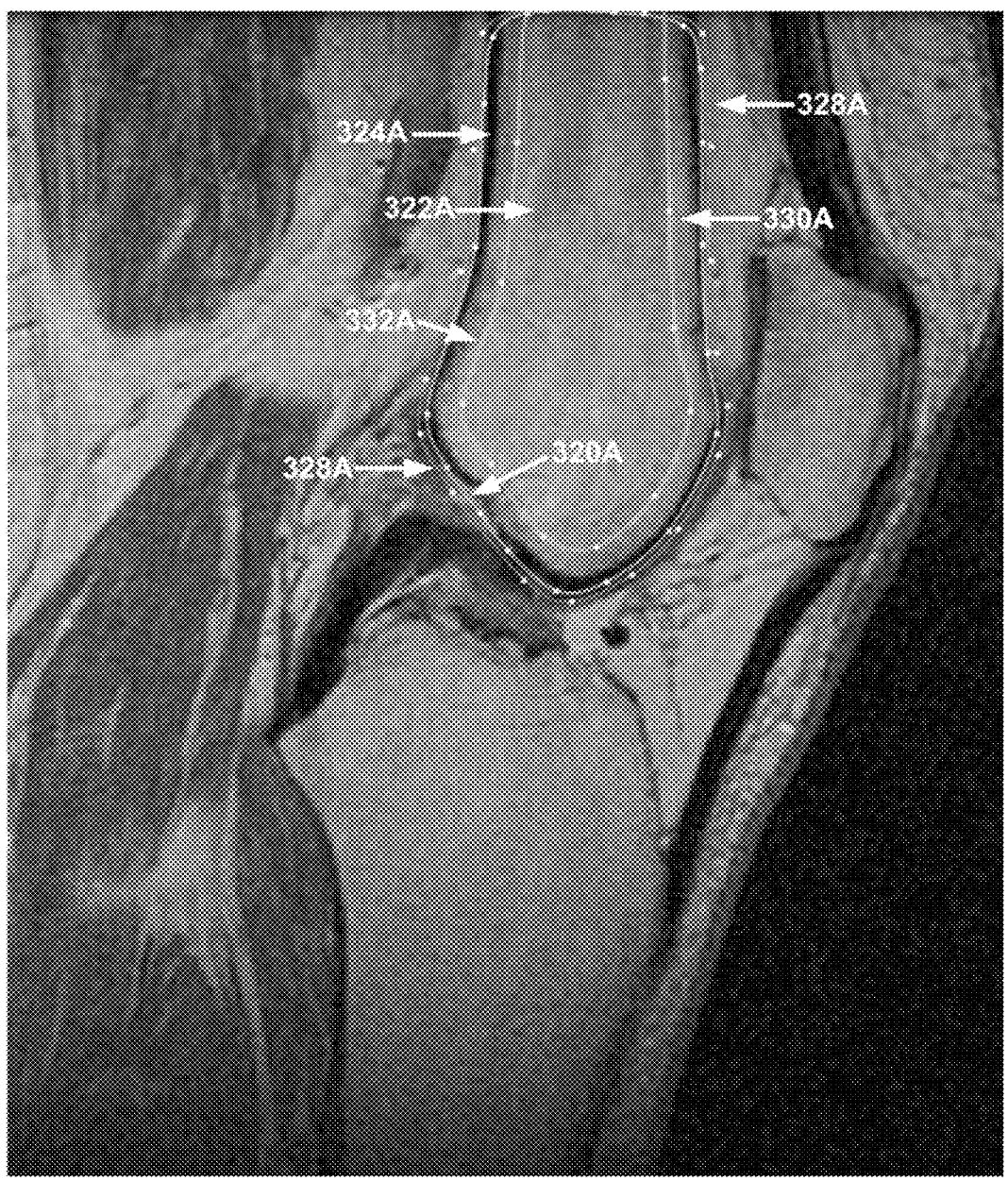
FIG. 12B is a sagittal plane image slice depicting a contour curve outlining a golden femur region, a contour curve outlining a grown femur region and a contour curve outlining a boundary golden femur region.
Figure 13B:
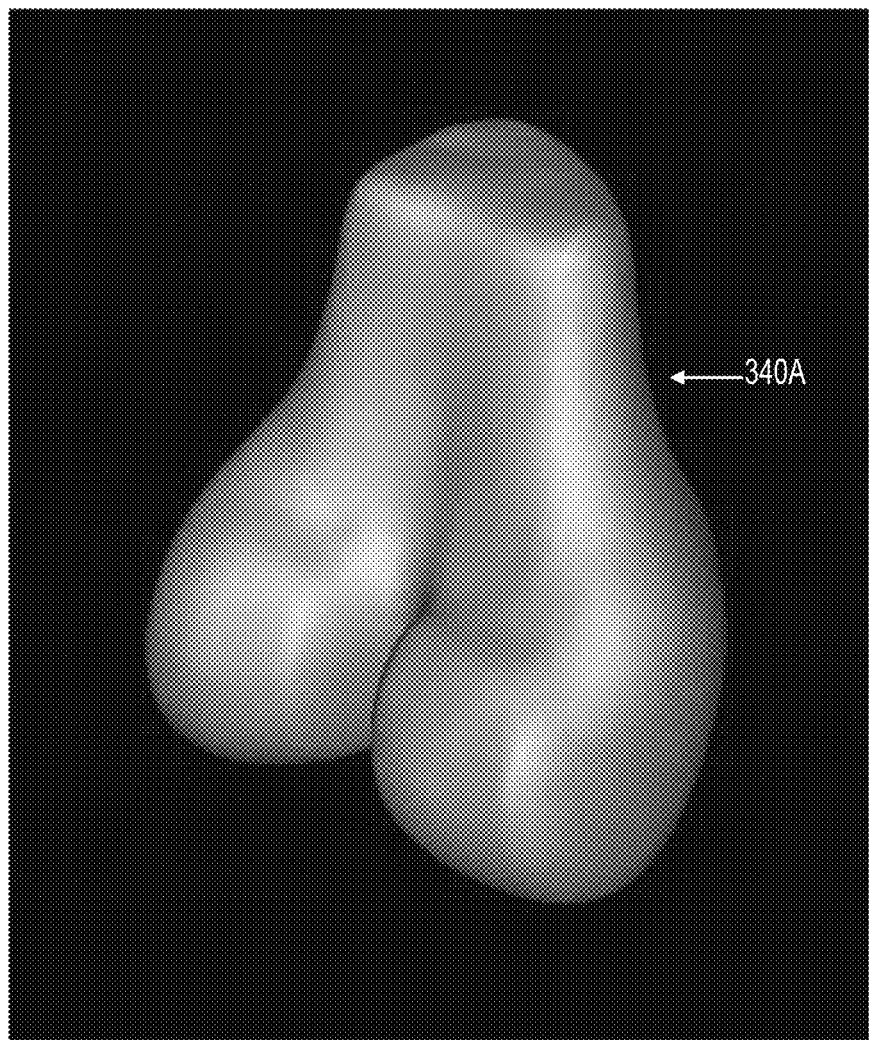
FIG. 13B depicts a golden femur 3D mesh.
Figure 14B:
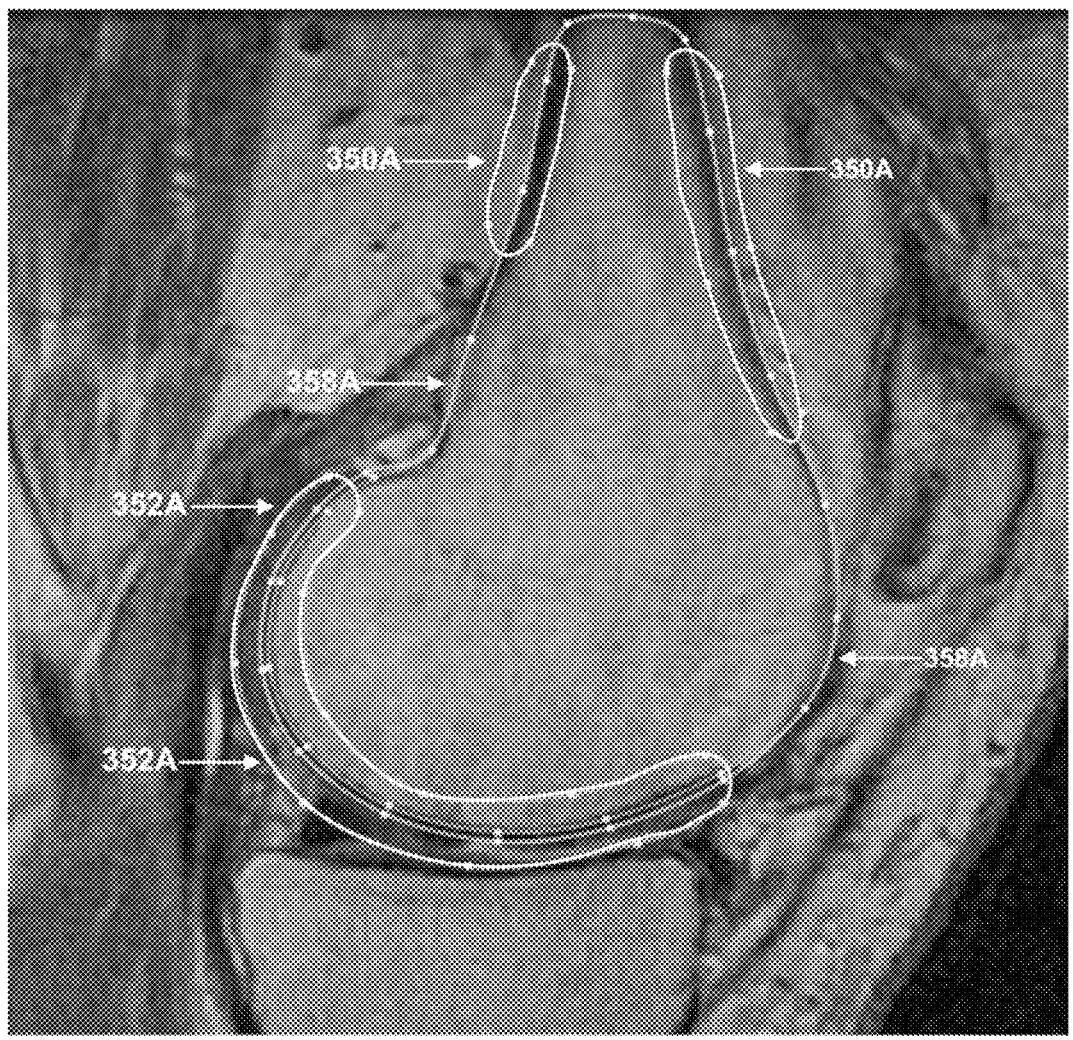
FIG. 14B is a sagittal plane image slice depicting anchor segmentation regions of a femur.
Figure 15B:
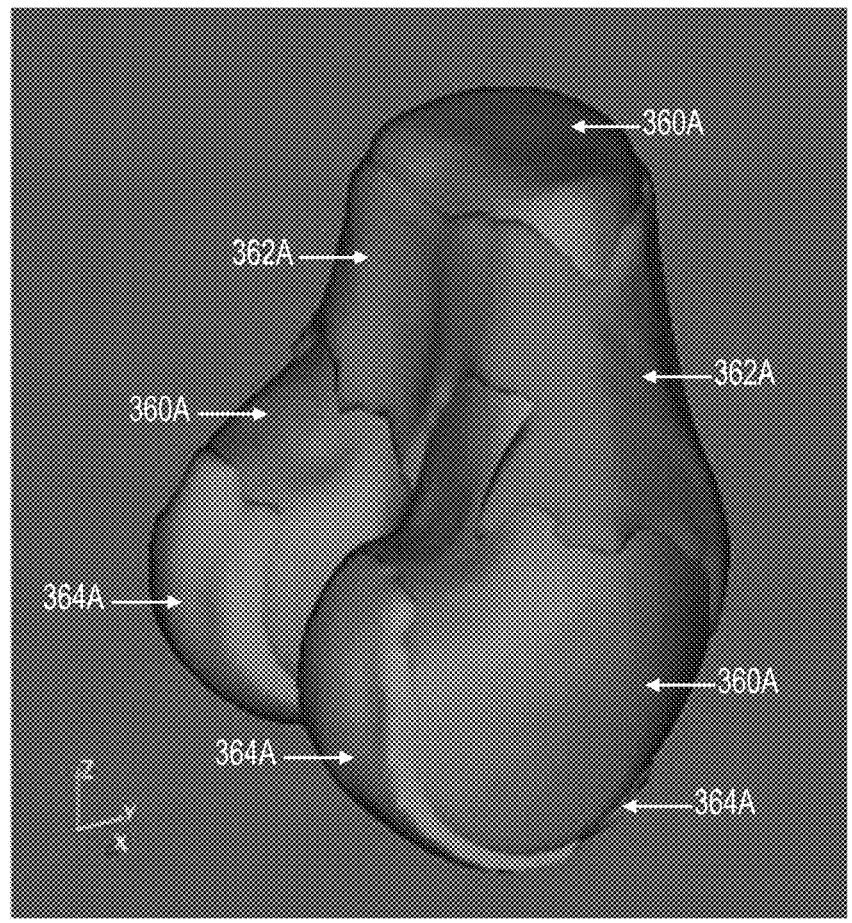
FIG. 15B is a 3D mesh geometry depicting the anchor segmentation mesh, the InDark-OutLight anchor mesh and the InLight-OutDark anchor mesh of a femur.

A golden template of a femur may also be generated in a similar manner using the method depicted by FIG. 11. FIG. 12B depicts the golden femur region, outlined by a contour curve 320A, the grown femur region, outlined by contour curve 328A, and the boundary golden femur region 330A bounded on the inside by contour curve 332A and the outside by contour curve 328A. FIG. 13B depicts the golden femur mesh 340A. FIG. 14B depicts the femur anchor segmentation curve 358A, the femur InDark-OutLight region 350A and the femur InLight-OutDark region 352A. Finally, FIG. 15B depicts the anchor segmentation mesh 360A, the InDark-OutLight anchor region mesh 362A and the InLight-OutDark anchor region mesh 364A for the femur.

Figure 16:
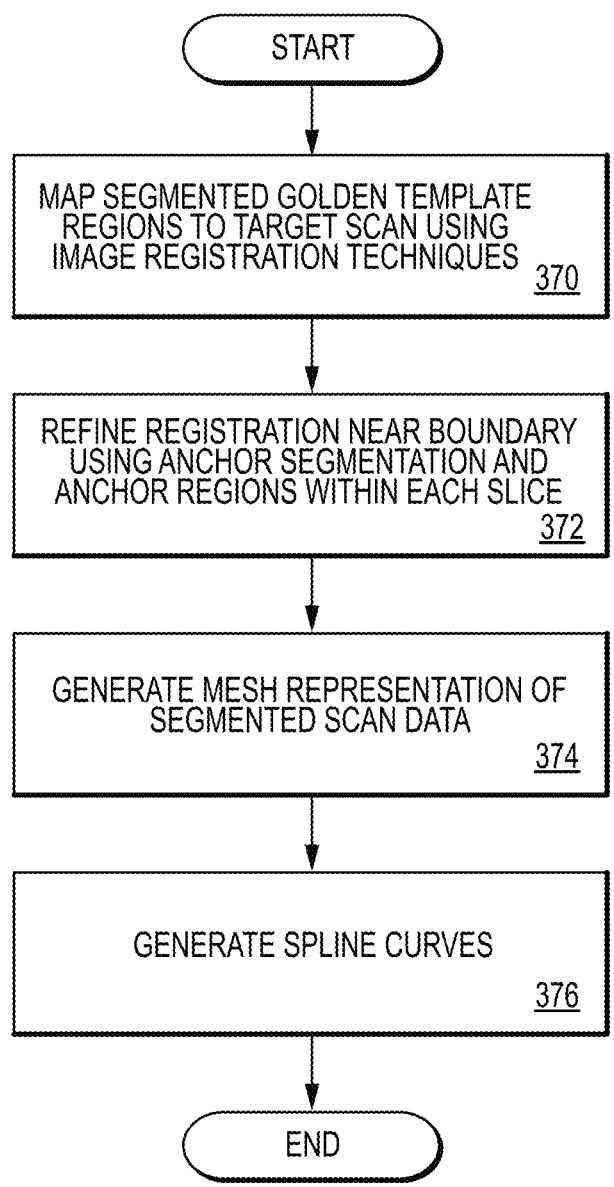
FIG. 16 depicts a flowchart illustrating one method for performing automatic segmentation of scan data using golden template registration.

FIG. 16 depicts a flowchart illustrating one method for performing automatic segmentation (e.g., operation 252 or operation 258 of FIG. 6) of the scan data of a joint (e.g., a MRI scan of a knee joint) using golden template registration. The segmentation method may be used to segment the femur (operation 252 of FIG. 6) and/or the tibia (operation 258 of FIG. 6) in either the left or right knee. Different golden template data may be used to segment the left tibia, right tibia, left femur or right femur. Additionally, other embodiments may segment other joints, including but not limited to, hip joints, elbow joints, by using an appropriate golden template of the feature of interest to be segmented.

Initially, operation 370 maps the segmented 3D golden template and marked regions (e.g., grown and boundary regions) to the target scan data using image registration techniques. This may be done to locate the corresponding feature of interest in the target scan (e.g., a target femur or tibia). Registration transforms the template image coordinate system into the target coordinate system. This allows the template image to be compared and/or integrated with the target image.

Next, operation 372 refines the registration near the feature (e.g., a bone) boundary of interest. Anchor segmentation and anchor regions may be used with a subset of 3D free-form deformations to move points within the plane of the slices (e.g., the yz plane) but not transversal (along the x axis) to the slices. Refinement of the initial registration operation may be necessary to correct errors caused by a high voxel aspect ratio. When a point from a golden template is mapped onto the target scan, it generally maps to a point between adjacent slices of the scan data. For example, if a translation occurs along the x direction, then the point being mapped may only align with a slice when the translation is a multiple of the inter-slice scan distance (e.g., a multiple of two-millimeters for an inter-slice spacing of two-millimeters). Otherwise, the point will be mapped to a point that falls between slices. In such cases, the intensity of the target scan point may be determined by averaging the intensities of corresponding points (voxels) in the two adjacent slices. This may further reduce image resolution. Additionally, refinement of the initial registration operation may correct for errors due to unhealthy areas and/or limited contrast areas. That is, the golden template may be partially pulled away from the actual bone boundary in diseased areas and/or minimal contrast areas (e.g., toward a diseased area having a different contrast) during the initial registration operation.

Next, operation 374 generates a polygon mesh representation of the segmented scan data. A polygon mesh typically is a collection of vertices, edges, and faces that may define the surface of a 3D object. The faces may consist of triangles, quadrilaterals or other simple convex polygons. In one embodiment, a polygon mesh may be generated by applying the registration transform found during operation 372 to all the vertices of a triangle golden template mesh (i.e., the surface of the mesh is composed of triangular faces). It is to be appreciated that the cumulative registration transform typically represents the transform that maps the golden template into the target MRI scan with minimal misalignment error.

Finally, operation 376 generates spline curves that approximate the intersection of the mesh generated by operation 374 with the target MRI slices. Note that these spline curves may be verified by the technician (during operation 254 or operation 260 of FIG. 6).

Figure 17:
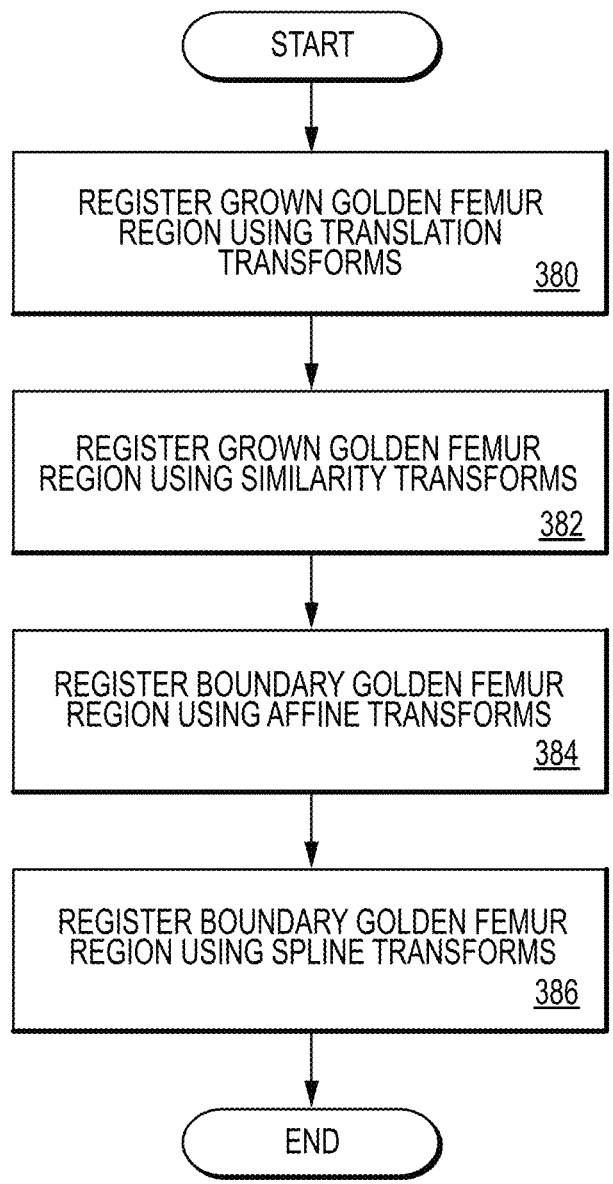
FIG. 17 depicts a flowchart illustrating one method for mapping the segmented golden femur template regions into the target scan data using image registration techniques.

FIG. 17 depicts a flowchart illustrating one method for mapping the segmented golden femur template regions into the target scan using image registration techniques. Registration may be thought of as an optimization problem with a goal of finding a spatial mapping that aligns a fixed image with a target image. Generally several registration operations may be performed, first starting with a coarse image approximation and a low-dimensional transformation group to find a rough approximation of the actual femur location and shape. This may be done to reduce the chance of finding wrong features instead of the femur of interest. For example, if a free-form deformation registration was initially used to register the golden femur template to the target scan data, the template might be registered to the wrong feature, e.g., to a tibia rather than the femur of interest. A coarse registration may also be performed in less time than a fine registration, thereby reducing the overall time required to perform the registration. Once the femur has been approximately located using a coarse registration, finer registration operations may be performed to more accurately determine the femur location and shape. By using the femur approximation determined by the prior registration operation as the initial approximation of the femur in the next registration operation, the next registration operation may find a solution in less time.

Figure 18:
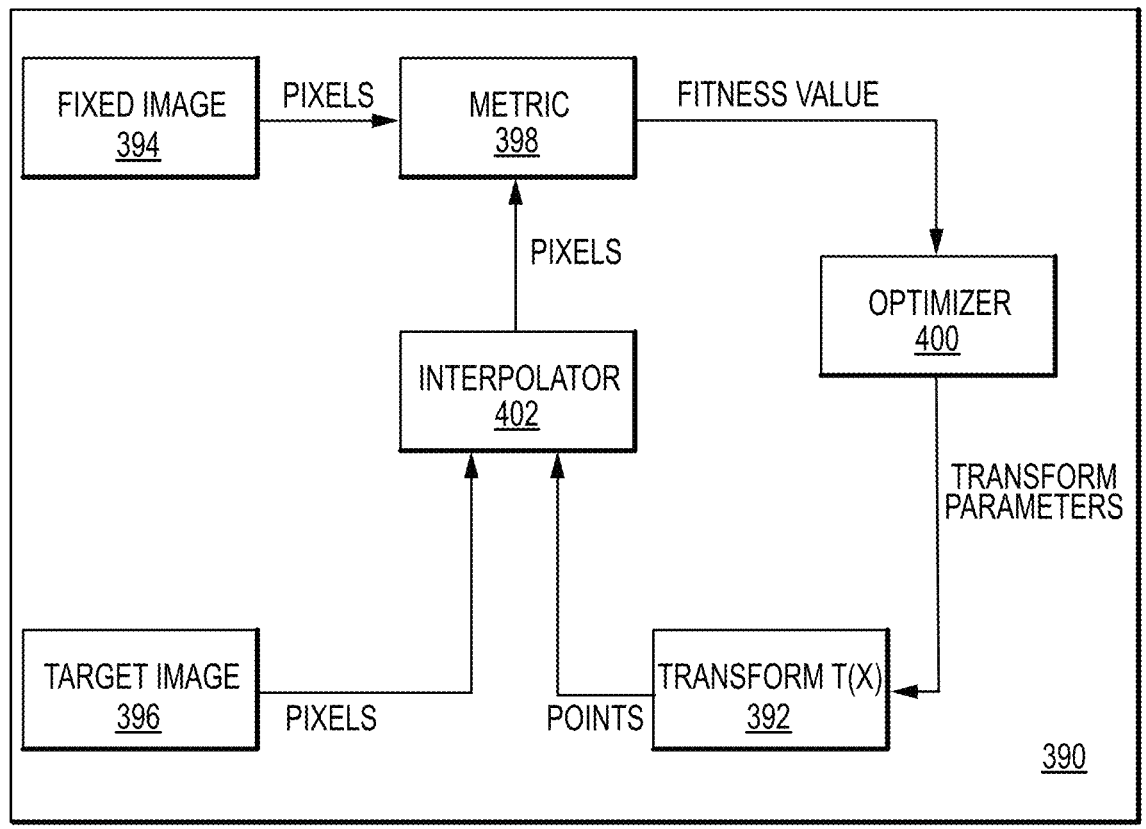
FIG. 18 depicts a registration framework that may be employed by one embodiment.

In one embodiment, each registration operation may employ a registration framework 390 as depicted in FIG. 18. The registration framework 390 may employ an image similarity-based method. Such a method generally includes a transformation model T(X) 392, which may be applied to coordinates of a fixed (or reference) image 394 (e.g., a golden femur template) to locate their corresponding coordinates in a target image 396 space (e.g., a MRI scan), an image similarity metric 398, which quantifies the degree of correspondence between features in both image spaces achieved by a given transformation, and an optimizer 400, which tries to maximize image similarity (or minimize an opposite function) by changing the parameters of the transformation model 392. An interpolator 402 may be used to evaluate target image intensities at non-grid locations (e.g., reference image points that are mapped to target image points that lie between slices). Thus, a registration framework typically includes two input images, a transform, a metric, an interpolator and an optimizer.

Referring again to FIG. 17, operation 380 may approximately register a grown femur region in a MRI scan using a coarse registration transformation. In one embodiment, this may be done by performing an exhaustive translation transform search on the MRI scan data to identify the appropriate translation transform parameters that minimizes translation misalignment of the reference image femur mapped onto the target femur of the target image. This coarse registration operation typically determines an approximate femur position in the MRI scan.

A translational transform, translates (or shifts) all elements of an image by the same 3D vector. That is, the reference femur may be mapped into the target image space by shifting the reference femur along one or more axes in the target image space to minimize misalignment. During this operation the reference femur is not rotated, scaled or deformed. In one embodiment, three parameters for the translation transformation may be generated: one parameter for each dimension that specifies the translation for that dimension. The final parameters of the translation transform minimizing the misalignment of the mapped reference femur image coordinates into the target image space may be stored.

Next, operation 382 further refines the image registration determined by operation 380. This may be done by approximately registering the grown femur region of the reference golden template femur into the target MRI scan data using a similarity transformation. In one embodiment, a similarity transformation may be performed in 3D space. The reference golden femur region may be rotated in 3D, translated in 3D and homogeneously scaled to map its coordinates into the target MRI scan data to minimize misalignment between the reference golden femur region and the corresponding region in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation and three parameters specify a vector that represents the 3D translation in each dimension. A versor is a unit quaternion that provides a convenient mathematical notation for representing orientations and rotations of objects in three dimensions.

In one embodiment, local minimization techniques may be employed with the similarity transformation to obtain a refined registration of the reference golden femur region onto the target MRI scan that is not far from the registration of the reference golden femur region onto the target MRI scan found in the previous operation 190 and used as the initial starting approximation. Registering the grown golden femur region may increase the distance where the metric function detects a feature during the registration process. When local optimization is used, the registration may be moved in a particular direction only when a small movement in that direction improves the metric function. When a golden femur template feature is farther away from the corresponding target femur feature (e.g., when there is a significant shape difference), the metric typically will not move toward that feature. Use of the larger grown femur region may allow the metric to detect the feature and move toward it.

After operation 382, operation 384 further refines the image registration of the golden femur into the target scan. In one embodiment, an affine transformation may be used to register coordinates of a boundary golden femur region of a golden femur template into the target MRI scan data. In one embodiment, the approximate femur registration found during operation 382 may be used as the initial starting approximation for the affine transformation.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the boundary golden femur region mapped into the target MRI scan data may be stored.

Finally, operation 386 further refines the image registration of the boundary golden femur region. In one embodiment, a spline transformation may be used to register the coordinates of the boundary golden femur region into the MRI scan data (target image space). In one embodiment, a 3D B-Spline deformable transformation may be employed and the transformation found in operation 384 may be used as the initial transformation values for the 3D B-Spline deformable transformation.

A B-Spline deformable transformation typically is a free form deformation of an object using a deformation field where a deformation vector is assigned to every point in space. For example, a 3D B-spline deformable transform T may specify a 3D vector V(P) for every point P in the original 3D space that is moved by T such that T:P→P+V (P).

In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of the vectors may be modeled using B-splines. Typically a grid J×K×L of control points may be specified where J, K, and L are parameters of the transformation.

In one embodiment, splines of order three may be used with a grid 9×6×6 of control points. That is, the transformation employs nine control points in the medial/lateral direction (i.e., the x direction), and six control points in the other directions (i.e., y and z directions). Two control points in each dimension (i.e., 2 of 9 in the x direction, 2 of 6 in the y direction and 2 of 6 in the z direction) may be used to specify boundary conditions. As such, the inner spline nodes may form a grid of size 7 by 4 by 4 and the boundary conditions increase the grid to size 9 by 6 by 6. The parametric set for this transformation has a dimension of 3×9×6×6=972 (i.e., each dimension may have a 9×6×6 grid of control points). The final parameters of the spline transformation that minimizes the misalignment between the reference golden femur template and the target MRI scan data may be stored. This may be referred to as the cumulative femur registration transform herein.

Figure 19:
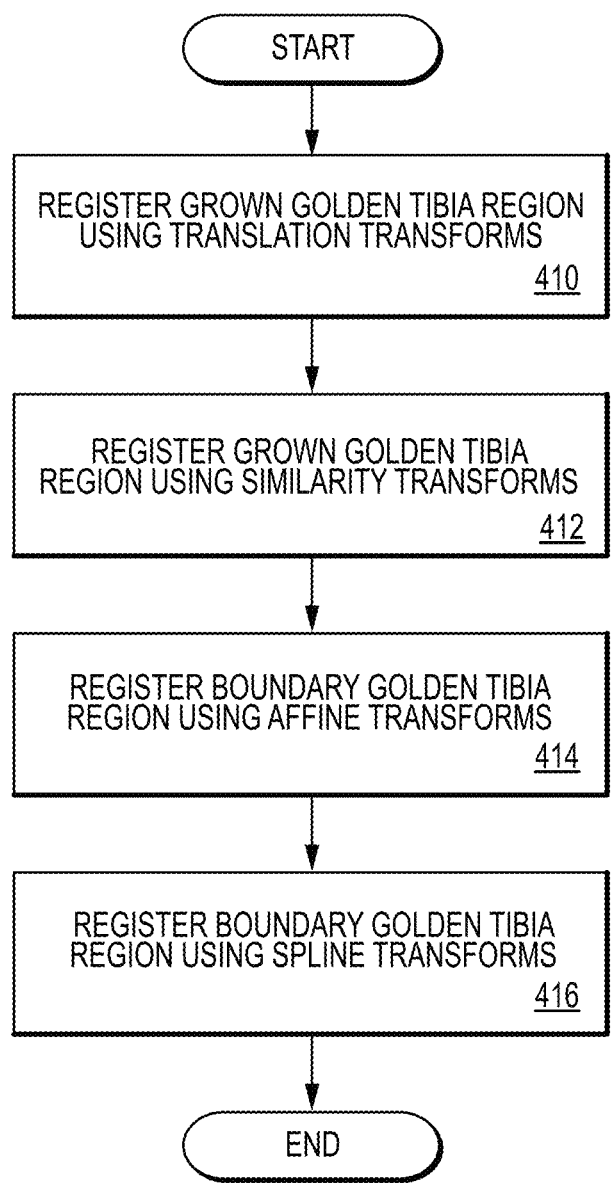
FIG. 19 depicts a flowchart illustrating one method for mapping the segmented golden tibia template regions into the target scan data using image registration techniques.

FIG. 19 depicts a flowchart illustrating one method for mapping the segmented golden tibia template regions into the target scan using image registration techniques. Generally several registration operations may be performed, first starting with a coarse image approximation and a low-dimensional transformation group to find a rough approximation of the actual tibia location and shape. This may be done to reduce the chance of finding wrong features instead of the tibia of interest. For example, if a free-form deformation registration was initially used to register the golden tibia template to the target scan data, the template might be registered to the wrong feature, e.g., to a femur rather than the tibia of interest. A coarse registration may also be performed in less time than a fine registration, thereby reducing the overall time required to perform the registration. Once the tibia has been approximately located using a coarse registration, finer registration operations may be performed to more accurately determine the tibia location and shape. By using the tibia approximation determined by the prior registration operation as the initial approximation of the tibia in the next registration operation, the next registration operation may find a solution in less time.

In one embodiment, each registration operation may employ a registration framework 390 as depicted in FIG. 18.

The registration framework 390 may employ an image similarity-based method. Such a method generally includes a transformation model T(X) 392, which may be applied to coordinates of a fixed (or reference) image 394 (e.g., a golden tibia template) to locate their corresponding coordinates in a target image 396 space (e.g., a MRI scan), an image similarity metric 398, which quantifies the degree of correspondence between features in both image spaces achieved by a given transformation, and an optimizer 400, which tries to maximize image similarity by changing the parameters of the transformation model 392. An interpolator 402 may be used to evaluate target image intensities at non-grid locations (i.e., reference image points that are mapped to target image points that lie between slices). Thus, a registration framework typically includes two input images, a transform, a metric, an interpolator and an optimizer.

The automatic segmentation registration process will be described using scan data that includes a right tibia bone. This is by way of illustration and not limitation. Referring again to FIG. 19, operation 410 may approximately register a grown tibia region in a MRI scan using a coarse registration transformation. In one embodiment, this may be done by performing an exhaustive translation transform search on the MRI scan data to identify the appropriate translation transform parameters that minimizes translation misalignment of the reference image tibia mapped onto the target tibia of the target image. This coarse registration operation typically determines an approximate tibia position in the MRI scan. During this operation, the tibia of the reference image may be overlapped with the target tibia of the target image using a translation transformation to minimize translational misalignment of the tibias.

A translational transform, translates (or shifts) an image by the same 3D vector. That is, the reference tibia may be mapped into the target image space by shifting the reference tibia along one or more axes in the target image space to minimize misalignment. During this operation the reference tibia is not rotated, scaled or deformed. In one embodiment, three parameters for the translation transformation may be generated, one parameter for each dimension that specifies the translation for that dimension. The final parameters of the translation transform minimizing the misalignment of the mapped reference tibia image coordinates into the target image space may be stored.

Next, operation 412 further refines the image registration determined by operation 410. This may be done by approximately registering the grown tibia region of the reference golden tibia template into the target MRI scan data using a similarity transformation. In one embodiment, a similarity transformation may be performed in 3D space. The reference golden tibia region may be rotated in 3D, translated in 3D and homogeneously scaled to map its coordinates into the target MRI scan data to minimize misalignment between the reference golden tibia region and the corresponding region in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation and three parameters specify a vector that represents the 3D translation in each dimension. A versor is a unit quaternion that provides a convenient mathematical notation for representing orientations and rotations of objects in three dimensions.

In one embodiment, local minimization techniques may be employed with the similarity transformation to obtain a refined registration of the reference golden tibia region onto the target MRI scan that is not far from the registration of the reference golden tibia region onto the target MRI scan found in the previous operation 410 and used as the initial starting approximation. Registering the grown golden tibia region may increase the distance where the metric function detects a feature during the registration process. When local optimization is used, the registration may be moved in a particular direction only when a small movement in that direction improves the metric function. When a golden tibia template feature is farther away from the corresponding target tibia feature (e.g., when there is a significant shape difference), the metric typically will not move toward that feature. Use of the larger grown tibia region may allow the metric to detect the feature and move toward it.

After operation 412, operation 414 further refines the image registration. In one embodiment, an affine transformation may be used to register coordinates of a boundary golden tibia region of a golden tibia template into the target MRI scan data. In one embodiment, the approximate tibia registration found during operation 412 may be used as the initial starting approximation for the affine transformation.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the boundary golden tibia region mapped into the target MRI scan data may be stored.

Finally, operation 416 further refines the image registration of the boundary golden tibia region. In one embodiment, a spline transformation may be used to register the coordinates of the boundary golden tibia region into the MRI scan data (target image space). In one embodiment, a 3D B-Spline deformable transformation may be employed and the transformation found in operation 414 may be used as the initial transformation values for the 3D B-Spline deformable transformation.

A B-Spline deformable transformation typically is a free form deformation of an object using a deformation field where a deformation vector is assigned to every point in space. In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of the vectors may be modeled using B-splines. Typically a grid J×K×L of control points may be specified where J, K, and L are parameters of the transformation.

In one embodiment, splines of order three may be used with a grid 9×6×6 of control points. That is, the transformation employs nine control points in the medial/lateral direction (i.e., the x direction, and six control points in the other directions (i.e., the y and z directions). Two control points in each dimension (i.e., 2 of 9 in the x direction, 2 of 6 in the y direction and 2 of 6 in the z direction) may be used to specify boundary conditions. As such, the inner spline nodes may form a grid of size 7 by 4 by 4 and the boundary conditions increase the grid to size 9 by 6 by 6. The parametric set for this transformation has a dimension of 3×9×6×6=972. The final parameters of the spline transformation that minimizes the misalignment between the reference golden tibia template and the target MRI scan data may be stored. This may be referred to as the cumulative tibia registration transform herein.

The shape of the tibia may vary more from patient to patient than does the shape of the femur. As a result, the affine transformation may not provide a close enough registration of the golden tibia template to the target tibia in the target scan. This may cause the Spline transformation to find a local optimum that may be far from the actual tibia in some areas. In one embodiment, an additional registration operation between the affine transform and spline transform operations may be performed to more closely align the golden tibia and the target tibia, allowing the spline transform to converge to the correct local optimum rather than a nearby (but wrong) local optimum.

The class of transforms utilized generally should allow more flexibility (or degrees of freedom) than the Affine transform and less flexibility than the B-spline transforms. The number of degrees of freedom generally is equal to the number of transform parameters. In one embodiment, a class of transforms with more than 12 parameters and less than 3×9×6×6 parameters may be used. For example, a B-spline transform with fewer control points (than used in the subsequent spline transform) may be used for the additional transform operation. Alternatively, the deformations may be modeled using quadric rather than cubic functions.

In another embodiment, several golden tibia templates may be used that represent typical tibia variations, e.g., golden tibia templates for varum, valgum and normal tibia. In one embodiment, each of the golden tibia templates may be used during the translation, similarity and affine transform registration operations to find the template that provides the best match (e.g., best correlation) in the affine transform registration operation. This template may then be used in the remaining registration operations.

Finally, in one embodiment, the tibia registration may be improved by performing the tibia segmentation after the femur segmentation and adding a restriction on the tibia registration transformations such that the tibia may not penetrate the femur. In one embodiment, this may be implemented by introducing a penalty for the penetration. In the target MRI all the voxels that lie inside the femur splines may be marked. The metric functions, described in more detail below, that are used in the registration operations may be modified to include a penalty term. The penalty term may be computed by selecting a set of points on the boundary of the golden template segmentation, applying a transform to the set of points (in a similar way as the transform is applied to the sample points used in the correlation computations), determining if a transformed sample point falls into any of the marked voxels, and adding a large value to the penalty term for each transformed sample point that falls into any of the marked voxels.

In each of the above registration operations, a metric may be used to quantify the degree of correspondence between features in both the reference image and target image achieved by a given transformation. In one embodiment, the metric quantitatively measures how well the transformed golden template image fits the target image (e.g., a target MRI scan) and may compare the gray-scale intensity of the images using a set of sample points in the golden template region to be registered.

Figure 20:
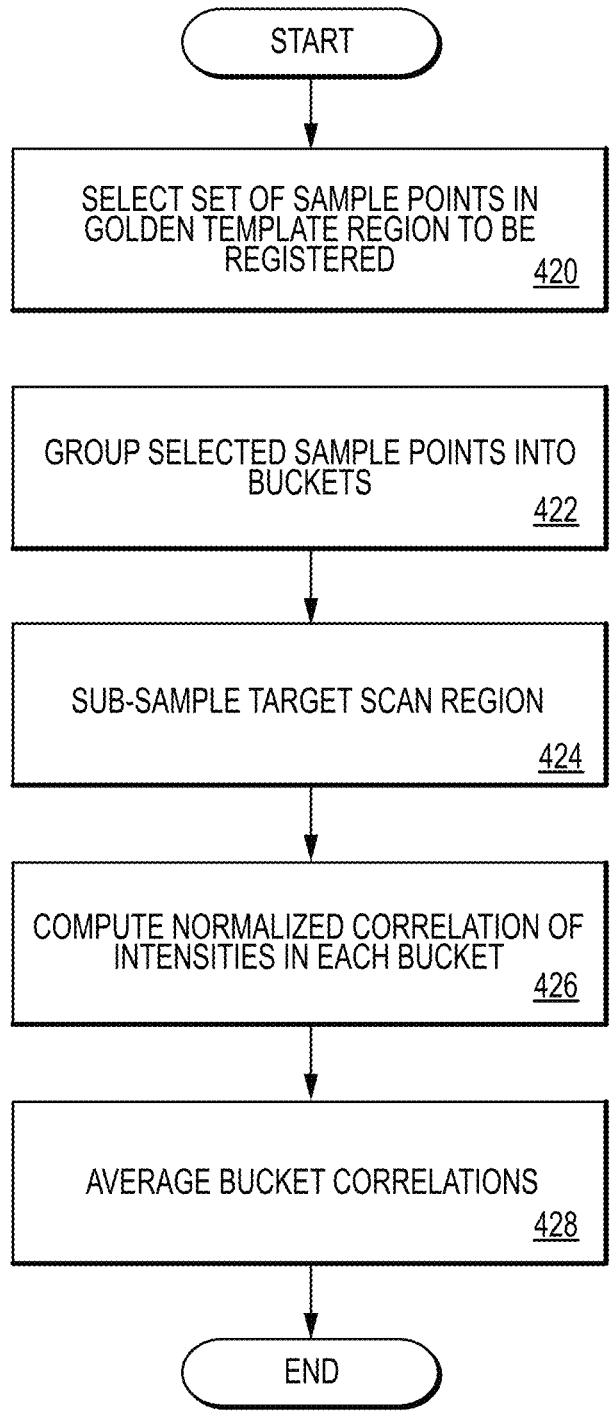
FIG. 20 depicts a flowchart illustrating one method for computing a metric for the registration framework of FIG. 18.

FIG. 20 depicts a flowchart illustrating one method for computing the metric used by the registration operations described above. For a particular registration operation, the metric may be computed in the same way, but the metric may have different parameters specified for the particular registration operation. The metric may be referred to herein as "local correlation in sample points." Initially, operation 420 selects a set of sample points in the golden template region to be registered.

For the translation and similarity transformations, the sample points may be selected as follows. Initially, a rectilinear grid of L×M×N that covers the whole bone in 3D space may be used. L, M, and N may vary from one to 16. In one embodiment, an eight by eight grid in every image slice may be used to select uniform sample points in the grown golden region of the golden template. For each grid cell, the first sample point is selected. If the sample point falls within the grown golden region, it is used. If the sample point falls outside the golden region, it is discarded.

For the affine and spline transformations, the sample points may be determined by randomly selecting one out of every 32 points in the boundary golden region of the MRI slice.

Next, operation 422 groups the selected points into buckets. In one embodiment, buckets may be formed as follows. First, the 3D space may be subdivided into cells using a rectilinear grid. Sample points that belong to the same cell are placed in the same bucket. It should be noted that sample points may be grouped into buckets to compensate for non-uniform intensities in the MRI scan.

For example, MRI scan data may be brighter in the middle of the image and darker towards the edges of the image. This brightness gradient typically is different for different scanners and may also depend on other parameters including elapsed time since the scanner was last calibrated. Additionally, high aspect ratio voxels typically result in voxel volume averaging. That is, cortical bone may appear very dark in areas where its surface is almost perpendicular to the slice and generally will not be averaged with nearby tissues. However, cortical bone may appear as light gray in the areas where its surface is almost tangent to the slice and generally may be averaged with a large amount of nearby tissues.

Next, operation 424 sub-samples the target MRI slice. Sub-sampling the target space generally has the effect of smoothing the metric function. This may remove tiny local minima such that the local minimization algorithm converges to a deeper minimum. In one embodiment, during operations 410 and 412 (of FIG. 19), each slice may be sub-sampled with an eight by eight grid. During operations 414 and 416 (of FIG. 19), each slice may be sub-sampled with a four by four grid. That is, during the sub-sampling, one point from every grid cell may be selected (e.g., the first point) and the remaining points in the grid cells may be discarded.

Next, operation 426 computes a correlation of the intensities of the points in each bucket and their corresponding points in the target MRI scan (after mapping). The correlation (NC) metric may be expressed as:

$$NC(A, B) = \frac{\sum_{i=1}^{N} A_i B_i}{\sqrt{\left(\sum_{i=1}^{N} A_i^2\right)\left(\sum_{i=1}^{N} B_i^2\right)}} \frac{N \sum A_i B_i - \sum A_i \sum B_i}{\sqrt{N \sum A_i^2 - (\sum A_i)^2} \sqrt{N \sum B_i^2 - (\sum B_i)^2}}$$

where $A_i$ is the intensity in the $i^{th}$ voxel of image A, $B_i$ is the intensity in the corresponding $i^{th}$ voxel of image B and N is the number of voxels considered, and the sum is taken from i equals one to N. It should be appreciated that the metric may be optimal when image differences are minimized (or when the correlation of image similarities is maximized). The NC metric generally is insensitive to intensity shifts and to multiplicative factors between the two images and may produce a cost function with sharp peaks and well defined minima.

Finally, operation 428 averages the correlations computed in every bucket with weights proportional to the number of sample points in the bucket.

It is to be appreciated that the above process for computing the metric may compensate for non-uniform intensities, for example, those described above with respect to FIGS. 3A-3C, in the MRI scan data.

During the registration process, an optimizer may be used to maximize image similarity between the reference image and target image by adjusting the parameters of a given transformation model to adjust the location of reference image coordinates in the target image. In one embodiment, the optimizer for a registration operation may use the transformed image (e.g., the transformed golden template) from the previous registration operation as its initial approximation. Then, local optimization techniques may be used to search for a local optimum near the initial starting approximation. This may be done so that any potential matches farther away from the feature of interest (e.g., the femur or tibia in a knee joint) reliably found in an earlier operation may be eliminated.

For the translation transformation, an exhaustive search may be performed using a grid 10×10×10 of size 5-millimeter translation vectors. A translation for every vector in the grid may be performed and the translation providing a maximum local correlation in sample points may be selected as the optimum translation.

For the similarity transformation, a regular step gradient descent optimizer may be used by one embodiment. A regular step gradient descent optimizer typically advances transformation parameters in the direction of the gradient and a bipartition scheme may be used to compute the step size. The gradient of a function typically points in the direction of the greatest rate of change and whose magnitude is equal to the greatest rate of change.

For example, the gradient for a three dimensional space may be given by:

$$\nabla f(x, y, z) = \left(\frac{\partial f}{\partial x}, \frac{\partial f}{\partial y}, \frac{\partial f}{\partial z}\right).$$

That is, the gradient vector may be composed of partial derivatives of the metric function over all the parameters defining the transform. In one embodiment the metric function may be a composition of an outer and N inner functions. The outer function may compute a metric value according to operations 426 and 428 given the vectors $\{A_i\}$ and $\{B_i\}$. The N inner functions may map N sample points from the fixed (reference) image $A_i$ into the target image $B_i$ using the transform and evaluate intensities of the target image $B_i$ in the mapped points. Each of the inner functions generally depends on the transform parameters as well as on the point in the "from" space to which the transform is applied. When computing the partial derivatives, the chain rule for computing a derivative of the function composition may be used.

To find a local minimum, parameter steps may be taken in the direction of the negative of the metric gradient (or the approximate gradient) over the transform parameter space at the current point. This generally optimizes the metric which typically has a local minimum when features of the reference image mapped into corresponding features of the target image have minimal misalignment).

The initial center of rotation for the similarity transformation (e.g., operation 382 of FIG. 17) may be specified as the center of a bounding box (or minimum sized cuboid with sides parallel to the coordinate planes) that encloses the feature (e.g., a bone) registered in the translation registration (e.g., operation 380 of FIG. 17). Scaling coefficients of approximately 40-millimeters may be used for the scaling parameters when bringing them together with translation parameters. It is to be appreciated that the gradient computation generally relies on a customized metric function in the parameter space, due to the fact that with a similarity transformation, the transform parameters do not have the same dimensionality. The translation parameters have a dimension of millimeters, while the parameters for rotational angles and scaling do not have a dimension of millimeters. In one embodiment, a metric p may be defined as $$\rho = SQRT(X^2 + Y^2 + Z^2 + (40\text{-millimeter} * A1)^2 + \ldots)$$

where X is the translation along the x axis, Y is the translation along the y axis, Z is the translation along the z axis, $A_1$ is the first rotation angle, etc. A scaling coefficient of approximately 40-millimeters may be used because it is approximately half the size of the bone (in the anterior/posterior and medial/lateral directions) of interest and results in a point being moved approximately 40-millimeters when performing a rotation of one radian angle.

In one embodiment, a maximum move of 1.5-millimeters may be specified for every point, a relaxation factor may be set to 0.98 and a maximum of 300 iterations may be performed to determine the parameters of the similarity transformation that results in minimal misalignment between the reference image and target MRI scan.

For the affine transformation, a regular step gradient optimizer may be used by one embodiment. Scaling coefficients of approximately 40-millimeters may be used for the matrix coefficients variations when bringing them together with translation parameters. A maximum 1.0-millimeter move for every point may be set for each iteration, the relaxation factor may be set to 0.98 and a maximum of 300 iterations may be performed to determine the parameters of the affine transformation that results in minimal misalignment.

For the B-spline transformation, a modified regular step gradient descent optimizer may be used by one embodiment when searching for the best B-spline deformable transformation. An MRI image gradient may often follow the bone surface in diseased areas (e.g., where the bone contact surface is severely damaged and/or where osteophytes have grown). Such a gradient may cause deformations of the golden template that would introduce large distortions in the segmented bone shape.

In one embodiment, the MRI image gradient may be corrected for such deformations by computing a normal to golden boundary vector field where every vector points towards the closest point in the golden template shape found during the affine transformation (e.g., operation 384 of FIG. 17). This may be done using a distance map (also referred to as a distance transform). A distance map supplies each voxel of the image with the distance to the nearest obstacle voxel (e.g., a boundary voxel in a binary image). In one embodiment, the gradient of the signed distance map of the golden tibia region may be mapped using the affine transformation found in operation 384 of FIG. 17. In one embodiment, a signed Danielsson distance map image filter algorithm may be used. Then, the MRI image gradient may be projected onto the vector field to obtain the corrected gradient field. This corrected gradient field is parallel to the normal to golden boundary field and typically defines a very thin subset of the set of B-spline transformations that may be spanned during the optimization.

Additionally, rather than computing one gradient vector for the transform space and taking a step along it, a separate gradient may be computed for every spline node. In one embodiment, order three B-splines (with J×K×L control nodes) may be used and J×K×L gradients may be computed, one for each control point. At every iteration, each of the spline nodes may be moved along its respective gradient. This may allow the spline curve to be moved in low contrast areas at the same time it is moved in high contrast areas. A relaxation factor of 0.95 may be used for each spline node. A maximum move of one-millimeter may be set for every point during an iteration and a maximum of 20 iterations may be performed to find the parameters of the B-spline transformation that provides minimal misalignment of the golden tibia region mapped into the target MRI scan.

Figure 21:
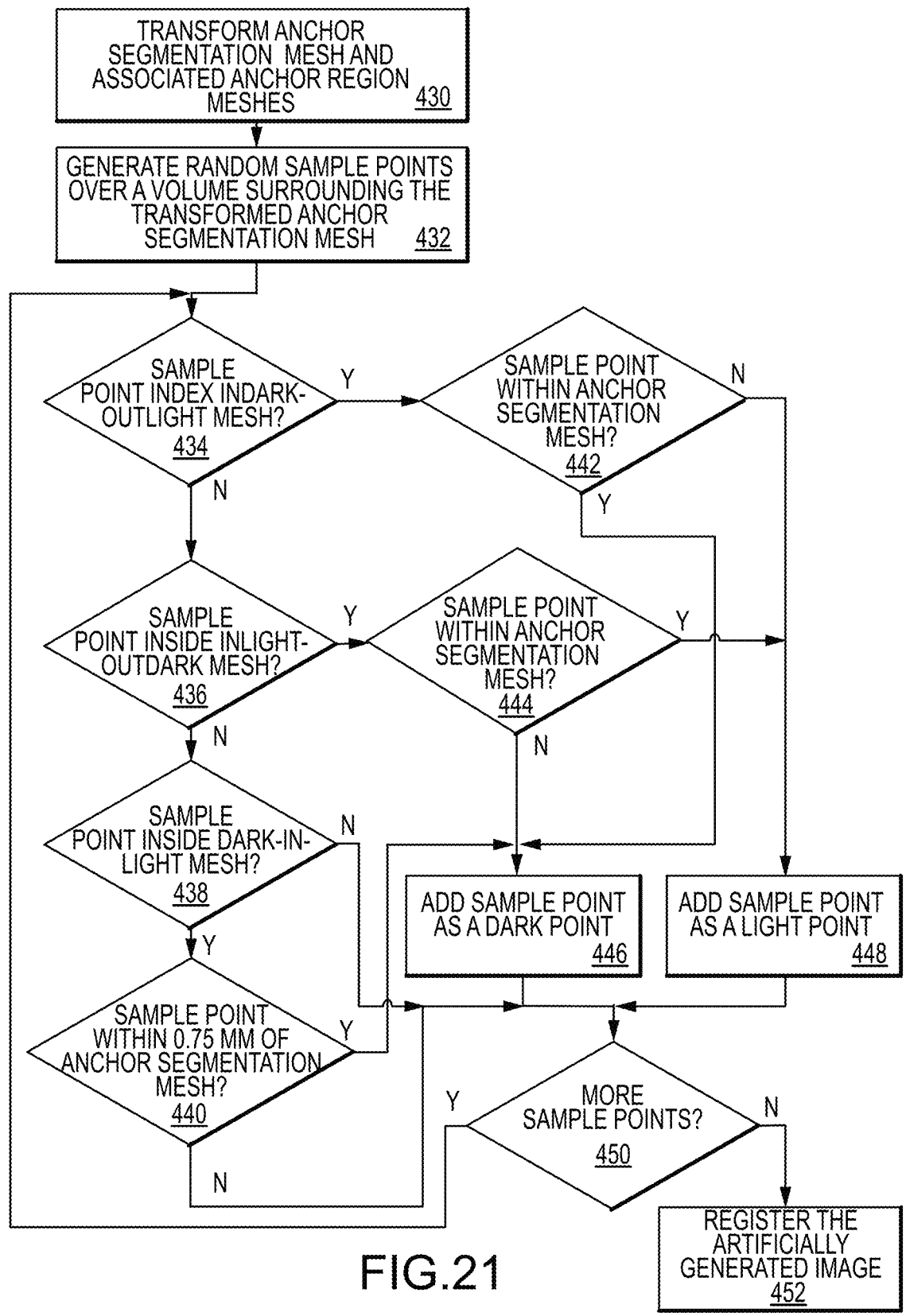
FIG. 21 depicts a flowchart illustrating one method for refining the registration results using anchor segmentation and anchor regions.

Once the position and shape of the feature of interest of the joint has been determined using image registration (operation 370 of FIG. 16), the registration results may be refined using anchor segmentation and anchor regions (operation 372 of FIG. 16). FIG. 21 depicts a flowchart illustrating one method for refining the registration results using anchor segmentation and anchor regions. Typically, during this operation, one more registration may be done using an artificially generated image for the fixed image 394 of the registration framework 390. Use of an artificial image may improve the overall segmentation by registering known good regions that typically do not change from scan to scan to correct for any errors due to diseased and/or low contrast areas that otherwise may distort the registration.

Additionally, the artificial image may be used to increase surface detection precision of articular surfaces and shaft middle regions. The image slices typically have higher resolution in two dimensions (e.g., 0.3-millimeter in the y and z dimensions) and lower resolution in the third dimension (e.g., 2-millimeters in the x dimension). The articular surfaces and shaft middle regions typically are well defined in the image slices due to these surfaces generally being perpendicular to the slices. The surface detection precision may be improved using a combination of 2D and 3D techniques that preserves the in-slice precision by only moving points within slices rather than between slices. Further, a 3D B-spline transform may be used such that the slices are not deformed independently of one another. Since each slice may not contain enough information, deforming each slice independently may result in the registration finding the wrong features. Instead, the slices as a whole may be deformed such that the registration remains near the desired feature. While each slice may be deformed differently, the difference in deformation between slices generally is small such that the changes from one slice to the next are gradual.

In one embodiment, the artificial image may comprise a set of dark and light sample points that may be used by the metric. All dark points in the artificial image may have the same intensity value (e.g., 100) and all light points in the artificial image may have the same intensity value (e.g., 200). It should be appreciated that the correlations are generally insensitive to scaling and zero shift. Thus, any intensity values may be used as long as the dark intensity value is less than the light intensity value.

Initially, operation 430 may apply the cumulative registration transform (computed by operation 370 of FIG. 16) to an anchor segmentation mesh and its three associated anchor region meshes (e.g., InDark-OutLight mesh, InLight-OutDark mesh and Dark-in-Light mesh) to generate a transformed anchor segmentation mesh and associated transformed anchor region meshes (transformed InDark-OutLight anchor mesh, transformed InLight-OutDark anchor mesh and transformed Dark-in-Light anchor mesh) that lie in a space identical to the target image space.

Then, operation 432 generates random sample points lying within a thin volume surrounding the transformed anchor segmentation mesh surface. In one embodiment, this may be a volume having an outer boundary defined by the anchor segmentation mesh surface plus 1.5-millimeters and an inner boundary defined by the anchor segmentation mesh surface minus 1.5-millimeters, which may be referred to herein as the 1.5-millimeter neighborhood. The random sample points may be generated such that they are within the image slices of the target scan but not between the slices. For example, the image slices may be transversal to the x-axis with a spacing of 2-millimeters (at x-axis locations 0.0, 2.0, 4.0, . . . ). When a sample point is selected, its x-coordinate may be one of 0.0, 2.0, 4.0, etc. but may not be 1.7, 3.0, or some non-multiple of 2.0.

In one embodiment, voxels may be marked in every image slice that belong to the 1.5-millimeter neighborhood as follows. First, the intersection of the transformed anchor mesh with every image slice may be found. It should be appreciated that the intersection of the anchor mesh with an image slice may be a polyline(s). Then, in each image slice, the polyline segments may be traversed and all pixels that intersect with the mesh may be marked. Next, a Dilate filter may be applied to the marked pixels of each image slice using a radius of 1.5-millimeters. The Dilate filter typically enlarges the marked region by adding all the points that lie within a 1.5-millimeter distance from the originally marked points.

After operation 432, operation 434 determines if a sample point lies inside the transformed InDark-OutLight mesh surface. If operation 434 determines that the sample point lies inside the transformed InDark-OutLight mesh surface, then operation 442 is performed. If operation 434 determines that the sample point does not lie inside the transformed InDark-OutLight mesh surface, then operation 436 is performed.

Operation 442 determines if the sample point lies inside the transformed anchor segmentation mesh surface. If operation 442 determines that the sample point lies inside the transformed anchor segmentation mesh surface, then operation 446 is performed. If operation 442 determines that the sample point does not lie inside the transformed anchor segmentation mesh surface, then operation 448 is performed.

Operation 436 determines if the sample point lies inside the transformed InLight-OutDark mesh surface. If operation 436 determines that the sample point lies inside the transformed InLight-OutDark mesh surface, then operation 444 is performed. If operation 436 determines that the sample point does not lie inside the transformed InLight-OutDark mesh surface, then operation 438 is performed.

Operation 444 determines if the sample point lies inside the transformed anchor segmentation mesh surface. If operation 444 determines that the sample point lies inside the transformed anchor segmentation mesh surface, then operation 448 is performed. If operation 444 determines sample point does not lie within the transformed anchor segmentation mesh surface, then operation 446 is performed.

Operation 438 determines if the sample point lies inside the transformed Dark-In-Light mesh surface. If operation 438 determines that the sample point lies inside the transformed Dark-In-Light mesh surface, then operation 440 is performed. If operation 438 determines that the sample point does not lie inside the transformed Dark-In-Light mesh surface, then operation 450 is performed.

Operation 440 determines if the sample point is within 0.75-millimeter of the surface of the transformed anchor segmentation mesh. If operation 440 determines that the sample point is within 0.75-millimeter of the surface of the transformed anchor segmentation mesh, then operation 446 is performed. If operation 440 determines that the sample point is not within 0.75-millimeter of the surface of the anchor segmentation mesh, then operation 450 is performed.

Operation 446 adds the sample point to the artificial image as a dark point. Then, operation 450 is performed.

Operation 448 adds the sample point to the artificial image as a light sample point. Then, operation 450 is performed.

Operation 450 determines if there are more randomly generated samples points to be added to the artificial image. If operation 450 determines that there are more randomly generated sample points to be added to the artificial image, then operation 434 is performed. If operation 450 determines that there are no more randomly generated sample points to be added to the artificial image, then operation 452 is performed.

Figure 22:
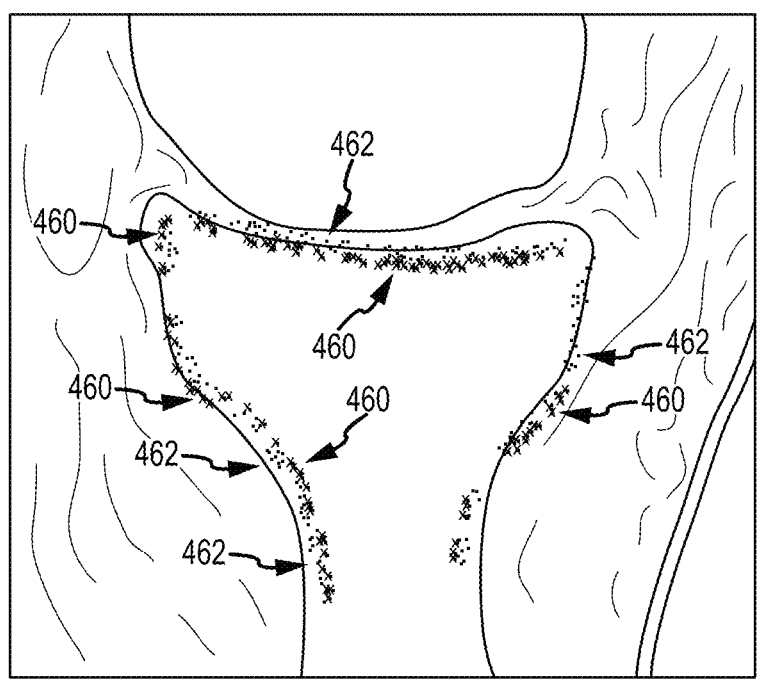
FIG. 22 depicts a set of randomly generated light sample points and dark sample points of a tibia.

FIG. 22 depicts a set of randomly generated light sample points 460 and dark sample points 462 over the target MRI 464. In one embodiment, approximately 8,000 sample points (light and dark) may be generated over the entire artificial image.

Referring again to FIG. 21, if operation 450 determines that there are no more randomly generated sample points to be added to the artificial image, operation 452 registers the set of dark and light points to the target MRI scan. This operation may perform a registration similar to the registration operation 196 (depicted in FIG. 17). In this transformation, a subset of B-spline deformable transformations may be performed that move points along their respective slices, but not transversal to their respective slices.

In a B-spline deformable transform, a translation vector for every control point (e.g., in the set of J×K×L control points) may be specified. To specify a transform that moves any point in 3D space along the y and z slice coordinates but not along the x coordinate, a restriction on the choice of translation vectors in the control points may be introduced. In one embodiment, only translation vectors with the x coordinate set equal to zero may be used to move points in the plane of the slice (e.g., the y and z directions) but not transversal to the slice (e.g., the x direction).

The use of anchor region meshes which typically are well pronounced in most image scans may reduce registration errors due to unhealthy areas and/or areas with minimal contrast differences between the feature to be segmented and surrounding image areas. For example, in the area where a healthy bone normally has cartilage, a damaged bone may or may not have cartilage. If cartilage is present in this damaged bone region, the bone boundary separates the dark cortical bone from the gray cartilage matter. If cartilage is not present in this area of the damaged bone, there may be white liquid matter next to the dark cortical bone or there may be another dark cortical bone next to the damage bone area. Thus, the interface from the cortical bone to the outside matter in this region of the damaged bone typically varies from MRI scan to MRI scan. In such areas, the interface between the cortical and the inner cancellous bone may be used as an anchor region.

The use of a subset of B-Spline deformable transforms may reduce errors due to the 2-millimeter spacing between image slices.

Figure 23:
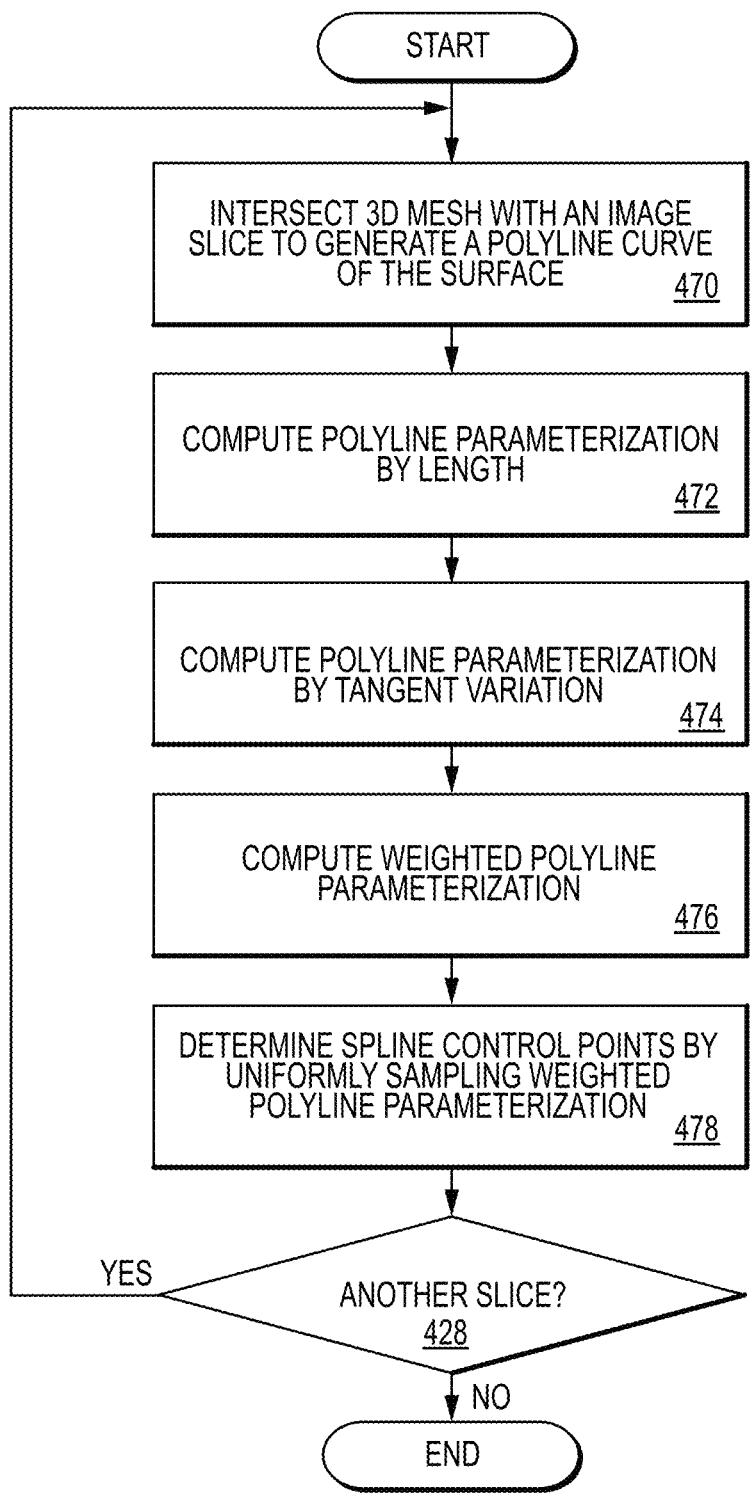
FIG. 23 depicts a flowchart illustrating one method for generating spline curves to outline features of interest in each target MRI slice.

FIG. 23 depicts a flowchart illustrating one method for generating spline curves outlining the surface of a feature of interest in each target MRI slice (e.g., operation 376 of FIG. 16). Initially, operation 470 intersects the generated 3D mesh model of the feature surface with a slice of the target scan data. The intersection defines a polyline curve of the surface of the feature (e.g., bone) in each slice. Two or more polyline curves may be generated in a slice when the bone is not very straightly positioned with respect to the slice direction.

A polyline curve is a piecewise linear approximation to a curved feature shape. Generally, this curve should be easy to manipulate with a set of control points. The polyline curve may have many segments, making it more difficult to manipulate the polyline curve (e.g., during operation 254 or 260 of FIG. 6). One embodiment may generate one or more Kochanek splines from the polyline curve. Each spline typically has a smaller number of control points and typically fits the polyline curve with about 0.2-millimeter deviation. Generally, a Kochanek spline may have more control points along the high curvature regions of the polyline curve and fewer control points along low curvature regions (i.e., where the curve tends to be flatter) of the polyline curve.

Figure 24:
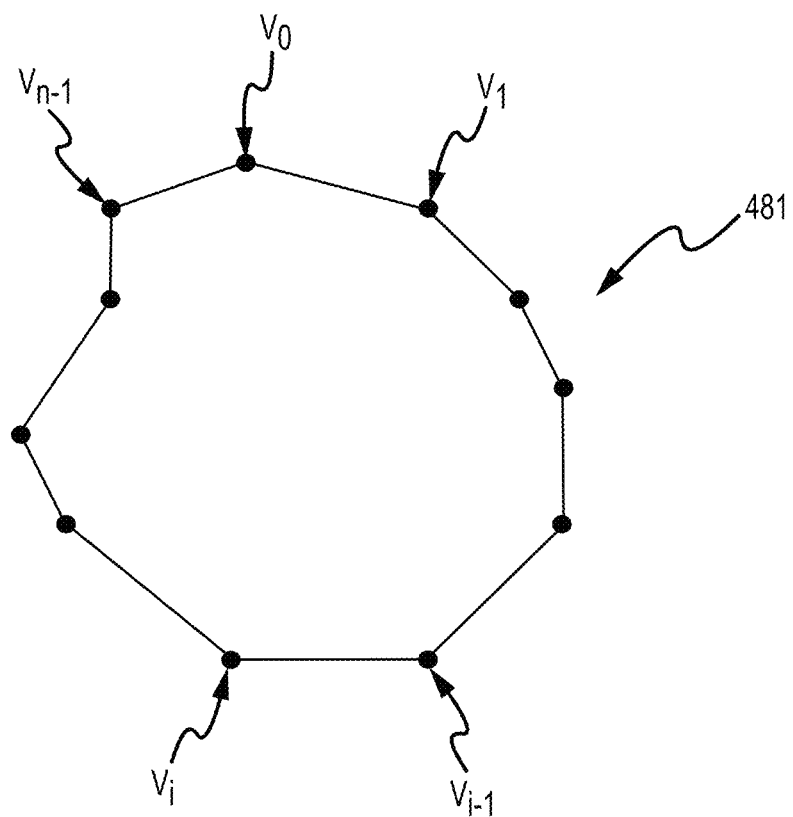
FIG. 24 depicts a polyline curve with n vertices.

Once a polyline curve has been generated, operation 472 may compute a polyline parameterization, $L_i$, as a function of the polyline's length. FIG. 24 depicts a polyline curve 481 with n vertices, $V_0, V_1, \ldots V_{i-1}, V_i \ldots V_{n-1}$. Note that vertex $V_0$ follows vertex $V_{n-1}$ to form a closed contour curve. The length of a segment connecting vertices Vi–1 and Vi may be denoted by $\Delta L$, such that the length parameterization, $L_i$, of the polyline at vertex $V_i$ may be expressed as:

$$L_i = \Delta L_0 + \Delta L_1 + \ldots + \Delta L_i.$$

Next, operation 474 may compute a polyline parameterization, $A_i$, as a function of the polyline's tangent variation. The absolute value of the angle between a vector connecting vertices $V_{i-1}$ and $V_i$ and a vector connecting vertices $V_i$ and $V_{i+1}$ may be denoted by $\Delta A_i$ such that the tangent variation parameter $A_i$ at vertex $V_i$ may be expressed as:

$$A_i = \Delta A_0 + \Delta A_1 + \ldots + \Delta A_i.$$

Then, operation 476 determines a weighted sum parameterization of the polyline length and tangent variation parameterizations. In one embodiment the weighted sum parameterization, $W_i$, at vertex $V_i$ may be computed as:

$$W_i = \alpha * L_i + \beta * A_i$$

where $\alpha$ may be set to 0.2 and $\beta$ may be set to 0.8 in one embodiment.

Then, operation 478 may perform a uniform sampling of the polyline using the W parameterization results determined by operation 476. In one embodiment, a spacing interval of approximately 3.7 of the W parameter value may be used for positioning K new sample points. First, K may be computed as follows:

$$K = \text{ROUND}(W_n/3.7).$$

That is, the W parameter value, which is the last computed value $W_n$, may be divided by 3.7 and the result rounded to the nearest integer to get the number of new sample points. Then, the spacing of the sample points, $\Delta W$ may be computed as:

$$\Delta W = W_n/K.$$

Finally, the K new sample points, which are uniformly spaced, may be positioned at intervals $\Delta W$ of the parameter W. The resulting sample points may be used as control points for the Kochanek splines to convert the polyline into a spline. A Kochanek spline generally has a tension, a bias and a continuity parameter that may be used to change the behavior of the tangents. That is, a closed Kochanek spline with K control points typically is interpolated with K curve segments. Each segment has a starting point, an ending point, a starting tangent and an ending tangent. Generally, the tension parameter changes the length of the tangent vectors, the bias parameter changes the direction of the tangent vectors and the continuity parameter changes the sharpness in change between tangents. In certain embodiments, the tension, bias and continuity parameters may be set to zero to generate a Catmull-Rom spline.

In one embodiment, operation 478 may perform a linear interpolation of $W_i$ and $W_{i+1}$ to locate a sample point that lies between $W_i$ and $W_{i+1}$. The interpolated value of W may be used to determine the corresponding sample location in the segment connecting vertices $V_i$ and $V_{i+1}$.

In certain embodiments, operation 478 may divide the W parameter value by six to obtain the new number of sample points K. That is, $$K = \text{ROUND}(W_n/6).$$

Then, a measure of closeness (i.e., how closely the spline follows the polyline) may be computed as follows. First, the spline is sampled such that there are seven sample points in every arc of the spline (i.e., 7*K sample points). Then, the sum of the squared distances of the sample points to the polyline may be computed. Next, the coordinates of the K control points are varied (i.e., two*K parameters). Then, a local optimization algorithm is used to find the closest spline. If the closest spline found during the optimization is not within a certain precision (e.g., within approximately 0.4-millimeter of the polyline), then the number of control points, K, may be increased by one. The new number of control points may be uniformly distributed along the W parameter, and another optimization performed to find the new closest spline. Generally one to two optimizations provide a spline that follows the polyline with the desired degree of precision (e.g., within approximately 0.2-millimeter).

Finally, operation 480 determines if a spline curve(s) should be generated for another image slice. If operation 480 determines that a spline curve should be generated for another slice, then operation 472 is performed. If operation 480 determines that there are no more image slices to be processed, the method terminates.

As discussed above, in one embodiment, the output of the segmentation may be a triangular mesh (e.g., a 3D surface model) of the segmented bone(s) of a joint (e.g., the femur and tibia of a knee joint). The mesh generated generally represents a watertight surface that closely follows the segmentation contour curves of the slices, smoothly interpolates between the segmentation contour curves, and may have a low triangular count.

In one embodiment, a triangular mesh may be generated as follows. The segmentation data may be represented in 3D using (x, y, z) coordinates with the image slices transversal to the x direction. Thus, the segmentation contours lie in yz planes with fixed values of x. Initially, an in-slice distance image may be computed for each segmented slice. The value of each (y, z) pixel in an in-slice distance image is the distance to the closest point in the contours when the point is located inside one of the contours and is the inverse (i.e., negative) of the distance to the closest point in the contours when the point is outside all of the contours.

Then, a marching cubes algorithm may be applied to the in-slice distance images to generate the mesh. The marching cubes algorithm is a computer algorithm for extracting a polygonal mesh of an isosurface (i.e., the contours) from a three-dimensional scalar field (or voxels). The algorithm typically proceeds through the voxels, taking eight neighbor voxels at a time (thus forming an imaginary cube) and determines the polygon(s) needed to represent the part of the isosurface (i.e., contour) that passes through the imaginary cube. The individual polygons are then fused into the desired surface. The generated mesh generally passes through the zero level of the signed distance function in each slice such that the mesh lies close to the contours.

It is to be appreciated that the image resolution in the y and z directions typically determines how well the zero level of the signed distance function approximates the original contours and may also determine the triangular count in the resulting mesh. In one embodiment, a voxel size of 1.5-millimeters in the y and z directions may be used. This typically yields deviations within 0.1-millimeter of the original contours and produces a smooth mesh.

In one embodiment, a smoothing operation may be performed in the x direction (i.e., transversal to the image slices) to compensate for surface waviness that may have been introduced when the automatically generated contours were adjusted (e.g., during operation 260 of FIG. 6). Such waviness may occur in regions of an image slice where there is minimal contrast variation and the curve is positioned by the technician. Typically a smooth best guess mesh in uncertain areas may be desired when generating a planning model that may be used to locate the position of an implant. Alternatively, a smooth overestimation may be desired in uncertain areas such as in an arthritic model used to create a jig.

In one embodiment, simple smoothing may be used and the amount of smoothing (i.e., how much a voxel value may be modified) may be controlled by two user specified parameters, MaxUp and MaxDown. After an average is computed for a voxel, it is clamped using these values to limit the amount of smoothing. The smoothing operation typically does not change the image much in areas where the image contrast is good. For smooth best guess averaging in uncertain areas, MaxUp and MaxDown may each be set to 1 millimeter. For smooth overestimation averaging in uncertain regions, MaxUp may be set to 2-millimeters and MaxDown may be set to 0-millimeter.

Figure 25:
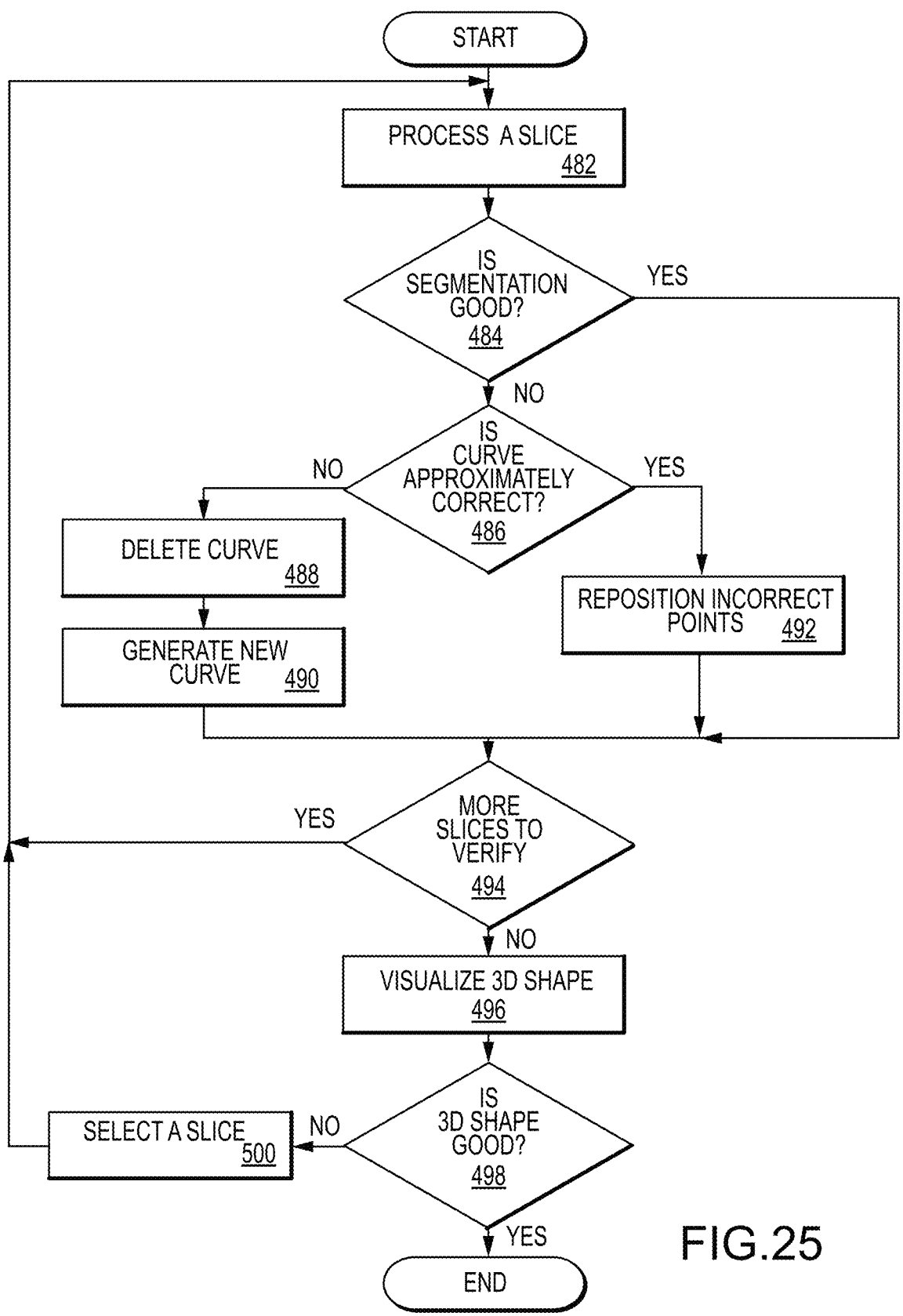
FIG. 25 depicts a flowchart illustrating one method for adjusting segments.

The operation of adjusting segments of the segmentation process will now be described with reference to FIG. 25, which depicts a flowchart for one method of adjusting segments (e.g., operation 254 or operation 260 of the flowchart depicted in FIG. 6). In one embodiment, the segmentation data may be manually adjusted by a trained technician sitting in front of a computer 6 and visually observing the automatically generated contour curves in the image slices on a computer screen 9. By interacting with computer controls 11, the trained technician may manually manipulate the contour curves. The trained technician may visually observe all of the contours as a 3D surface model to select an image slice for further examination.

Initially, in operation 482 a slice is selected for verification. In one embodiment, the slice may be manually selected by a technician.

Next, operation 484 determines if the segmentation contour curve in the selected slice is good. If operation 484 determines that the segmentation contour curve is good, then operation 494 is performed. If operation 484 determines that the segmentation contour curve is not good, then operation 486 is performed.

Operation 486 determines if the segmentation contour curve is approximately correct. If operation 486 determines that the contour curve is approximately correct, then operation 492 is performed.

Figure 26:
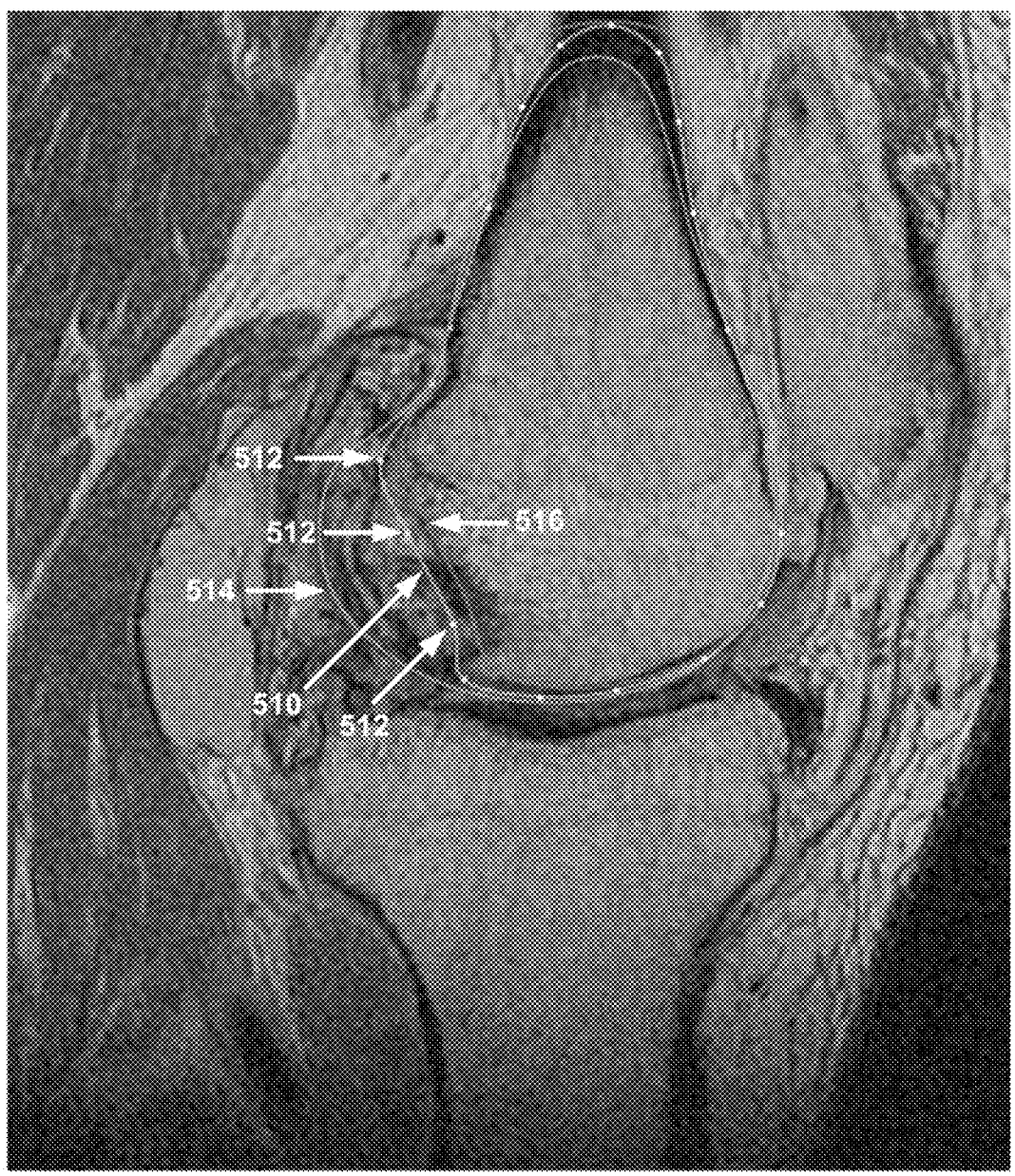
FIG. 26 is a sagittal plane image slice depicting a contour curve with control points outlining a femur with superimposed contour curves of the femur from adjacent image slices.

In operation 492 incorrect points of the segmentation contour curve may be repositioned. In one embodiment this may be performed manually by a trained technician. It is to be appreciated that it may be difficult for the technician to determine where the correct contour curve should be located in a particular slice. This may be due to missing or unclear bone boundaries and/or areas with little contrast to distinguish image features. In one embodiment, a compare function may be provided to allow the technician to visually compare the contour curve in the current slice with the contour curves in adjacent slices. FIG. 26 depicts an image showing the contour curve 510 (e.g., a spline curve) with control points 512 of the contour curve 510 for the current image slice as well the contour curves 514, 516 of the previous and next image slices, respectively, superimposed on the current image slice.

It may be difficult to determine where the correct segmentation contour curve should be located due to missing or unclear bone boundaries due to the presence of unhealthy areas, areas with limited contrast differences, and/or voxel volume averaging. When visually comparing adjacent slices, the technician may visualize the data in 2D planes (xy, yz, and xz) and in 3D. In one embodiment, the technician may select an area for examination by positioning a crosshair on a location in any window and clicking a mouse button to select that image point. The crosshair will be placed at the desired point and may be used to indicate the same location when the data is visualized in each window.

The technician may use the spline control points to manipulate the shape of the curve. This may be done by using a mouse to click on a control point and dragging it to a desired location. Additionally, the technician may add or delete spline curve control points. This may be done by using a mouse to select two existing control points between which a control point will be inserted or deleted. Alternatively, the technician may use a mouse cursor to point to the location on the curve where a control point is to be inserted. In one embodiment, by pressing the letter I on a keyboard and then positioning the cursor at the desired location, clicking the left mouse button will insert the control point. A control point may be deleted by pressing the letter D on the keyboard and then positioning the cursor over the desired control point to be deleted. The selected control point will change color. The selected control point will be deleted when the left mouse button is clicked.

Referring again to FIG. 25, if operation 486 determines that the contour curve is not approximately correct, operation 488 is performed to delete the curve. Then, operation 490 is performed.

Operation 490 generates a new segmentation contour curve for the image slice. In one embodiment, a technician may use a spline draw tool to insert a new spline curve. With the spline draw tool, the technician may click on consecutive points in the current slice to indicate where the spline curve should be located and a spline curve is generated that passes through all of the indicated points. A right mouse click may be used to connect the first and last points of the new spline curve. Alternatively, the technician may use a paste command to copy the spline curve(s) from the previous slice into the current slice. The spline control points may then be manipulated to adjust the spline curves to follow the feature in the current image slice.

In another embodiment, a paste similar command may be used by the technician to copy the spline curve from the previous slice into the current slice. Rather then pasting a copy of the spline curve from the previous slice, the spline curve may be automatically modified to pass through similar image features present in both slices. This may be done by registering a region around the spline curve in the previous slice that is from about 0.7-millimeter outside of the curve to about 5.0-millimeter within the curve. Initially, this region is registered using an affine transformation. Then, the result of the affine transform may be used as a starting value for a B-Spline deformable transformation. The metric used for the transform may be the local correlation in sample points metric described previously. Typically, more sample points may be taken closer to the curve and fewer sample points taken farther away from the curve. Next, the spline control points may be modified by applying the final transformation found to the spline control points. Additionally, the trained technician may adjust from zero to a few control points in areas where the bone boundary changes a lot from the slice due to the bone being tangent to the slice or in areas of limited contrast (e.g., where there is an osteophyte growth). Then, operation 492 is performed.

Operation 494 determines if there are additional slices to be verified. If operation 494 determines that there are additional slices to be verified, operation 482 is performed.

If operation 494 determines that there are no more slices to be verified, then operation 496 is performed. Operation 496 generates a 3D surface model of the segmented bone.

Figure 27:
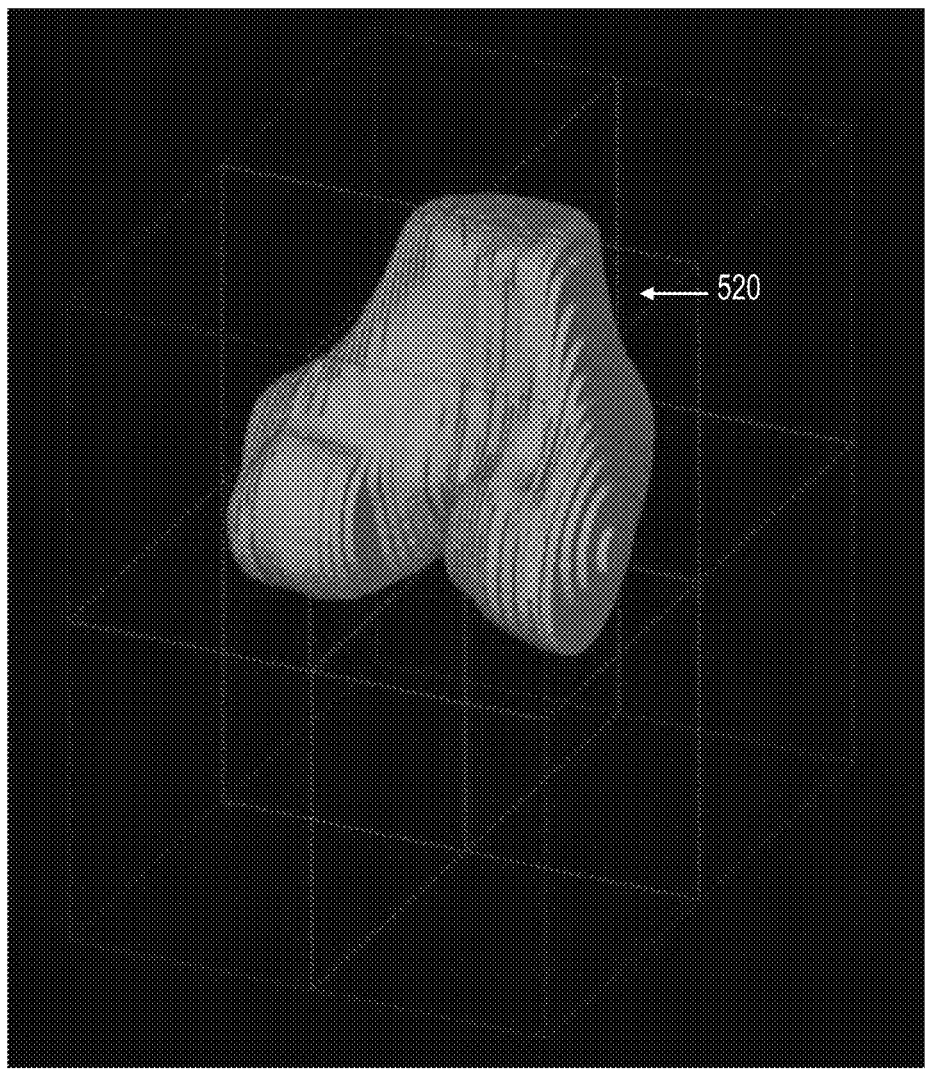
FIG. 27 depicts a 3D slice visualization of a femur showing the voxels inside of the spline curves.

Then, operation 498 determines if the 3D surface model is good. In one embodiment, a technician may manually determine if the 3D surface model is good. The technician may use a spline 3D visualization tool that generates a slice visualization showing the voxels inside all of the splines in 3D, as illustrated by the 3D shape 520 depicted in FIG. 27. This spline 3D visualization tool typically may be generated in real time to provide interactive updates to the technician as the spline curves are manually edited. Alternatively, a mesh visualization may be generated in response to a technician command. The mesh visualization typically generates a smooth mesh that passes close to all the spline curves, e.g., mesh 290 depicted in FIG. 9.

If operation 498 determines that the 3D model is not good, then operation 500 is performed. Operation 500 selects a slice lying in an area where the 3D shape is not good. In one embodiment, a technician may manually select the slice. Then, operation 482 is performed.

If operation 498 determines that the 3D model is good, then the method terminates.

The 3D surface models of the lower end of the femur and the upper end of the tibia of a patient's knee may be used to create arthroplasty jigs and/or implants. For example, the models may be used to create femur and tibia jigs that can be used with a patient's femur and tibia as disclosed in the various U.S. Patent Applications incorporated by reference herein in this Detailed Description and filed by Park and Park et al. Automatic segmentation of image data to generate 3D bone models may reduce the overall time required to perform a reconstructive surgery to repair a dysfunctional joint and may also provide improved patient outcomes.

c. Segmentation Using Landmarks of Scanner Modality Image Data to Generate 3D Surface Model of a Patient's Bone Now begins a discussion of an alternative embodiment of image segmentation. The alternative embodiment includes placing landmarks 777 (in FIG. 35A-FIG. 35H) on image contours. The landmarks 777 are then used to modify a golden bone model (e.g., golden femur or golden tibia), the resulting modified golden bone model being the output of segmentation.

Similar to the embodiment of image segmentation discussed above in section b. of this Detailed Discussion, in one version of the alternative embodiment of image segmentation, the 2D images 16 of the patient's joint 14 are generated via the imaging system 8 (see FIG. 1A and [block 100] of FIG. 1B). These images 16 are analyzed to identify the contour lines of the bones and/or cartilage surfaces that are of significance with respect to generating 3D models 22, 36, as discussed above in section a. of this Detailed Discussion with respect to [blocks 110 and 130] of FIGS. 1C and 1D. Specifically, a variety of image segmentation processes may occur with respect to the 2D images 16 and the data associated with such 2D images 16 to identify contour lines that are then compiled into 3D bone models, such as bone models 22, restored bone models 28, and arthritic models 36.

Algorithms and software are described in section b. of this Detailed Discussion for automatic and semi-automatic image segmentation. In section c. of the Detailed Description, alternative software tools and underlying methods are described, such alternative tools and methods helping a user to quickly generate bone models. Because the alternative software requires some user input such as, for example, initial Landmark positions, final verification and, in some instances, adjustment, this alternative segmentation process can be considered a semi-automatic segmentation process.

In some cases the alternative embodiment described in section c. of this Detailed Discussion may significantly reduce the user time spent on segmentation. In particular, compared to manual segmentation (where the user draws contour(s) by hand on each applicable slice for each applicable bone), the user time may be reduced by approximately five times when a user segments a planning model intended for communicating a preoperative planning model to a surgeon. For that purpose, a user may generate 3D bone models with high precision in particular areas and less precision in other areas. In some implementations, a user may get high precision (e.g., 0.5 mm) at well defined bone contours in MRI images outside the implant regions and less precision (e.g., up to 2 mm) in the regions that will be replaced with implants by spending approximately 3-4 minutes in the user interface ("UI") setting landmarks for the algorithm. If improved precision is desired, the user may position more landmarks and thus spend more time in the UI.

In one embodiment, the software tool described in section c. of the Detailed Discussion is called "Segmentation using Landmarks". This tool may be implemented inside software application PerForm 1.0. A variety of processes and methods for performing image segmentation using landmarks are disclosed in the remainder of this Detailed Description.

The imager 8 typically generates a plurality of image slices 16 via repetitive imaging operations. Depending on whether the imager 8 is a MRI or CT imager, each image slice will be a MRI or CT slice. As shown in FIG. 2A, the image slice may depict the cancellous bone 200, the cortical bone 202 surrounding the cancellous bone, and the articular cartilage lining portions of the cortical bone 202 of an object of interest of a joint, e.g., a femur 204 in a patient's knee joint 14. The image may further depict the cancellous bone 206, the cortical bone 208 of another object of interest in the joint, e.g., a tibia 210 of the knee joint 14. In one embodiment, each image slice 16 may be a two-millimeter 2D image slice.

One embodiment may segment one or more features of interest (e.g., bones) present in MRI or CT scans of a patient joint, e.g., knee, hip, elbow, etc. A typical scan of a knee joint may represent approximately a 100-millimeter by 150-millimeter by 150-millimeter volume of the joint and may include about 40 to 80 slices taken in sagittal planes. A sagittal plane is an imaginary plane that travels from the top to the bottom of the object (e.g., the human body), dividing it into medial and lateral portions. It is to be appreciated that a large inter-slice spacing may result in voxels (volume elements) with aspect ratios of about one to seven between the resolution in the sagittal plane (e.g., the y z plane) and the resolution along the x axis (i.e., each scan slice lies in the yz plane with a fixed value of x). For example, a two-millimeter slice that is 150-millimeters by 150-millimeters may be comprised of voxels that are approximately 0.3-millimeter by 0.3-millimeter by 2-millimeters (for a 512 by 512 image resolution in the sagittal plane).

In one embodiment, each slice may be a gray scale image with a resolution of 512 by 512 voxels where the voxel value represents the brightness (intensity) of the voxel. The intensity may be stored as a 16-bit integer resulting in an intensity range from 0 to 65,535, where 0 may represent black and 65,535 may represent white. The intensity of each voxel typically represents the average intensity of the voxel volume. Other embodiments may employ scans having higher or lower resolutions in the sagittal plane, different inter-slice spacing, or images where the intensity may be represented by a 24 bit vector (e.g., eight bits each for a red component, green component and blue component). Additionally, other embodiments may store intensity values as 8-bit or 32-bit signed or unsigned integers or floating point values.

Typical MRI and CT scan data generally provide images where parts of a bone boundary of interest may be well defined while other parts of the bone boundary may be difficult to determine due to voxel volume averaging, the presence of osteophyte growth, the presence of tissue having similar image intensities in neighboring areas to the object to be segmented, amongst other things. Such poor definition of parts of the bone boundary in the images may cause fully automated segmentation techniques to fail. For example, FIG. 2A depicts regions 212 within a slice where an object boundary may not be visible due to neighboring tissue having about the same intensity as the feature of interest. Depicted in FIG. 2B are regions 214 that may be extended into the slice from adjacent slices due to a high voxel aspect ratio. Depicted in FIG. 2C is a region 216 of the bone boundary 218 that may disappear or lose regularity when the bone boundary 218 is approximately tangent to the slice.

In one embodiment, a user may provide some additional input to the auto-segmentation algorithm, and the algorithm could use the additional user input for more accurate and faster segmentation of features of interest. For example, the additional user input may be a set of points on the boundary of the feature of interest. In the context of a knee procedure, the points might be on the Femur knee bone boundary or on the Tibia knee bone boundary. These can be called landmark points or simply landmarks 777.

In order for a user to provide particular landmark points, the software may allow loading MRI or CT image data, viewing and scrolling over image slices, specifying landmark points in the slices and editing them. The software may also allow visualization of the segmentation results (i.e., segmentation curves drawn in the image slices). The software may also generate a 3D model from 2D outlining curves in 2D slices.

In one embodiment, PerForm software may be used to provide functionality for loading MRI or CT scanned data, visualizing sagittal, coronal and axial slices and scrolling over them, drawing spline curves in slices, and generating a 3D mesh model passing through a set of spline curves. In one embodiment, a 3D mesh typically is a collection of vertices, edges, and faces that may define the surface of a 3D object. The faces may consist of triangles, quadrilaterals or other simple convex polygons. It should be appreciated that any other curve types may be employed instead of spline curves. For example, polyline curves may be used.

In one embodiment, a tool called "Segmentation using Landmarks" is added to PerForm software. Such a tool provides a UI for landmarks positioning and editing. The tool also provides a button "Segment", which invokes the segmentation algorithm. The algorithm uses 3D image and landmarks and generates spline curves outlining the required bone.

Figure 28:
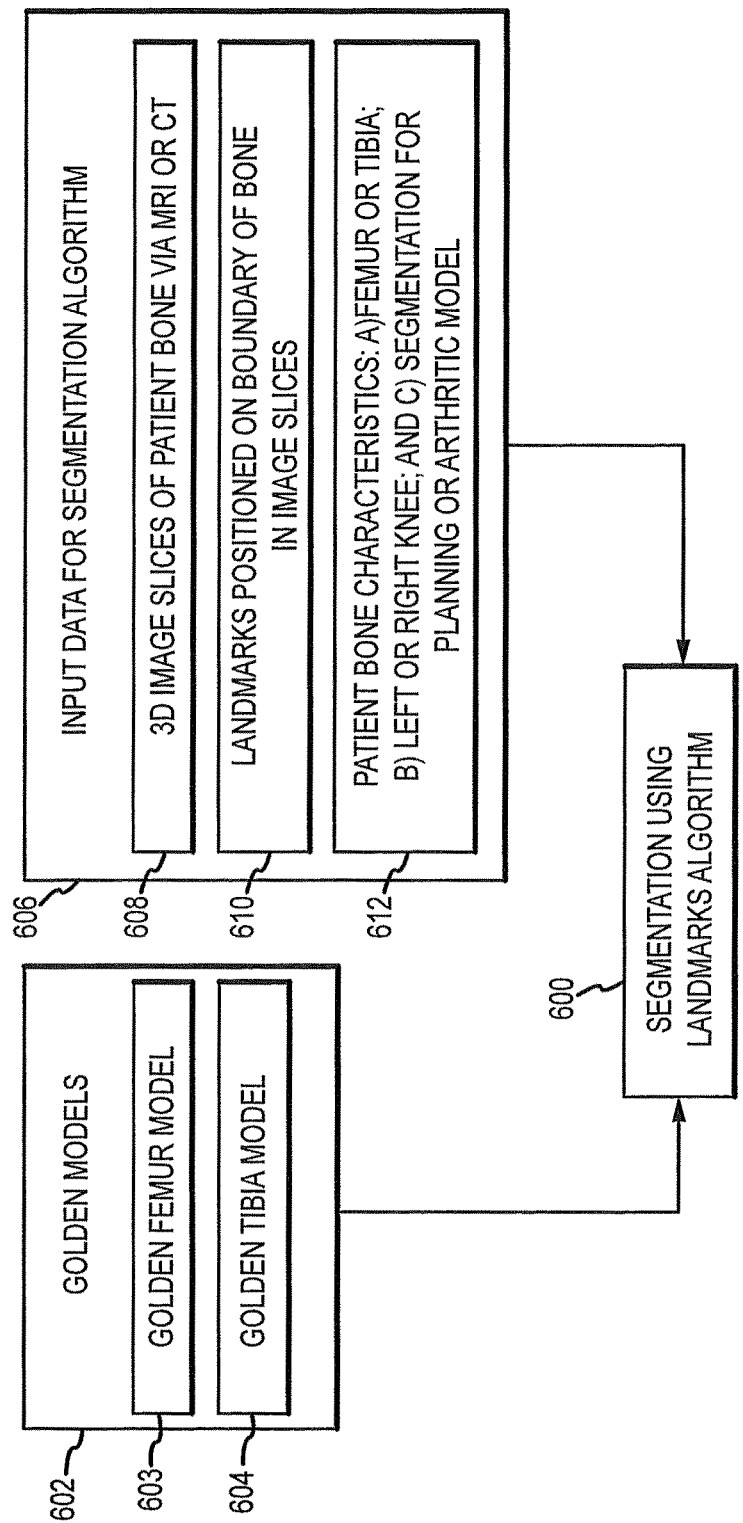
FIG. 28 is a diagram depicting types of data employed in the image segmentation algorithm that uses landmarks.

To begin the detailed discussion of the alternative embodiment of image segmentation described in this section c. of the Detailed Description, wherein landmarks 777 placed on image contours are used to modify a golden bone model (e.g., golden femur or golden tibia), the resulting modified golden bone model being segmented, reference is made to FIG. 28, which is a diagram depicting types of data employed in the image segmentation algorithm that uses landmarks. As shown in FIG. 28, the data employed in the segmentation algorithm 600 may be characterized as being two types of data. The first type of data exists in the system once generated and is for use with multiple patients and is not generated specifically for the patient for which the current image segmentation is being undertaken. This type of data may be called golden model data 602 and is derived similar to as discussed above with respect to FIG. 11, etc. and as generally reiterated below. The golden model data 602 may include, for example, one or more golden femur models 603 and one or more golden tibia models 604. If the joint being treated is something other than a knee, for example, the patient's arm, then the golden model data 602 may include another type of golden bone model, for example, a golden radius or golden ulna.

The second type of data is specific to the patient for which the current image segmentation is being undertaken. This type of data may be called input data for segmentation algorithm 606. The input data 606 includes 3D image slices data 608, which is 3D image slice data of the patient bone via MRI, CT or another type of medical imaging. The input data 606 also includes landmark data 610, which is landmarks 777 positioned on boundaries of the patient bone in the image slices. The input data 606 further includes patient bone characteristics 612 such as bone type (e.g., whether the bone is a tibia or femur), bone right or left handedness, and whether the segmentation is being done to generate an arthritic model 36 (see FIG. 1D) or a planning or restored bone model 28 (see FIG. 1C). As explained below, the golden model data 602 and the input data 606 are used in the segmentation algorithm 600 to segment the 3D image employing landmarks 777.

Figure 29:
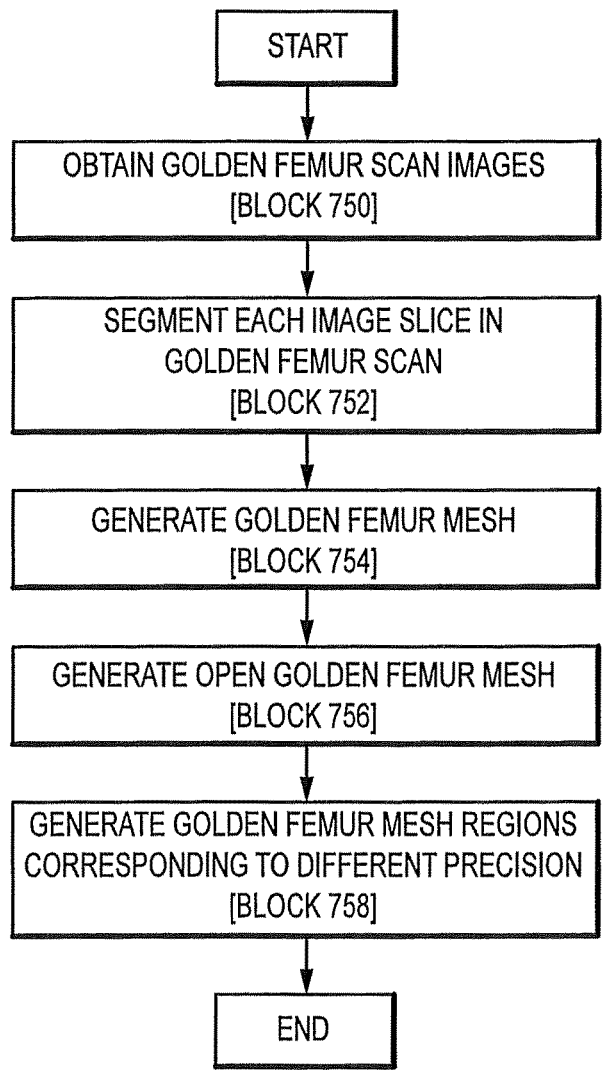
FIG. 29 is a flowchart illustrating the overall process for generating a golden femur model of FIG. 28.

As shown in FIG. 29, which is a flowchart illustrating the overall process for generating a golden femur model 603 of FIG. 28, golden femur scan image slices 616 are obtained in operation 750. For example, as discussed above with respect to FIG. 11 above, a representative femur 618 that is free of damage and disease may be scanned via medical imaging, such as, for example, MRI or CT. Where the golden femur model 603 is to be employed in generating a bone model 22 (see block 110 of FIG. 1C) and cartilage geometry is not of interest, the golden femur scan images slices 616 may be of a femur having damaged cartilage as long as the bone shape is otherwise desirable (e.g., normal) and free of deterioration or damage. Where the golden femur model 603 is to be employed in generating an arthritic model 36 (see block 130 of FIG. 1D) and cartilage geometry is of interest, the golden femur scan images slices 616 may be of a femur having both cartilage and bone shape that are desirable (e.g., normal) and free of deterioration or damage.

The appropriate femur scan may be selected by screening multiple MRI femur scans to locate an MRI femur scan having a femur that does not have damaged cancellous and cortical matter (i.e., no damage in femur regions that should be present in this particular model), which has good MRI image quality, and which has a relatively average shape, e.g., the shaft width relative to the largest part is not out of proportion (which may be estimated by eye-balling the images). This femur scan data, referred to herein as a golden femur scan, may be used to create a golden femur template.

It is to be appreciated that several MRI scans of a femur (or other bone of interest) may be selected, a template generated for each scan, statistics gathered on the success rate when using each template to segment target MRI scans, and selecting the one with the highest success rate as the golden femur template.

In other embodiments, a catalog of golden models may be generated for any given feature, with distinct variants of the feature depending on various patient attributes, such as (but not limited to) weight, height, race, gender, age, and diagnosed disease condition. The appropriate golden mesh would then be selected for each feature based on a given patient's characteristics.

Figure 30:
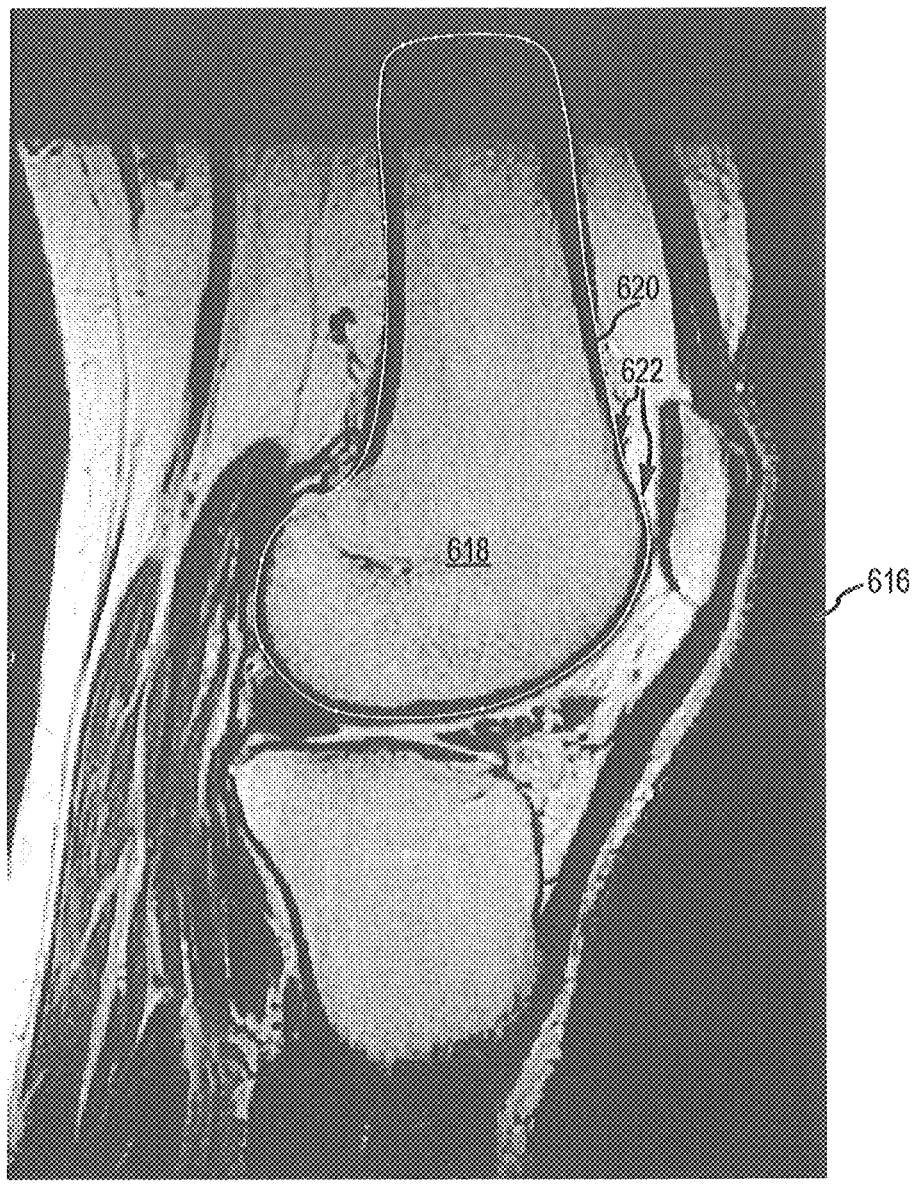
FIG. 30 is an image slice of the representative femur to be used to generate a golden femur mesh.

In operation 752 and as indicated in FIG. 30, each of the image slices 616 of the representative femur 618 are segmented with a contour curve or spline 620 having control points 622 and in a manner similar to that discussed above with respect to FIG. 12A, etc. For example and as shown in FIG. 30, where the golden model is to be used in the generation of a bone model 22 (see block 110 of FIG. 1C) and cartilage geometry is not of interest, each segmentation region includes cancellous matter and cortical matter of the femur in a manner similar to that discussed above with respect to the cancellous matter 322 and cortical matter 324 of the tibia depicted in FIG. 12A, etc. Thus, as shown in FIG. 30, the contour curve 620 excludes any cartilage matter in outlining a golden femur region.

On the other hand, where the golden model is to be used in the generation of an arthritic model 36 (see block 130 of FIG. 1D) and cartilage geometry is of interest, each segmentation region the contour curve would include cartilage matter in outlining a golden femur region.

If the golden femur scan does not contain a sufficiently long shaft of the femur bone (e.g., it may be desired to segment a femur in a target MRI that may have a longer shaft), then the image segmentation can be extrapolated beyond the image to approximate a normal bone shape. This can be done because the femoral shaft is quite straight and, generally, all that is needed is to continue the straight lines beyond the MRI image, as can be understood from the extension of the contour line 620 proximal of the proximal edge of the femur image 616 of FIG. 30.

In operation 754 and as illustrated in FIG. 31A, the contour curves or splines 620 are compiled and smoothed into a golden femur mesh 624 as discussed above with respect to FIG. 13A, etc. As indicated in FIG. 30, in one embodiment, the segmentation curve 620 is a closed curve. Thus, the resulting golden femur mesh 624 is a closed mesh as depicted in FIG. 31A.

In operation 756 and as shown in FIG. 31B, the golden femur mesh 624 is converted into an open golden femur mesh 626, wherein the proximal portion of the golden femur mesh 624 is removed to create the open surface model called the open golden femur mesh 626. In other words, in operation 756 the artificial part of the femur mesh 626 is cut off, namely the proximally extending shaft portion that results from the proximal extrapolated extension of the contour line 620, so as to obtain the open golden femur mesh 626 of FIG. 31B.

In operation 758 and as indicated in FIG. 31C, regions 628, 629 of a different precision are generated for the golden femur mesh 626. For example, when segmenting the image slices 16 for the purpose of generating a golden femur mesh 626 that is used to create a 3D computer generated bone model used to show the preoperative planning ("POP") images to a surgeon, it is desirable that the bone geometry of the mesh 626 be generated with a relatively high degree of accuracy in certain regions 628 of the mesh 626 such that the resulting 3D computer generated bone model allows the physician to verify the POP with a desired degree of accuracy, while other regions 629 of the mesh 626 may not be generated to such a high degree of accuracy. For example, such a degree of accuracy in the certain regions 628 of the mesh 626 can be achieved via relatively precise image segmentation. The certain regions 628 of the mesh 626 having the relatively high degree of accuracy could include, among others, the lower shaft area, as depicted in FIG. 31C. In one embodiment, the relatively high accuracy of the certain regions 628 of the mesh 626 should allow the physician to verify the POP within 0.5 mm accuracy.

As can be understood from FIG. 31C, in one embodiment, the high precision region(s) 628 of the mesh 626 represent a portion of the distal anterior femoral shaft that would be contacted by the anterior flange of a candidate femoral implant. The rest of the mesh 626 may form the region 629 that has an accuracy that is not as precise as the high precision region 628. Such a lower precision region 629 of the mesh 626 may include the entire distal femur excluding the distal anterior region of the shaft included within the high precision region 628. Where the golden femur mesh 626 is employed to form other 3D computer generated bone models, such as, for example, the bone model 22 or arthritic model 36, the mesh 626 may have a different number of high precision regions 628 (e.g., none, one, two, three, or more such regions 628). Also, such regions 628 may have precisions that are greater or less than stated above. Finally, such regions 628 may correspond to different regions of the bone, encompass generally the entirety of the mesh surface, or include other regions in addition to the region 628 depicted in FIG. 31C.

Figure 32A:
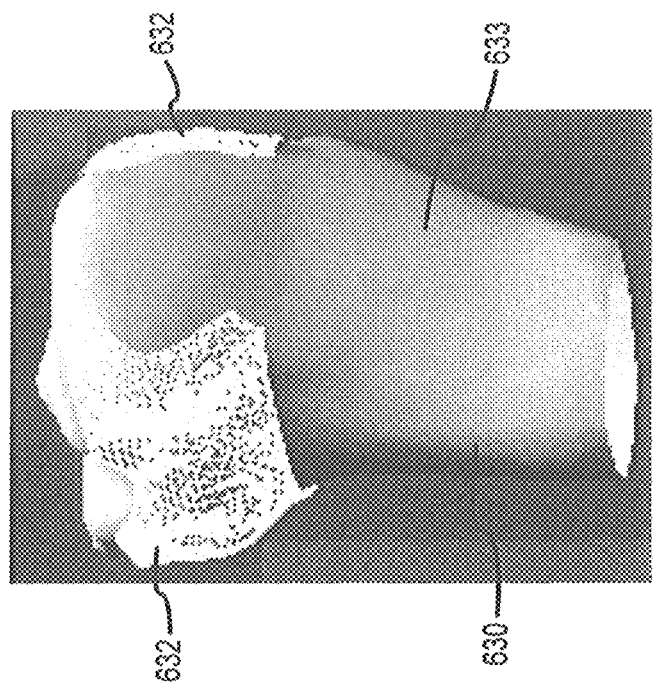
FIGS. 32A-32B are isometric views of an open golden tibia mesh with regions of a different precision indicated.
Figure 32B:
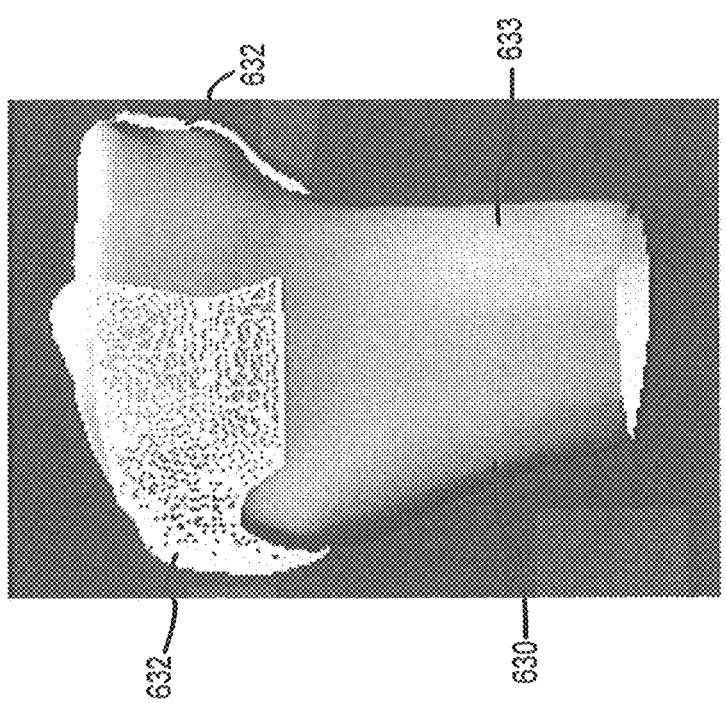

While the preceding discussion regarding the open golden bone mesh is given in the context of the open golden bone mesh being an open golden femur mesh 626, as can be understood from FIG. 32A-B, the open golden bone mesh may be an open golden tibia mesh 630 having regions 632, 633 of a different precision, all of which are generated in a manner similar to that discussed with respect to FIGS. 28-31C above.

For example, as can be understood from FIGS. 32A-32B, in one embodiment, the high precision region(s) 632 of the open golden tibia mesh 630 represent a portion of the proximal anterior tibial shaft immediately distal the tibial plateau and running medial to lateral generally proximal the tibial tuberosity. Another high precision region 632 may occupy a space similar in location and size, except on the posterior of the tibial shaft. The rest of the mesh 630 may form the region 633 that has an accuracy that is not as precise as the high precision region 632. Such a lower precision region 633 of the mesh 630 may include the entire proximal tibia excluding the regions of the shaft included within the high precision regions 632. Where the golden tibia mesh 630 is employed to form other 3D computer generated bone models, such as, for example, the bone model 22 or arthritic model 36, the mesh 630 may have a different number of high precision regions 632 (e.g., none, one, two, three, or more such regions 632). Also, such regions 630 may have precisions that are greater or less than stated above. Finally, such regions 630 may correspond to different regions of the bone, encompass generally the entirety of the mesh surface, or include other regions in addition to the regions 632 depicted in FIGS. 32A-32B.

Figure 33:
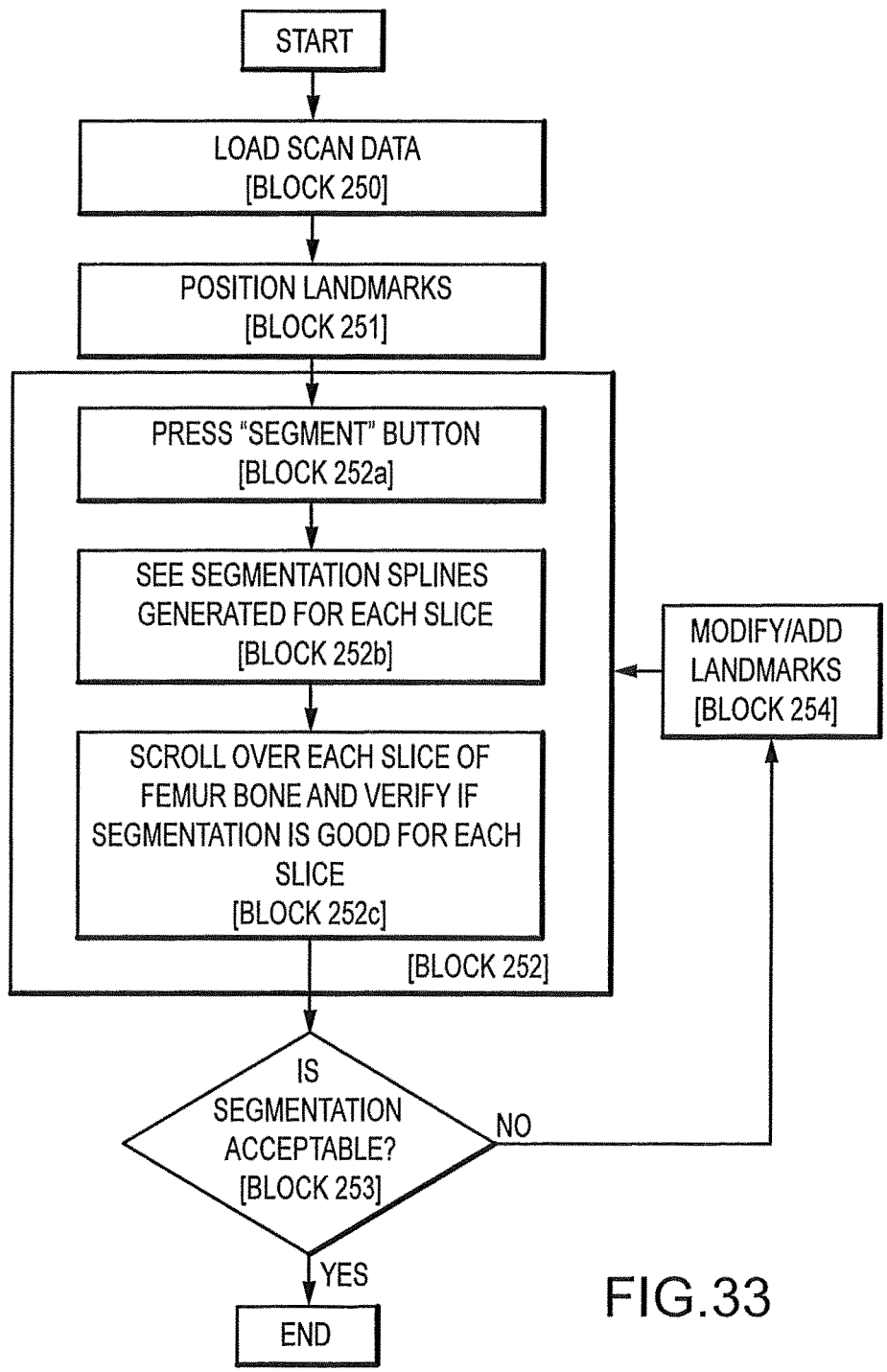
FIG. 33 is a flow chart illustrating an alternative method of segmenting an image slice, the alternative method employing landmarks.

For a discussion of an alternative embodiment of operations 250-254 of FIG. 6, reference is first made to FIG. 33, which is a flowchart illustrating the alternative embodiment of segmenting a target bone. In this example, the target bone is a femur 204, but may be a tibia 210 or any other type of bone.

Figure 34:
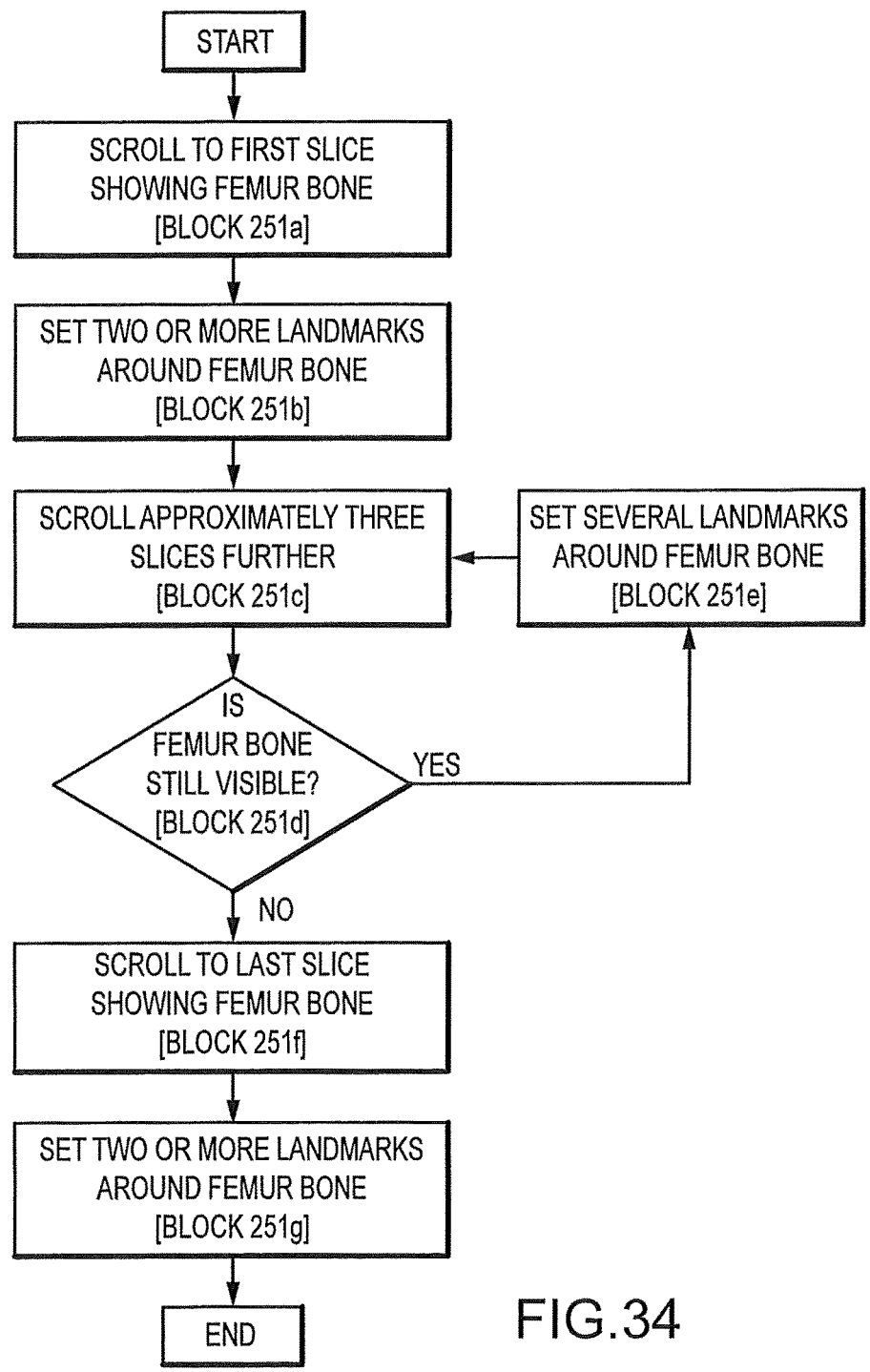
FIG. 34 is a flow chart illustrating the process involved in operation "position landmarks" of the flow chart of FIG. 33.
Figure 35A:
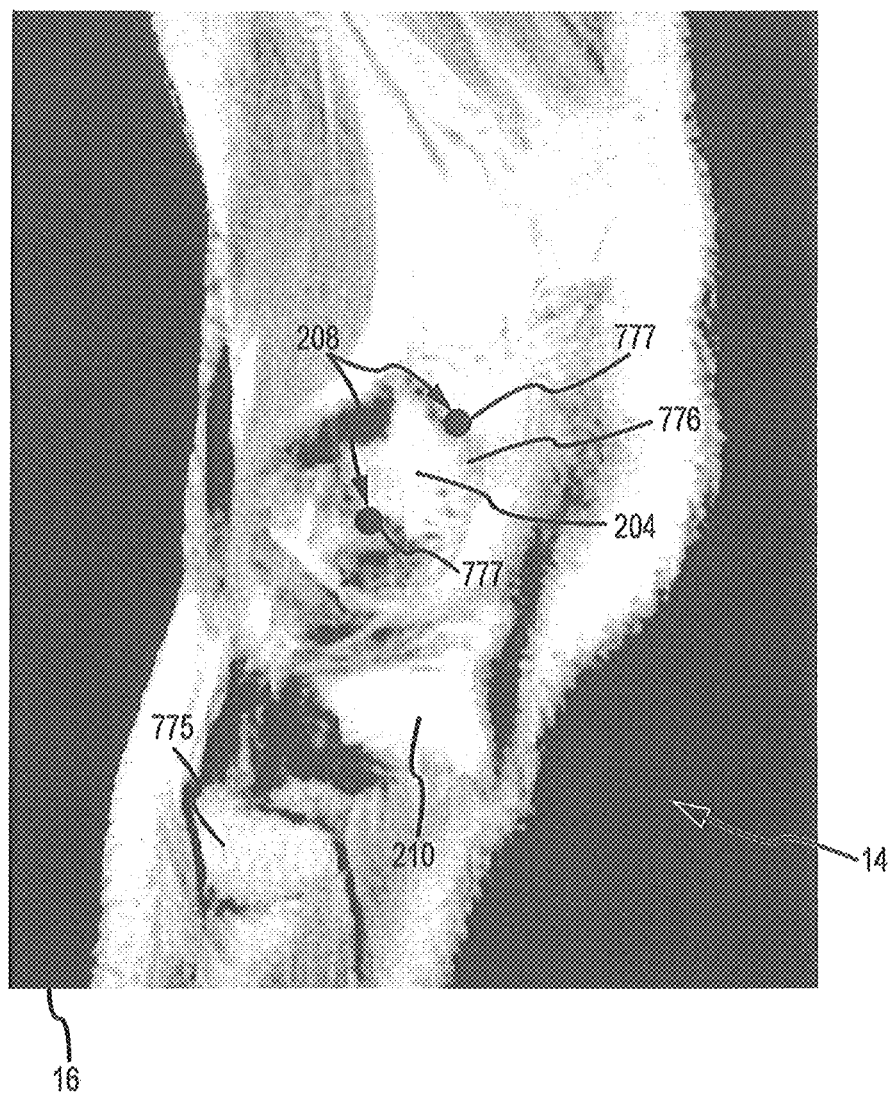
FIGS. 35A-35H are a series of sagittal image slices wherein landmarks have been placed according the process of FIG. 34.

As indicated in FIG. 33, operation 250 obtains or, more specifically, loads the scan data (e.g., scan images 16) generated by imager 8 of the patient's joint 14 to be analyzed. In operation 251 the landmarks are positioned in the scan images. In other words, as can be understood from FIG. 34, which is a flowchart illustrating the steps of operation 251, operation 251 begins with operation 251a, wherein the images 16 are scrolled through (e.g., medial to lateral or lateral to medial) to the most medial or lateral image slice were the femur bone 204 first appears, as shown in FIG. 35A, which, in this example, is a most lateral sagittal MRI image slice 16 where the femur bone 204 or, more specifically, the lateral epicondyle 776 first appears. Since the slice 16 of FIG. 35A is the most lateral image where bone has begun to appear, the fibula 775 can be seen adjacent the tibia 210 in such instances where the image slice is positioned so as to show both the femur 204 and the tibia 210. In operation 251b, two or more landmarks 777 are positioned on the outer rim of the black cortical bone 208 of the image slice 16 depicted in FIG. 35A. As is the case with all of the images depicted in FIGS. 35A-35H, in one embodiment, the landmarks are placed via an operator sitting at a work station. In one embodiment, the operator or user is able to add landmarks by simply clicking onto the slice image, the landmark (point) being created at the exact coordinates where the click has occurred. The operator is able to move existing landmarks within the slice by selecting them and moving them with the mouse, a keyboard, a pen-and-tablet system, or similar. The user is able to delete existing landmarks by selecting them and indicating to the software that they should be deleted.

In another embodiment, a touch-screen surface may be used to provide input and display for interactive editing of landmarks and segmentation curves. Specialized gestures may be adopted for various editing operations.

In another embodiment, a spatial input device may be used for manipulation of landmarks, segmentation curves, and other operations involving POP and jig design activities.

Figure 35B:
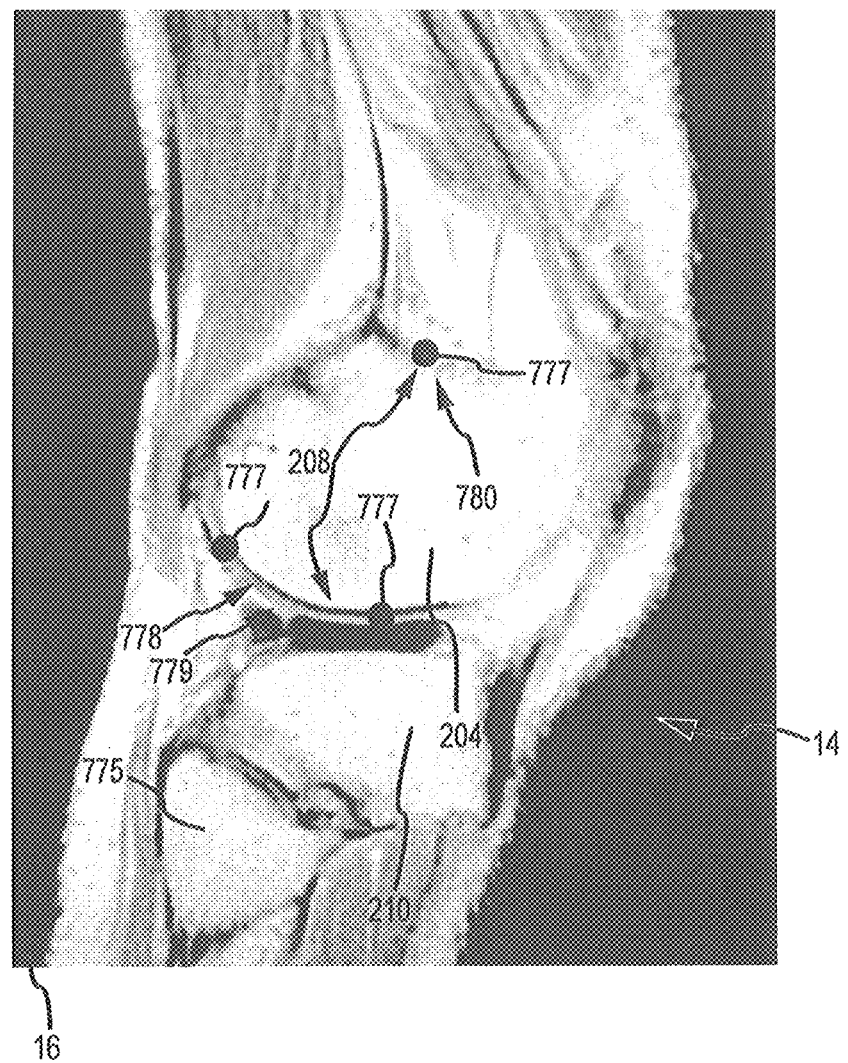

In operation 251c, the image slices 16 are scrolled lateral to medial through approximately three slices 16 further to a new image slice 16 and, at operation 251d, it is determined if the femur bone 204 is still visible in the new image slice 16, which is depicted in FIG. 35B. If so, then operation 251e adds landmarks 777 to the new image slice 16 as indicated in FIG. 35B. Specifically, as indicated in FIG. 35B, this new image slice 16 may show the femur lateral condyle 778 and be the first image slice having a clear boundary 779 of the femur lateral condyle. As can be seen in FIG. 35B, the fibula 775 and tibia 210 are also more fully shown. Landmarks 777 are set on the clear boundary 779 of the outer rim of the dark cortical bone of the femur lateral condyle, and an additional landmark 777 is set on the opposite side 780 on the rim of the black cortical bone 208. As is the case with the placement of landmarks 777 in any of the images 16, more or fewer landmarks 777 may be placed along the rim of the black cortical bone depicted in the image 16, including landmarks being placed on the rim of the black cortical cone of the entirety of the distal femur, including the distal femur condyle and distal femur shaft.

Figure 35C:
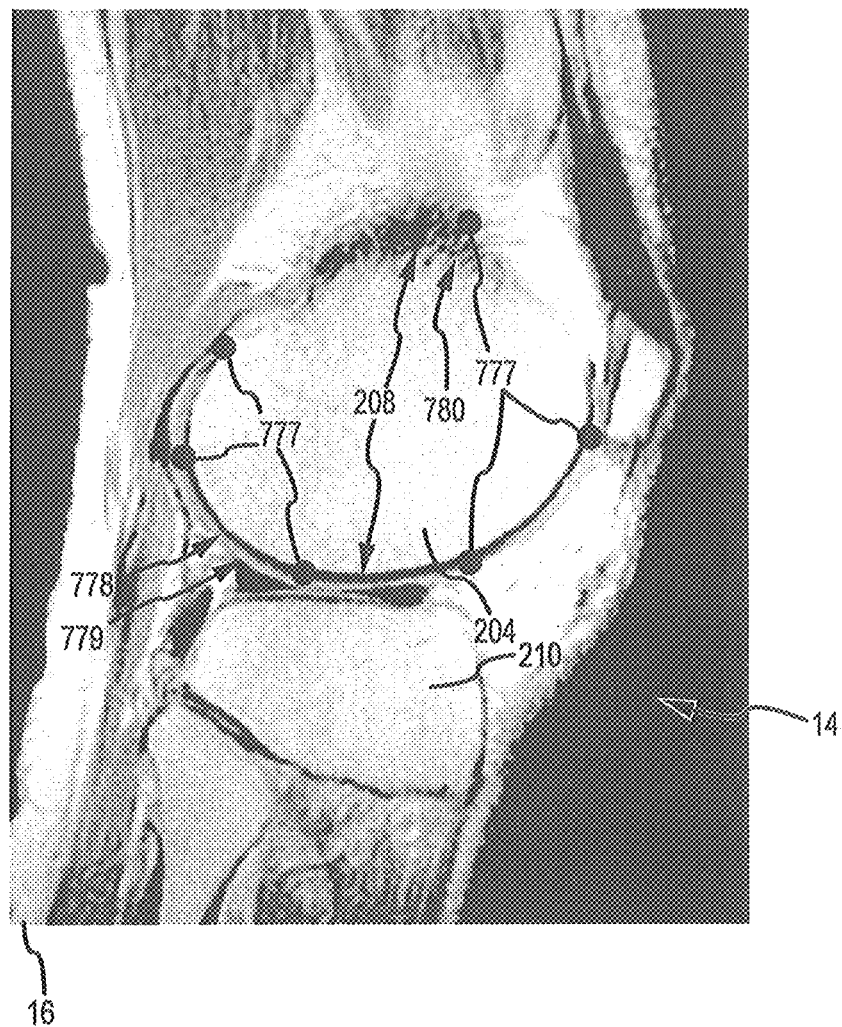

Operations 251c through 251e are repeated to set landmarks 777 at the bone contour boundaries of approximately every third image slice 16 moving lateral to medial until eventually at operation 251d it is determined that bone no longer appears in the present image slice. Thus, as operation 251 of FIG. 33 loops through operations 251c-251e of FIG. 34, landmarks 777 are set at the bone contour boundaries in each of the sagittal image slices 16 depicted in FIGS. 35C-35H, which are, respectively, approximately every third sagittal image slice 16 tabbing lateral to medial through all the sagittal image slices 16 loaded in operation 250 of FIG. 33. Thus, as shown in FIG. 35C, which represents a sagittal image slice 16 approximately three slices more medial than the image slice 16 of FIG. 35B, the femur lateral condyle 778 has a clear bone contour boundary 779, and landmarks 777 are set along the boundary 779 on the rim of the dark cortical bone 208. A landmark 777 is also set on the top region 780 of the cortical bone boundary 779 where the bone contour boundary is less clear, the landmark being positioned on the rim of the dark cortical bone 208.

Figure 35D:
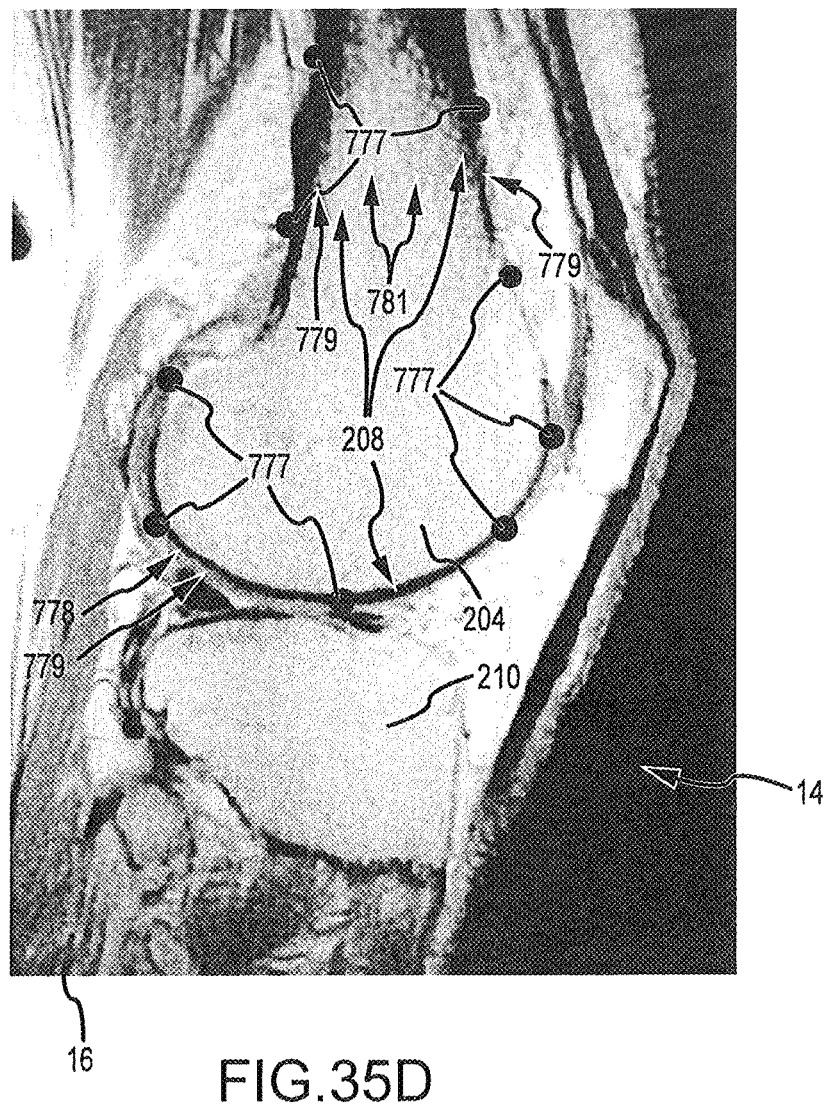

As illustrated in FIG. 35D, which represents a sagittal image slice 16 approximately three slices 16 more medial than the image slice 16 of FIG. 35C, the femur shaft 781 has now appeared in an image slice 16 and both the femur shaft 781 and femur lateral condyle 778 have clear bone contour boundaries 779. Landmarks 777 are set along the bone contour boundaries 779 on the rim of the dark cortical bone 208.

Figure 35E:
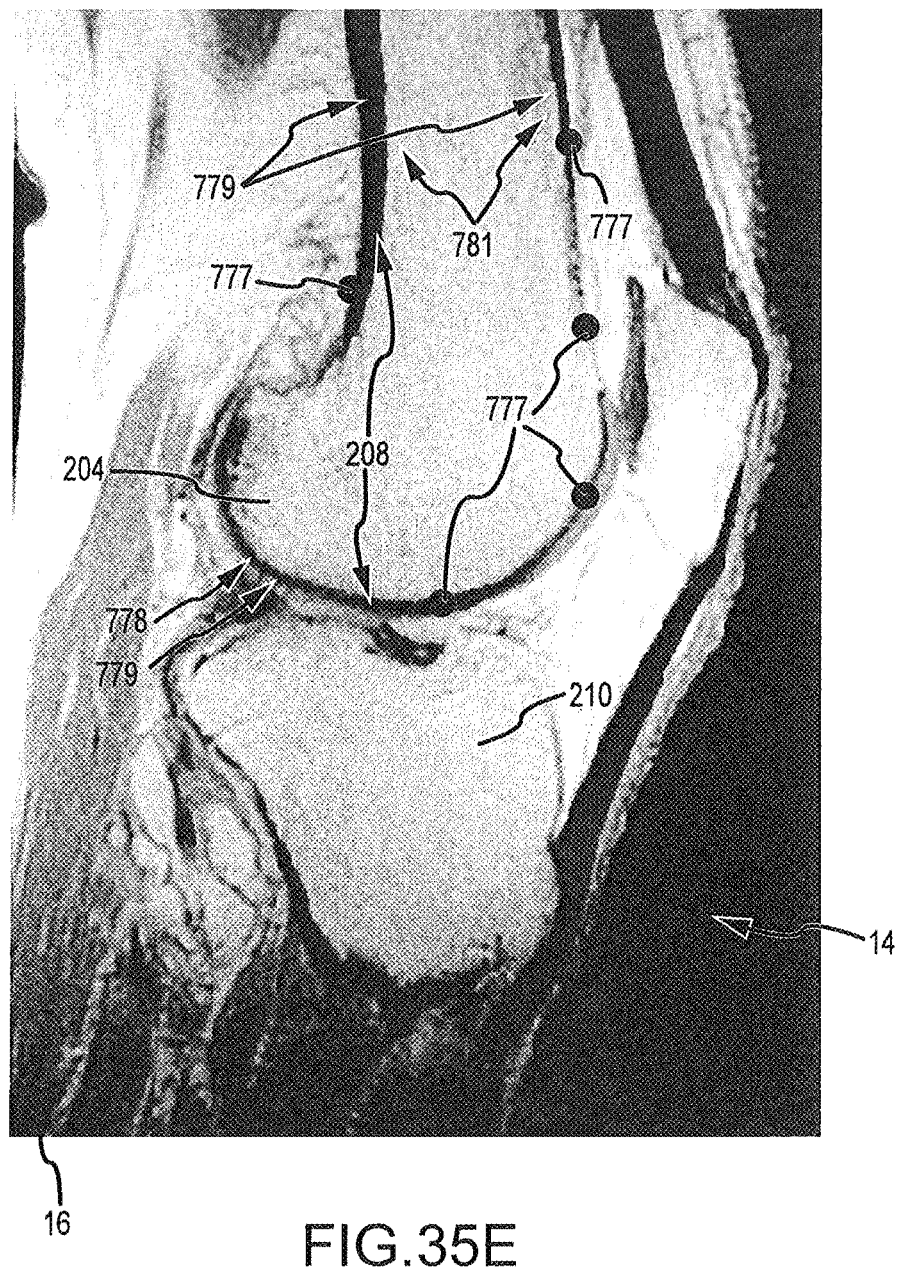

As shown in FIG. 35E, which represents a sagittal image slice 16 approximately three slices 16 more medial than the image slice 16 of FIG. 35D, the femur lateral condyle 778 is starting to disappear, and part of its cortical bone contour boundary 779 is not clear. Landmarks 777 are only set outside the dark cortical bone 208 in the regions where the contour boundary 779 is clear.

Figure 35F:
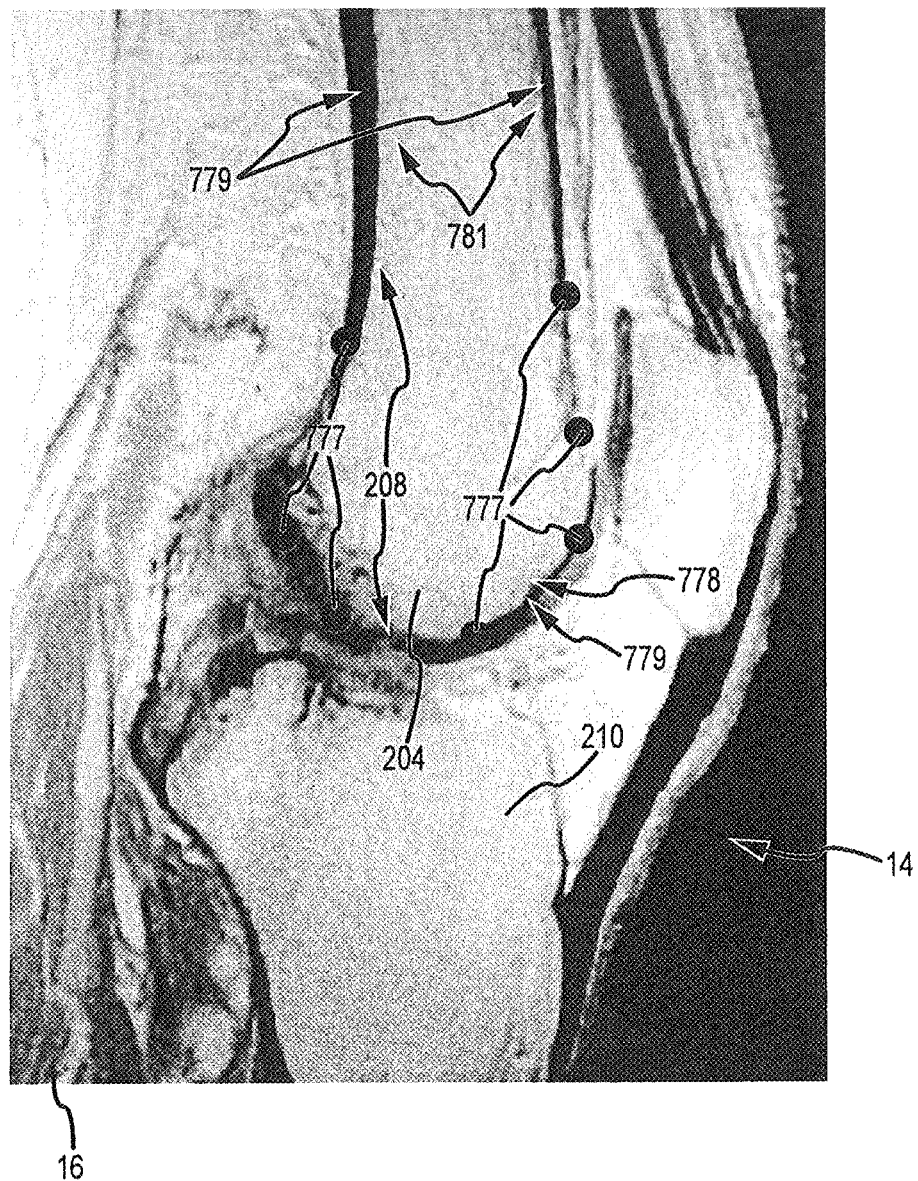

As illustrated in FIG. 35F, which represents a sagittal image slice 16 approximately three slices 16 more medial than the image slice 16 of FIG. 35E, the bone contour boundary 779 has become less clear as the femur lateral condyle 778 has decreased in size as compared to the femur lateral condyle 778 of slice 16 in FIG. 35E. The slice 16 of FIG. 30F is just lateral of the trochlear groove 782 between the femur lateral condyle 778 and femur medial condyle 783. The bone contour boundary 779 is clear in the anterior region of the femur lateral condyle 778 and two landmarks 777 are placed there. Additional landmarks 777 are set along the bone contour boundaries 779 on the rim of the dark cortical bone 208.

Figure 35G:
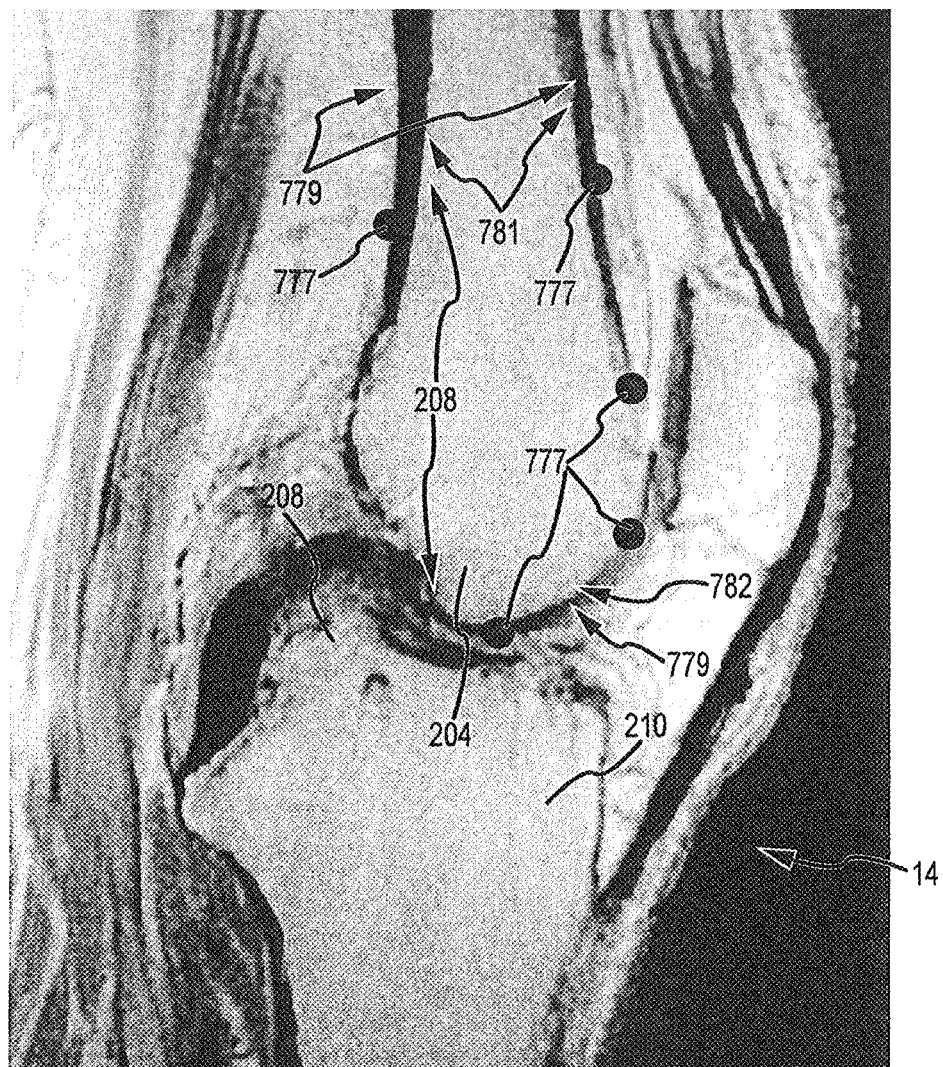

As indicated in FIG. 35G, which represents a sagittal image slice 16 approximately three slices 16 more medial than the image slice 16 of FIG. 35F, landmarks 777 are set along the bone contour boundaries 779 on the rim of the dark cortical bone 208. The slice 16 of FIG. 35G is in the trochlear groove 782 between the femur lateral condyle 778 and femur medial condyle 783. The intercondylar eminence 784 of the tibia 210 can be seen in the slice 16 of FIG. 35G.

Figure 35H:
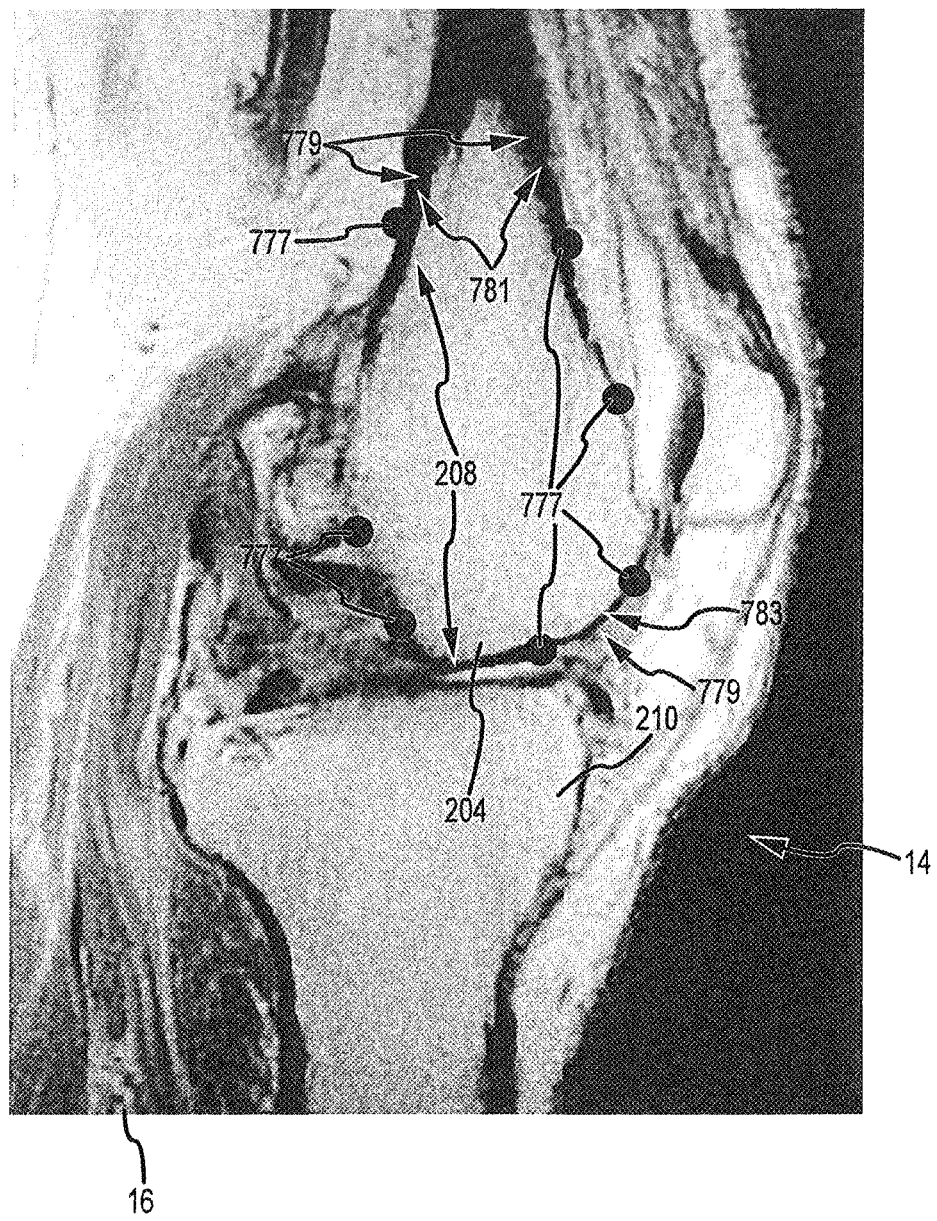

As indicated in FIG. 35H, which represents a sagittal image slice 16 approximately three slices 16 more medial than the image slice 16 of FIG. 35G, the femur shaft 781 has begun to disappear and the femur medial condyle 783 has begun to appear as the slice of FIG. 35H is medial of the trochlear groove 782 depicted in the slice of FIG. 35G. The bone contour boundary 779 is clear in the anterior region of the femur medial condyle 783 and two landmarks 777 are placed there. Additional landmarks 777 are set along the bone contour boundaries 779 on the rim of the dark cortical bone 208.

As stated above, operations 251c through 251e continue to be repeated as the slices 16 continue to be tabbed through lateral to medial to set landmarks 777 at the bone contour boundaries of approximately every third image slice 16 until eventually at operation 251d it is determined that bone no longer appears in the present image slice. Operation 251f then scrolls medial to lateral through the image slices 16 until arriving at the image slice 16 where the most medial portion of the femur is depicted. Operation 251g then sets two or more landmarks 777 around the bone (e.g., the medial epicondyle) in a manner similar to that depicted in FIG. 35A with respect to the lateral epicondyle 776. This is the end of operation 251 and, as can be understood from FIG. 33, operation 252 begins by pressing the "segment" button (operation 252a), which causes segmentation lines to be generated for each slice 16 with landmarks 777 (operation 252b) in a manner similar to that illustrated and discussed above with respect to FIGS. 7A-7K or as now will be discussed below beginning with FIG. 36.

When positioning landmarks, a user needs to distribute them over the cortical bone outer surface, favoring areas where the cortical bone boundary is sharp and is more orthogonal to the slice plane, particularly favoring certain "important" areas of the bone surface (where importance is dictated by eventual contact between bone and implant or by other requirements from POP procedure.) The user should only sparsely mark up the remaining parts of the bone, particularly where there is a lot of volume averaging (and/or the bone surface is more parallel to slice plane.) While the image slices depicted in FIGS. 35A-35H are MRI generated image slices, in other embodiments the imaging slices may be via other medical imaging methods, such as, for example, CT.

In one embodiment, the landmark-driven segmentation algorithm described below is deliberately sensitive to the number of landmarks (points) placed at a given area of the bone. So for instance, if the user desires the auto-generated bone mesh to very accurately pass through particular spots on the slice, the user can place more than one landmark on that same spot or very near that spot. When there is a high concentration of landmarks in a small area of the bone, the auto-generated mesh will be biased to more accurately model that area. The software indicates to the user, making it visible at a glance whenever more than one landmark is located within the same small area of the image.

In one embodiment, instead of putting landmarks in every three slices, a user may position landmarks in every slice but use three times fewer landmarks in each slice. The result of the segmentation usually varies very little depending on how a user distributes landmarks around the bone surface as long as the entire surface is covered.

While much of the following discussion takes place in reference to the segmentation of a femur (operation 252 of FIG. 6), the concepts discussed herein are readily applicable to the segmentation of a tibia (operation 258 of FIG. 6). Additionally, the concepts discussed herein are readily applicable to both the left or right knee. Different golden template data may be used to segment the left tibia, right tibia, left femur or right femur for bone models 22 or planning models 28. Additionally, other embodiments may segment other models and or joints, including but not limited to, arthritic models 36, hip joints, elbow joints, etc. by using an appropriate golden template of the feature of interest to be segmented.

Figure 36:
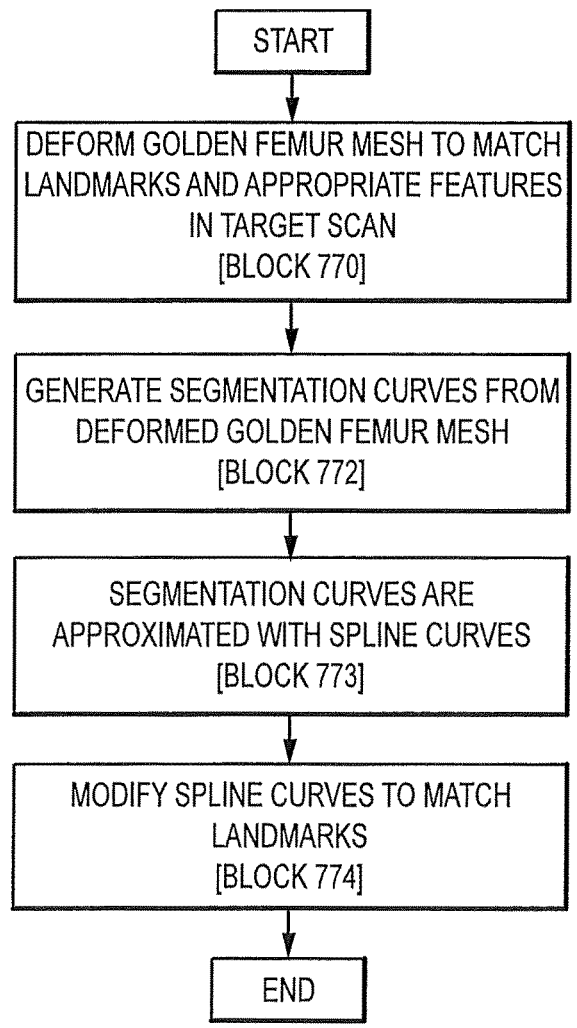
FIG. 36 is a flowchart illustrating the process of segmenting the target images that were provided with landmarks in operation "position landmarks" of the flow chart of FIG. 33.

As shown in FIG. 36, which is a flowchart illustrating the process of segmenting the target images 16 that were provided with landmarks 777 in operation 251, the full or entire golden femur mesh 626, including its regions 628, 629 in FIG. 31C, is deformed in operation 770 to match landmarks 777 and appropriate features, such as, for example, the outer edges of dark cortical bone, in the target scan images 16.

As discussed below with respect to FIG. 37, a method is provided for mapping the golden femur mesh into the target scan using registration techniques. Registration may be thought of as an optimization problem with a goal of finding a spatial mapping that aligns a fixed object with a target object. Generally, several registration operations may be performed, first starting with a low-dimensional transformation group to find a rough approximation of the actual femur location and shape in the target image. This may be done to reduce the chance of finding wrong features instead of the femur of interest. For example, if a free-form deformation registration was initially used to register the golden femur mesh to the target scan data, the template might be registered to the wrong feature, e.g., to a tibia rather than the femur of interest. A coarse registration may also be performed in less time than a fine registration, thereby reducing the overall time required to perform the registration. Once the femur has been approximately located using a coarse registration, finer registration operations may be performed to more accurately determine the femur location and shape. By using the femur approximation determined by the prior registration operation as the initial approximation of the femur in the next registration operation, the next registration operation may find a solution in less time. It is to be understood that similar considerations apply to segmentation of other entities (and not just the femur.)

In one embodiment, each registration operation may employ a registration framework. The registration framework may be based on three general blocks. The first block defines a transformation model (or a class of transforms) T(X), which may be applied to coordinates of a fixed (or reference) object (e.g., a golden femur template) to locate their corresponding coordinates in a target image space (e.g., an MRI scan). The second block defines a metric, which quantifies the degree of correspondence or similarity between features of a fixed (or reference) object and the target object (that is landmarks and appropriate target image features) achieved by a given transformation. It should be noted that instead of a metric that defines the degree of correspondence, an opposite to it function is defined, which is call the defect function. The third block defines an optimization algorithm (optimizer), which tries to maximize the reference and the target objects similarity (or minimize the opposite defect function) by changing the parameters of the transformation model. Thus, as discussed below in detail with reference to FIG. 37, in every registration operation 770a-770c and 770e there is a need to specify three blocks: (1) class of transforms; (2) metric (or defect) function; and (3) optimization algorithm. In one embodiment, the same third block may be used in all four registration steps. For instance, a gradient descent optimizer or conjugate gradient descend optimizer may be used. Alternatively, any other appropriate optimization algorithm, such as Monte Carlo, simulated annealing, genetic algorithms, neural networks, and so on, may be used.

Figure 37:
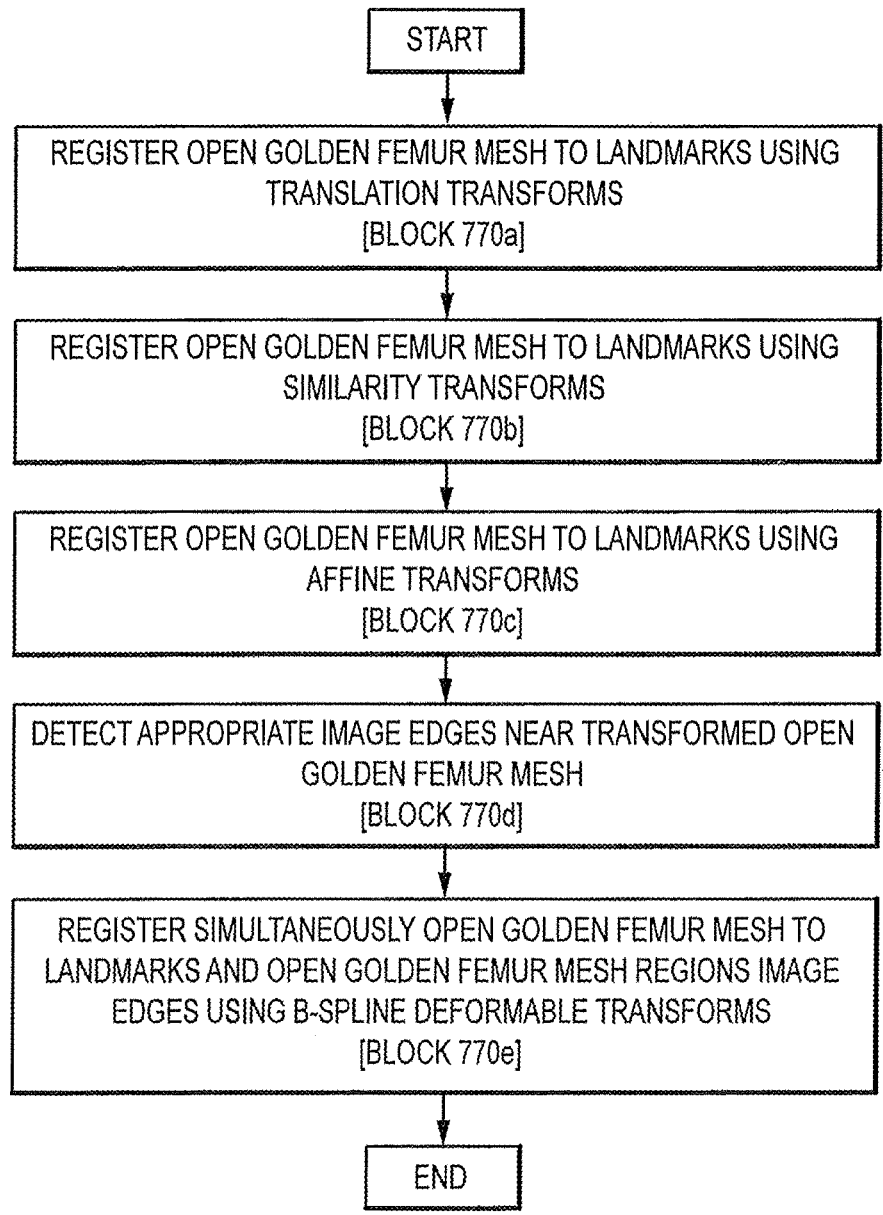
FIG. 37 is a flowchart illustrating the process of operation "Deform Golden Femur Mesh" of FIG. 36, the process including mapping the golden femur mesh into the target scan using registration techniques.

As shown in FIG. 37, which is a flowchart illustrating the process of operation 770 of FIG. 36, in operation 770a translation transforms are used to register the full or entire open golden femur mesh 626 to the landmarks 777. More specifically, in operation 770a, the open golden femur mesh 626 may be approximately registered to landmarks 777 using a coarse registration transformation. In one embodiment, this may be done by finding appropriate translation transform parameters that minimize translation misalignment with landmarks of the reference open golden femur mesh mapped onto the target femur of the target image, where landmarks 777 are positioned. This coarse registration operation typically determines an approximate femur position in the MRI scan. During this operation, the reference open golden femur mesh 626 may be overlapped with the target femur of the target image using a translation transformation to minimize translational misalignment of the femurs. A translation transform, translates (or shifts) all the points in 3D space by the same 3D vector. That is, the reference femur may be mapped into the target image space by shifting the reference open golden femur mesh along one or more axes in the target image space to minimize misalignment. During this operation the reference object is not rotated, scaled or deformed. In one embodiment, three parameters for the translation transformation may be generated: one parameter for each dimension that specifies the translation for that dimension. In one embodiment, the final parameters of the translation transform minimizing the misalignment of the mapped reference femur image coordinates into the target image space may be found using a gradient descent optimizer. In other embodiments, other types of optimizers may be utilized, such as for instance an Iterative Closest Point (ICP) algorithm.

Optimization of mesh alignment with respect to landmarks is based on minimizing a cost function D, which in one embodiment can be the sum, across all landmarks, of the squared distance from each landmark point 777 to the transformed open golden mesh. The same cost function may be used for steps 770a-770c. Methods for computing this cost function and its gradient are covered in more detail later in this Detailed Description.

After an optimal transform has been found, it is applied to all the golden femur data (i.e., the closed golden femur mesh 624, open golden femur mesh 626, and golden femur mesh regions 628, 629. The next operation (i.e., operation 770b of FIG. 37, which is discussed immediately below) is then started with transformed golden femur data. As can be understood from the following discussion, after every consecutive operation 770a, 770b, 770c and 770e of FIG. 37, the transform found during the registration step is applied to all the golden femur data. As a result, after each operation the golden femur data is successively made more closely aligned with the femur in the target image.

In operation 770b of FIG. 37 similarity transforms are used to register the full or entire open golden femur mesh 626 to the landmarks 777. Specifically, operation 770b further refines the object's registration determined by operation 770a. This may be done by approximately registering the open golden femur mesh 626 to landmarks 777 using a similarity transformation. In one embodiment, a similarity transformation may be performed in 3D space. The reference open golden femur mesh may be rotated in 3D, translated in 3D and homogeneously scaled to map its coordinates into the target MRI scan data to minimize misalignment between the open golden femur mesh and the landmarks in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation, and three parameters specify a vector that represents the 3D translation in each dimension. A versor is a unit quaternion that provides a convenient mathematical notation for representing rotations of objects in three dimensions.

In one embodiment, local minimization techniques may be employed with the similarity transformation to obtain a refined registration of the reference open golden femur mesh onto the target MRI scan that is not far from the registration of the reference open golden femur mesh onto the target MRI scan found in previous operation 770a and used as the initial starting approximation. For instance, gradient descent, conjugate gradient descent, or ICP optimization may be used. After the best transform is found for operation 770b of FIG. 37, the transform is applied to the golden femur data in a manner similar to that of operation 770a.

In operation 770c of FIG. 37 affine transforms are used to register the full or entire open golden femur mesh 626 to the landmarks 777. Specifically, operation 770c further refines the image registration determined by operation 770b. In one embodiment, an affine transformation may be used to register the open golden femur mesh 626 to landmarks 777 in the target MRI scan data. In one embodiment, the approximate femur registration found during operation 770b may be used as the initial starting approximation for the affine transformation of operation 770c.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the open golden femur mesh with landmarks may be found using again local minimization techniques, such as gradient descent or conjugate gradient descent optimization.

After the best transform is found for operation 770c of FIG. 37, the transform is applied to the golden femur data. The transformed golden femur data from operation 770c is then employed in the preparatory step of detecting appropriate image edges, namely, operation 770d, which is discussed below. Those edges will be later used in operation 770e of FIG. 37, as discussed below. The transformed golden femur data from operation 770c is used as reference data similar to the previous operations.

A discussion of image edges is now provided before discussing the details of operation 770d of FIG. 37. Image edges consist of those points in the image where the image contrast significantly changes between neighbor pixels (or voxels) and this contrast change is consistent along several neighboring points distributed over a smooth curve. For example, points that lie between the light cancellous bone pixels and dark cortical bone pixels form an image edge. Similarly, the points that lie between the dark cortical bone pixels and the grayish cartilage pixels form an image edge. Yet a configuration involving a one-pixel black spot and the surrounding light pixels does not form an image edge because the light points represent a curve with too much curvature, whereas the dark point represents a curve that is too discontinuous (spanning only a single voxel.) Usually there is an image edge that separates one type of the body tissue from a neighboring different type of body tissue.

The purpose of segmenting an image is to be able to separate in the image certain body tissues from the surrounding tissues. Ideally, the segmentation boundaries (or curves) should lie mostly in the image edges. A general MRI or CT image contains lots of edges separating various body tissues from the neighboring tissues. Yet when segmenting, there is only interest in certain tissues and thus particular edges only. Operation 770d is intended to find those edges that are of interest for segmenting a particular body object.

In particular in case of the segmentation of any of the versions of the femur planning model 22, 28 (shown in blocks 110 and 115, respectively, of FIG. 1C), operation 770d of FIG. 37 will find the edges that separate the cortical femur bone from the outside knee tissues (i.e., the tendons, ligaments, cartilage, fluid, etc.). In some embodiments, operation 770d will not find the edges that separate the femur cancellous bone from the femur cortical bone. In other embodiments, operation 770d will find the edges that separate the femur cancellous bone form the cortical bone.

Operation 770d may also find some edges that are of no interest to the femur planning segmentation. Most of those edges of no interest will lie at significant distance from the femur boundary surface and, as a result, the edges of no interest will not influence the next operation in the algorithm, namely, operation 770e of FIG. 37.

In some cases, some of the edges of no interest might happen to be very close to the edges of interest. Such nearby edges of no interest are likely to be the edges separating the cartilage tissue from the other tissues outside the bone. Such edges might adversely influence the next operation in the algorithm, namely, operation 770e of FIG. 37, and lead to inaccurate segmentation. In some embodiments, this inaccuracy can be remedied by the user providing extra landmarks 777 in the area that is likely to cause such inaccuracies or manually fixing the spline curves during the verification and adjustment operations.

The result of the operation 770e of FIG. 37 will be a 3D image of the same size as the target scan data. The resulting 3D image can be called an edges image. The voxels in the edges image correspondent to strong edges will have highest intensities, the non-edge voxels will have low intensities, and the voxels correspondent to weak edges will have intermediate intensities. Discussion of the operation 770d of FIG. 37 is now provided.

Figure 38A:
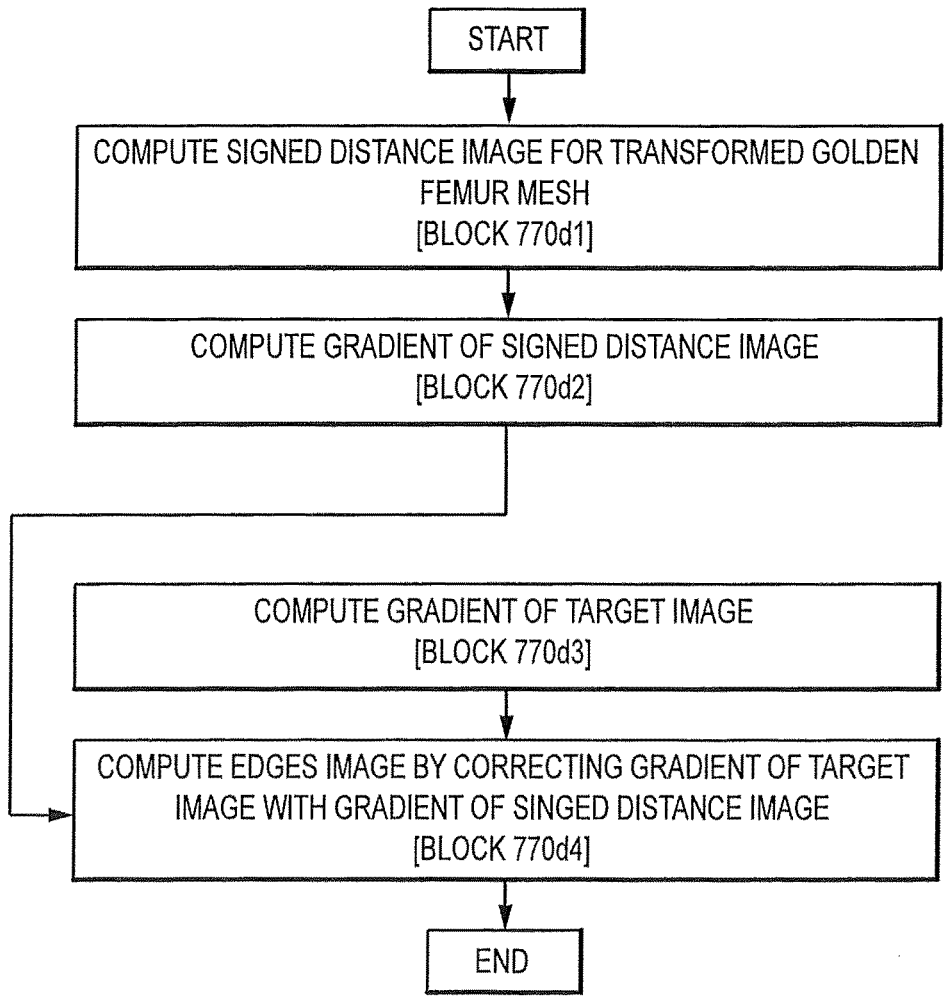
FIG. 38A is a flowchart illustrating the process of operation "Detect Appropriate Image Edges" of FIG. 37.

In operation 770d of FIG. 37 appropriate edges of the target images are detected near the transformed open golden femur mesh 626. For example, as indicated in FIG. 38A, which is a flowchart illustrating the process of operation 770d of FIG. 37, in operation 770d1 the signed distance image is computed for the transformed golden femur mesh 626. A signed distance map is a distance map of a region in 2D (or 3D) and is a function in 2D (or 3D). The signed distance value for a point equals the distance from the point to the boundary of a region. A signed distance value can have a positive or negative value. For example, when a point is inside the region, the signed distance value of the point is the distance from the point to the boundary of the region in the form of a negative value. When a point is outside the region, the signed distance value of the point is the distance from the point to the boundary of the region in the form of a positive value. If the signed distance map function is computed in a regular grid of points in 2D (or 3D) correspondent to image pixels (or voxels) and stored as a 2D (or 3D) image representation, the result can be said to be a 2D (or 3D) signed distance image.

Thus, from the preceding discussion, it can be understood that the signed distance for a watertight surface is a function that has absolute values equal to the regular (Euclidean) distance, but the values also have a sign. The sign is negative for the points inside the surface, and the sign is positive for the points outside the surface. The open golden femur mesh 626 transformed in operations 770a-770c of FIG. 37 is used in operation 770d1 of FIG. 38A. By the time of operation 770d1, the open golden femur mesh 626 may quite closely match the landmarks 777 positioned in the target image and, as a result, the open golden femur mesh 626 also matches quite closely the target femur bone in the target image. Since the golden femur mesh 626 is a watertight mesh, the mask image marking may be computed as "1" for all voxels that lie inside the open golden femur mesh 626 and as "0" for all the voxels that lie outside the mesh. The Signed Danielsson Distance Map Image Filter from the ITK library can then be used to compute the signed distance to the mask boundary, which is approximately the same as the signed distance to the mesh. It may be desired to have greater accuracy close to the mesh. If so, then for the voxels where the absolute value of the signed distance is small, the distance to the mesh may be recomputed by finding the closest points via a more exact method, as detailed later in this specification.

In operation 770d2 the gradient of the signed distance image is computed. As can be understood from FIG. 38B, the gradient of the signed distance image contains a vector 1000 in every voxel. The vector 1000 represents the gradient of the signed distance image at the particular point of the voxel. Because the signed distance image represents the signed distance to the transformed open golden femur mesh 626, which follows closely the boundary of the femur bone in the target image, the gradient image has gradient vectors nearly orthogonal to the boundary of the target femur in the voxels close to the boundary.

Figure 38B:
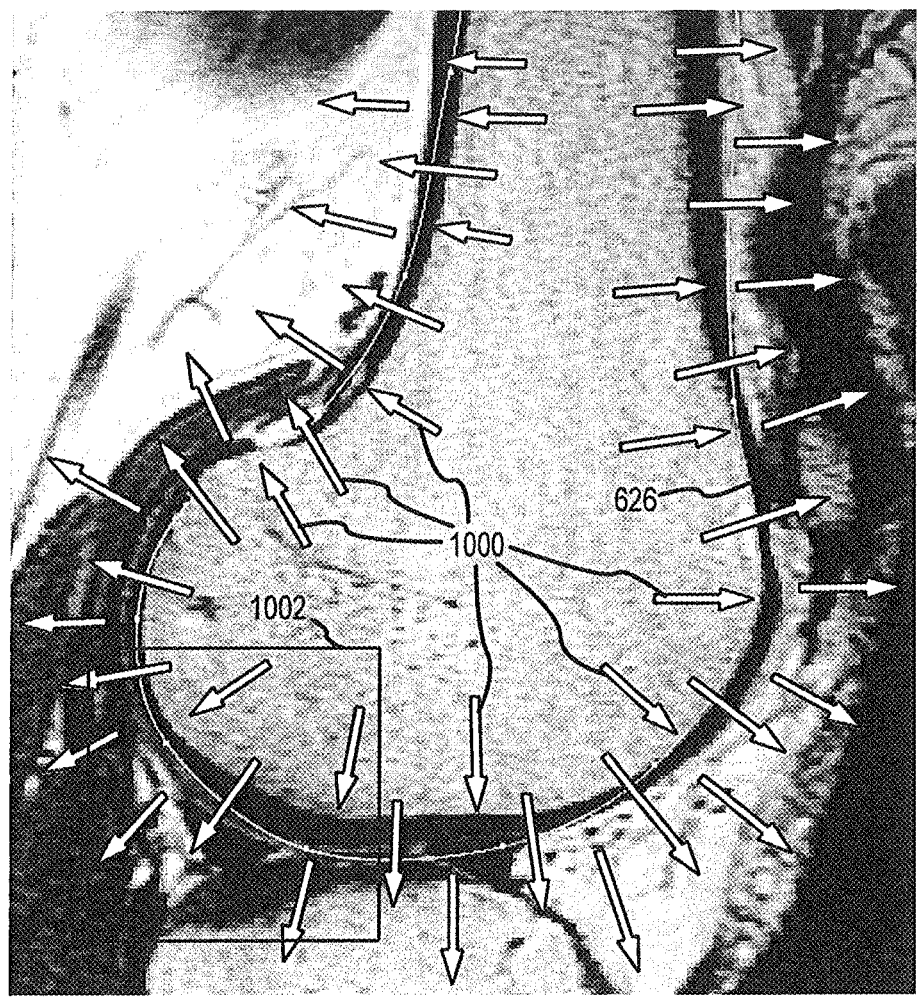
FIG. 38B is an image slice with a contour line representing the approximate segmentation mesh surface found in operation 770c of FIG. 37, the vectors showing the gradient of the signed distance for the contour.

The contour line 626 in FIG. 38B represents the approximate segmentation mesh surface found in the previous registration step of operation 770c of FIG. 37. The vectors 1000 show the gradient of the signed distance for the contour 626. The starting end of the vector 1000 is the point or voxel where the vector 1000 is computed. The gradient of a signed distance has a vector direction in every point or voxel toward the closest point in the contour 626. Vectors 1000 are oriented from inside to outside the contour 626. Each vector 1000 has a unit length.

In operation 770d3 the gradient of the target image is computed. As can be understood from FIG. 38C, which is an enlarged view of the area in FIG. 38B enclosed by the square 1002, the gradient of the target image has gradient vectors 1004 orthogonal to the edges 1006, 1008 in the target image, and the length of those vectors 1004 is larger for stronger edges and smaller for weaker edges. Such vectors 1004 are always oriented from the darker image region to the lighter image region or, in other words, from darker pixels towards brighter pixels. The vectors 1004 are longer where the contrast is higher. For purposes of illustration in FIG. 38C, the vectors 1004 illustrated are only long vectors corresponding to high contrast pixels associated with strong edges. The gradient vectors 1004 can be used to identify the outer cortical bone boundary 1006 and other edges 1008, 1010 that are not of interest for the analysis.

Figure 38C:
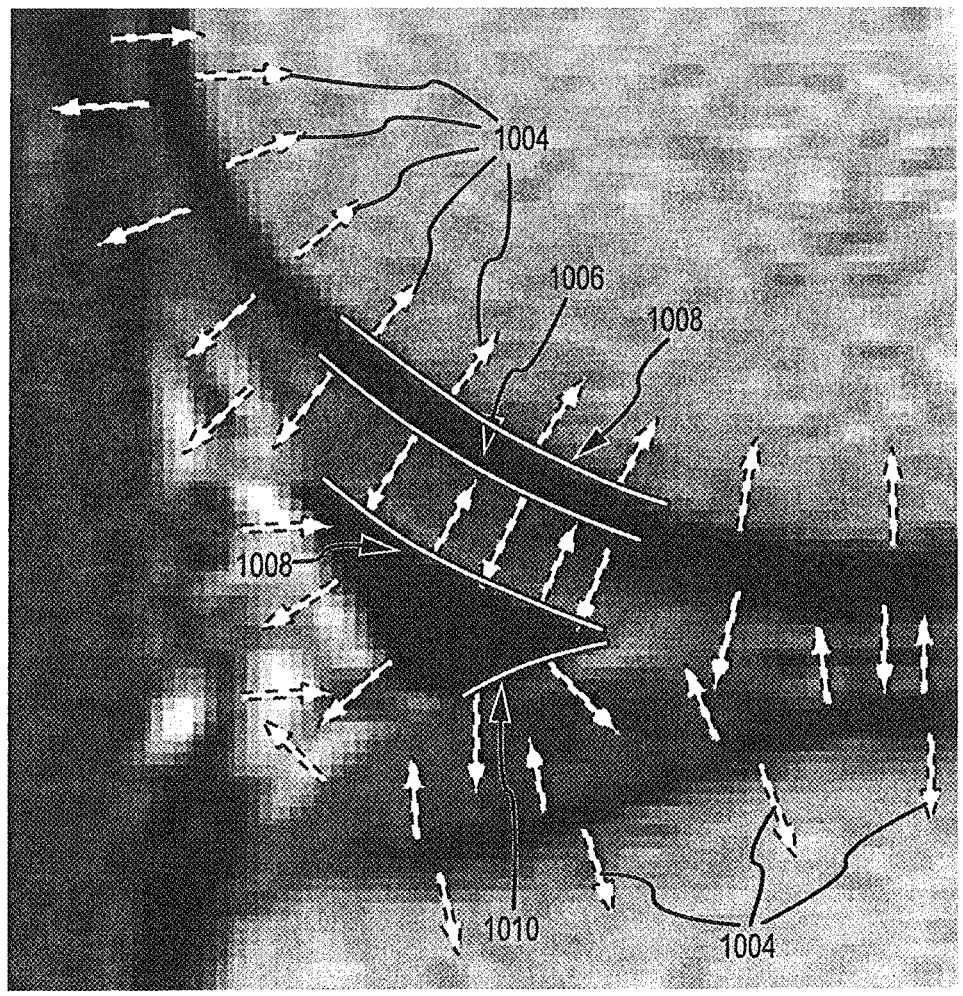
FIG. 38C is an enlarged view of the area in FIG. 38B enclosed by the square 1002, the vectors showing the computed gradient of the target image.

Finally, operation 770d of FIG. 37 is completed via operation 770d4 of FIG. 38A, wherein the edges image is computed by correcting the gradient of the target image with the gradient of the signed distance image. As can be understood from FIG. 38D, the edges image is computed by combining the results from operations 770d2 and 770d3. Depending on the type of 3D computer generated bone model being generated from the segmented images, different boundary edges may be of relevance. For example, if the images are being segmented to generate a bone model 22, the boundary edges that are of interest contain dark cortical voxels inside and lighter cartilage or other voxels outside. As a result, the voxels that are of interest are those voxels that have similarly oriented gradients 1000, 1004 computed in operations 770d2 and 770d3 as shown in FIGS. 38B and 38C, respectively. In every voxel the vector 1004 from operation 770d3 is projected onto the vector 1000 from operation 770d2. When the projection of image gradient vector onto a signed distance gradient vector points in the same direction as the signed distance vector, its magnitude is taken as the voxel value for the resulting edges image. When it points in the opposite direction (or has no magnitude at all), "0" is taken as the voxel value for the resulting edges image.

The resulting edges image has high values in the target femur cortical bone outer boundary 1006. However, the edges image does not have many other high values close to the transformed open golden femur mesh with one exception, namely, the voxels on the boundary between the target femur cartilage and the outsight bright voxels (for example fluid voxels) might have high values.

Figure 38D:
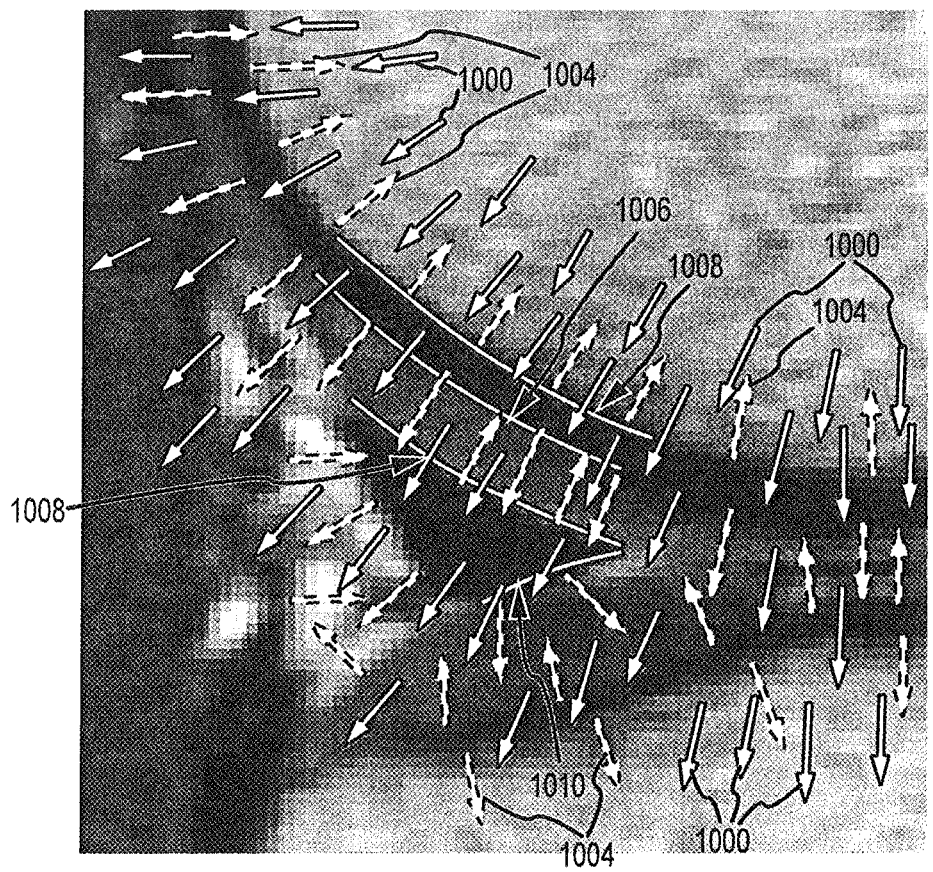
FIG. 38D is the same view as FIG. 38C, except the vectors of FIGS. 38B and 38C are superimposed.

As can be understood from FIG. 38D, the gradient of the signed distance vectors 1000 are uniformly oriented orthogonal to the bone surface and go from inside to outside of the bone. The image gradient vectors 1004 are oriented differently near different image details. For the points in the bone outer boundary 1006, the vectors 1004 are almost parallel to the vectors 1000. For two of the other boundaries 1008, the vectors 1000, 1004 are generally oppositely oriented. Finally, for the last boundary 1010, the vectors 1000, 1004 are quite differently oriented from each other. As a result of the combination of the vectors 1000, 1004 and an analysis of their directional relationships to each other, the edges image will be for FIG. 38D as follows. For points associated with the bone contour line 1006, the edges image will reflect the length of the image gradient vector. For points associated with contour lines 1008, the edges image will be zero. For points associated with the contour line 1010, the edges image values will be smaller than the length of the image gradient vector associated with the bone contour line 1006. Thus, the edges image will tend to have the largest values for the points of the bone contour line 1006.

The high values correspondent to a cartilage/fluid boundary might negatively impact operation 770e of the registration in FIG. 37. Consequently, it may be desirable to suppress those values. This can be done in the beginning of operation 770d3 of FIG. 38A. Specifically, a windowing filter may be applied to the whole target image. A window [w0, w1] may be used, where w0 will be the minimum value in the image, and w1 will be approximately the value correspondent to the cartilage intensity. The filter will replace the high intensity values in the image with w1 value, and thus the boundary between the cartilage and the lighter matters will disappear. For the type of MRI images that may be used, the w1 value correspondent to the median of all the values in the image works quite well. Although such a filter may not always suppress the cartilage boundary entirely, it makes cartilage outer boundary very much weaker in the image and, as a result, the cartilage has less of an impact in operation 770e of FIG. 37.

In one embodiment, a more sophisticated method for suppressing the cartilage boundary may be employed. The cartilage intensity values may be estimated by comparing the voxel values near landmarks 777 along the signed distance gradient direction. The values before a landmark correspond to the cortical bone intensities, while the values after the landmark correspond to the cartilage intensity. Thus for every landmark, a value may be found that represents an "Out of cortical bone" intensity. Such values may be interpolated into the whole image and this windowing function may be applied rather than the constant windowing value w1.

It should be appreciated that a lesser resolution than the target image resolution may be used in all the images participating in the edges image computation. For example, an in-slice voxel size of 1 mm may be used rather than ~0.3 mm in the target image. Using coarser resolution in effect smoothes out the data, allowing a more stable edges computation. It also significantly speeds up the computation. In case of very noisy target images, an additional smoothing step may be applied.

Operation 770 of FIG. 36 is completed via operation 770e of FIG. 37, wherein the full or entire golden femur mesh 626, including its regions 628, 629, are simultaneously registered to landmarks 777 and image edges respectively using B-spline deformable transforms. Specifically, operation 770e of FIG. 37 further refines the image registration of the boundary golden femur region. In one embodiment, a spline transformation may be used to register the open golden femur mesh 626 into the MRI scan data (target image space). In one embodiment, 3D B-Spline deformable transforms may be employed.

A B-Spline deformable transformation typically is a free form deformation of an object using a deformation field where a deformation vector is assigned to every point in space. For example, a 3D B-spline deformable transform T may specify a 3D vector V(P) for every point P in the original 3D space that is moved by T such that T:P→P+V (P).

In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of vectors may be modeled using B-splines. Typically a grid J×K×L of control points may be specified where J, K, and L are parameters of the transformation.

In one embodiment, splines of order three may be used with a grid 27×9×11 of control points. That is, the transformation employs 27 control points in the medial/lateral direction (i.e., the x direction), 9 control points in posterior/anterior direction, and 11 control points in distal/proximal direction. Two control points in each dimension (i.e., 2 of 27 in the x direction, 2 of 9 in the y direction and 2 of 11 in the z direction) may be used to specify boundary conditions. As such, the inner spline nodes may form a grid of size 25 by 7 by 9 and the boundary conditions increase the grid to size 27 by 9 by 11. The parametric set for this transformation has a dimension of 3×27×9×11=8019 (i.e., at each node of a 27×9×11 grid of control points, there is specified a 3-dimensional transformation vector; a nonlinear interpolation of transformation vectors for points located between adjacent nodes, is governed by spline equations.) The final parameters of the spline transformation that minimizes the misalignment between the reference golden femur template and the target MRI scan data may be found.

In operation 770e of FIG. 37 a different metric (or defect function) may be used as compared to what was used in operations 770a, 770b, and 770c. Specifically, a combined defect function may be used. The combined defect function may be defined as a linear combination of the defect function D (same as in operations 770a, 770b, and 770c) and defect functions D_i that evaluate the discrepancy between the golden mesh regions 628, 629 and the scan image edges defined in operation 770d of FIG. 37.

The defect function D_i, or rather its opposite metric function M_i=−D_i, for a given Golden Mesh Region R_i may be defined as follows. All the vertices in the golden mesh region R_i, are taken, a transform is applied to them, and the correspondent intensities are evaluated in the edges image. M_i may be set to be the sum of those intensities. Thus, when more vertices from the transformed golden mesh region R_i come close to the image edges, a higher metric value is the result.

When defining the combined metric or defect, that is when taking the linear combination of D and all the D_i, the coefficients in the linear combination need to be specified. It may be desirable to use a very high coefficient with D because we want to follow very precisely the landmarks 777 provided by a user. Smaller coefficients may be employed with D_i. The latter coefficients might be also different. The higher coefficients may be used for those regions of the bone that require a greater degree of precision, the associated image segmentation needing to result in more clearly defined regions. The lower coefficients may be used for those regions of the bone that do not require a high degree of precision, the associated image segmentation resulting in less clearly defined regions.

Some bones may have a higher degree of shape variations across the population than is found with the knee region of the femur. For example, the shape of the tibia may vary more from patient to patient than does the shape of the femur. As a result, the affine transformation may not provide a close enough registration of the golden tibia template to the target tibia in the target scan. This may cause the Spline transformation to find a local optimum that may be far from the actual tibia in some areas. In one embodiment, an additional registration operation between the affine transform and spline transform operations may be performed to more closely align the golden tibia and the target tibia, allowing the spline transform to converge to the correct local optimum rather than a nearby, but wrong, local optimum.

The class of transforms utilized generally should allow more flexibility (or degrees of freedom) than the Affine transform and less flexibility than the B-spline transforms. The number of degrees of freedom generally is equal to the number of transform parameters. In one embodiment, a class of transforms with more than 12 parameters and less than 3×27×9×11 parameters may be used. For example, a B-spline transform with fewer control points than used in the subsequent spline transform may be used for the additional transform operation. Alternatively, the deformations may be modeled using quadric rather than cubic functions.

In another embodiment, several golden tibia templates may be used that represent typical tibia variations, e.g., golden tibia templates for varus, valgus, and normal tibia. In one embodiment, each of the golden tibia templates may be used during the translation, similarity and affine transform registration operations to find the template that provides the best match (e.g., best correlation) in the affine transform registration operation. This template may then be used in the remaining registration operations.

Finally, in one embodiment, the tibia registration may be improved by performing the tibia segmentation after the femur segmentation and adding a restriction on the tibia registration transformations such that the tibia may not penetrate the femur. In one embodiment, this may be implemented by introducing a penalty for the penetration. In the target MRI all the voxels that lie inside the femur segmentation curves may be marked. The metric functions, described in more detail below, that are used in the registration operations may be modified to include a penalty term. The penalty term may be computed by taking points in the golden tibia mesh, applying a transform to the set of points, determining if a transformed sample point falls into any of the marked voxels, and adding a large value to the penalty term for each transformed sample point that falls into any of the marked voxels.

In each of the above registration operations, a metric may be used to quantify the degree of correspondence between the reference objects and target image achieved by a given transformation. In one embodiment, the metric quantitatively measures how well the transformed golden femur data fits the target image (e.g., a target MRI scan) and landmarks positioned there.

As discussed above, metrics M=−D, M_i=−D_i, and their linear combination are used in operations 770a-770d of the registration. An explanation is now given regarding the details on how to compute those metrics. As far as using those metrics with optimizers that require computations of the gradient of the metric, it is also explained how to compute the gradient of those metrics.

When computing the metric M or rather the defect D, such a computation can include finding the sum of the squared distances from each landmark point 777 to the transformed open golden mesh. In order to make this computation as quickly and efficiently as possible, the following can be done. First, a B-Spline transformation of a mesh is no longer a mesh. The plane triangles forming the original mesh get curved over the transformation, and the triangles are no longer planar. Rather than computing distances to curved triangles, which would be very computationally expensive, planar triangles connecting the transformed vertices are used. Very little precision is lost with this substitution because the triangles are very small.

Next, after finding the transformed mesh, it is desirable for every Landmark point to find the closest point in the transformed mesh triangles and take the squared distance to it. A spatial subdivision scheme is used to sort all the triangles by spatial location. An octree subdivision is used, although other schemes (kd-tree, fixed size grid, etc.) would work as well. The spatial subdivision helps to find a closest mesh triangle and a closest point in it using an order of LOG(n) operations where n is the number of triangles in the mesh.

The optimizers used in the registration steps require the computation of the gradient of the metric function, which depends on the applied transform, over the transform parameters.

In one embodiment the metric function may be a composition of several functions. For the metric M (or cost function D), for example, the following functions are used in the composition: a) mesh transformation, b) distance from a Landmark point to the transformed mesh, c) squared distance, d) sum of squares, e) inverse of the sum.

For a composition of functions, determining the gradient involves finding partial derivatives for each function and then applying the chain rule. The derivatives of the algebraic functions are computed by standard formulae. The only non-trivial computation in the above functions is the computation of the partial derivative of a distance from a point to the transformed mesh.

For the latter computation, it may involve using an approximate method. Namely, take the closest triangle found in the metric computation followed by taking the plane containing that triangle. This plane approximates the transformed mesh surface in some small neighborhood of the closest point. One of the transform parameters is changed by a very small amount. It is observed where the former closest triangle is mapped after the variation.

The plane containing the varied triangle is taken. This plane approximates the varied transformed mesh surface in some small neighborhood of the varied closest point. The distance from the landmark point to this varied plane is taken. It is approximately the distance from the landmark point to the whole varied transformed mesh surface. Now the difference between the varied distance and the original distance is taken and divided by the value of the parameters variation. This gives approximately the partial derivative for this parameter.

In order to compute the gradient of the metric D_i with respect to the transform parameters, the gradient image of the edges image is computed right after the computation of the edges image itself. To compute the partial derivative of D_i over a transform parameter, the computation may take place for the derivative of every transformed vertex motion over that parameter using the chain rule. This derivative will be a 3D vector. Its dot product is taken with the correspondent Gradient vector of the Gradient Image of the Edges Image and the values are summed all over the vertices.

Finally, since the combined defect function is a linear combination of defect functions D and D_i, then the gradient of the combined defect function with respect to a given transform, is correspondingly a linear combination (with the same coefficients) of the gradients of D and D_i with respect to that same transform.

In summary and as can be understood from the immediately preceding discussion regarding operations 770a-770c and 770e of FIG. 37, translation transforms (operation 770a), similarity transforms (operation 770b), affine transforms (operation 770c), and B-Spline deformable transforms (operation 770e) are employed as part of accomplishing operation 770 of FIG. 36. Because in operations 770a-770c of FIG. 37 it is intended to register the open golden femur mesh to landmarks, the metric (or defect) function should evaluate how close the transformed open golden femur mesh is to landmarks. Thus, in operations 770a-770c, there is a selection of the defect function D to be the sum of squared distances from landmarks to the deformed open golden mesh. In the operation 770e, a simultaneous registering of several parameters may be defined as a combined metric that will take into account all the parameters. The combined defect function may be defined as a linear combination of the defect function D (same as in operations 770a-770c) and defect functions D_i that evaluate the discrepancy between the golden mesh regions and the scan image edges defined in operation 770d of FIG. 37.

Once operation 770 of FIG. 36 is completed, the process of FIG. 36 then continues with operation 772, wherein the deformed open golden femur mesh 626 and associated regions 628, 629 are segmented followed by operation 773, wherein the resulting segmentation curves are approximated with splines. The process continues with operation 774, wherein the contour lines or splines generated in operation 773 are modified to match landmarks.

In other words, in operation 774 the segmentation curves are refined to more precisely match the landmarks. Typically, the segmentation curves created via the above-described algorithms match the landmarks quite closely. Accordingly, most any simple algorithm for a local curve adjustment can work to further refine the precision of the match of the segmentation curves with the landmarks.

In one embodiment of operation 774 when further refining the segmentation curves to match landmarks, only those curves that belong to slices that contain landmarks are considered. When a curve belongs to a slice with landmarks, it is assumed that it should rather precisely go through all the Landmarks. In one embodiment, a curve may be considered to be precisely enough located relative to a landmark if its distance from the landmark ("Tol") is Tol=0.3 mm or less. Most often all the landmarks are within the Tol distance from the curve. However, sometimes a few of the landmarks are further than the Tol distance from the curve. As can be understood from the following discussion regarding operation 774, for every curve generated via the above-described algorithms, each landmark in a slice is iterated. If a landmark is not within Tol distance from the curve, a correction algorithm is applied to the curve as described below with respect to operation 774.

Operation 774 locally modifies the spline curve to fit a selected landmark. Specifically, as can be understood from FIG. 39, which is a flowchart illustrating the process of operation 774 of FIG. 36 in the context of a particular image slice containing landmarks and a segmentation contour, in operation 774a a landmark 777 is identified. In operation 774b, the distance of the identified landmark 777 to the spline generated from the golden femur mesh 626 is computed. More specifically, the algorithm of operation 774 first computes distances for all the other landmarks in the same slice to avoid making the distance relationships of the landmarks and curve worse.

In operation 774c, an arc of the contour line or spline that is the closest to the landmark is identified. Specifically, the closest spline arc [A, B] to the selected landmark L is located, where A and B are consecutive vertices in the spline curve.

In operation 774d, the arc is modified to include the identified landmark, resulting in a modified contour line or spline. Specifically, the vertices A and B are moved iteratively so that the arc [A, B] fits L. For each iteration, the closest point C in [A, B] to L is found. The ratio $\alpha$: $(1-\alpha)$ is then found in which C divides [A, B]. Next, A is moved by $(1-\alpha)*(L-C)$, and B is moved by $\alpha*(L-C)$. The process stops when 0.5*Tol distance is achieved.

Figure 39:
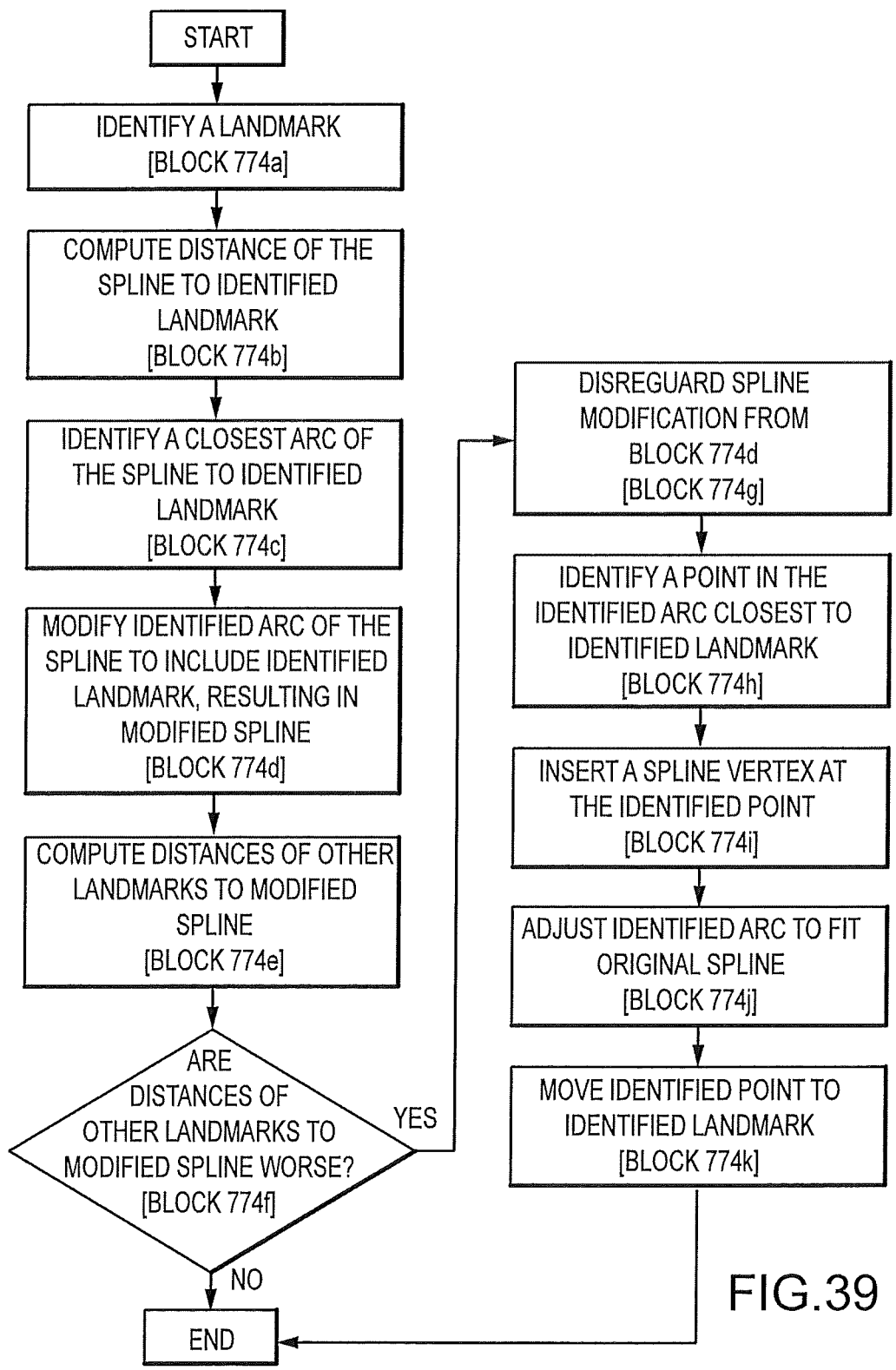
FIG. 39 is a flowchart illustrating the process of operation "Modify Splines" of FIG. 36.

In operation 774e, distances of other landmarks to the modified spline are computed and reviewed in operation 774*f* to verify operations 774*a*-774*d* have not made the fit between the spline and other landmarks worse. In other words, the following is checked for every landmark. First, it is checked to see if the new distance between the spline and landmark is within Tol and, if it is, then the relationship between the spline and landmark is acceptable. Second, it is checked to see if the new distance between the spline and landmark is smaller than the old distance and, if it is, then the relationship between the spline and landmark is acceptable. Third, it is checked to see if the new distance is higher than Tol, the old distance was higher than Tol, and the new distance increased by less than 0.5*Tol. If the answer is yes with respect to all three of the elements of the third check, then the relationship between the spline and landmark is acceptable. For all the other cases, the relationship between the spline and landmark is not acceptable. If the distance relationships between the spline and all of the landmarks are considered acceptable, the process outlined in FIG. 39 is completed for the identified landmark, and the process of FIG. 39 can then be run for another identified landmark until all landmarks have gone through the process of FIG. 39.

If any of the distance relationships between any landmark and the spline are found to be unacceptable in operation 774*f* due to a modification of the spline with respect to a selected landmark according to operations 774*a*-774*d*, then per operation 774*g* the spline modification from operation 774*d* is disregarded and a more local modification is employed, as described below with respect to operations 774*h*-774*k* of FIG. 39. The more local modification will add a new vertex into the spline making the spline more flexible in this region. The more local modification will then move the new vertex to L, and this will affect a very small area of the spline. Thus, the chance of decreasing the fit to other landmarks will be very small. The more local modification occurs as follows.

In operation 774*h*, a point in the identified arc closest to the identified landmark is identified. Specifically, the point C in arc [A, B] that is the closest to landmark L is found.

In operation 774*i*, a spline vertex is inserted at the identified point C. With the insertion of a new vertex, the spline shape usually changes in the two immediately adjacent neighbor arcs on both sides of the arc [A, B]. As a result, the arc spline can become too wavy in the vicinity of the arc [A, B].

To remedy the situation, the arc [A, B] is adjusted to fit the original spline in operation 774*j*. Specifically, the vertices A and B are modified to try to fit the new spline as closely as possible to the original spline. In doing so, a measure of closeness (i.e., how closely the new spline follows the original spline in the six neighboring arcs—three to each side of the new control point C) may be computed as follows. In one embodiment, the six spline arcs are sampled such that there are twenty or so sample points in every arc of the spline (i.e., 20*6 sample points). Then, the sum of the squared distances from the sample points to the original spline may be computed. Next, the coordinates of th\e A and B vertices (control points) are varied (i.e., two parameters for each of A and B, that is four parameters). Then, a local optimization algorithm is used to find the closest spline. This process may be similar to the process of fitting a spline to a polyline, as described elsewhere in this Detailed Description.

Per operation 774*k*, the identified point is moved to the identified landmark. Specifically, the spline vertex C is moved into the landmark point L.

The process outlined in FIG. 39 is completed for the identified landmark, and the process of FIG. 39 can then be run for another identified landmark until all landmarks have gone through the process of FIG. 39.

Once the process of FIG. 39 is completed for all landmarks and the associated contour lines or splines, the process of operation 774 of FIG. 36 is considered complete, which completes the process of FIG. 36 for the operation 252*a* of FIG. 33. The process of operation 252*a* in FIG. 33 is now complete. The image slices 16 are then scrolled over to verify if the segmentation results are acceptable, as indicated by operation 252*c*. In operation 253, if the segmentation is acceptable, then the segmentation process of FIG. 33 ends.

As can be understood from FIG. 33, if in operation 253 the segmentation is not acceptable, then the segmentation of each offending slice 16 is modified by adding additional landmarks 777 and/or modifying the locations of existing landmarks 777 per operation 254 of FIG. 33. For example and as can be understood from FIG. 40, a first spline 800, which is generated via a first run through operation 252 of FIG. 33, has control points 802 and extends along first landmarks 777*a* placed in the slice 16 of FIG. 40 during operation 251 of FIG. 33.

Figure 40:
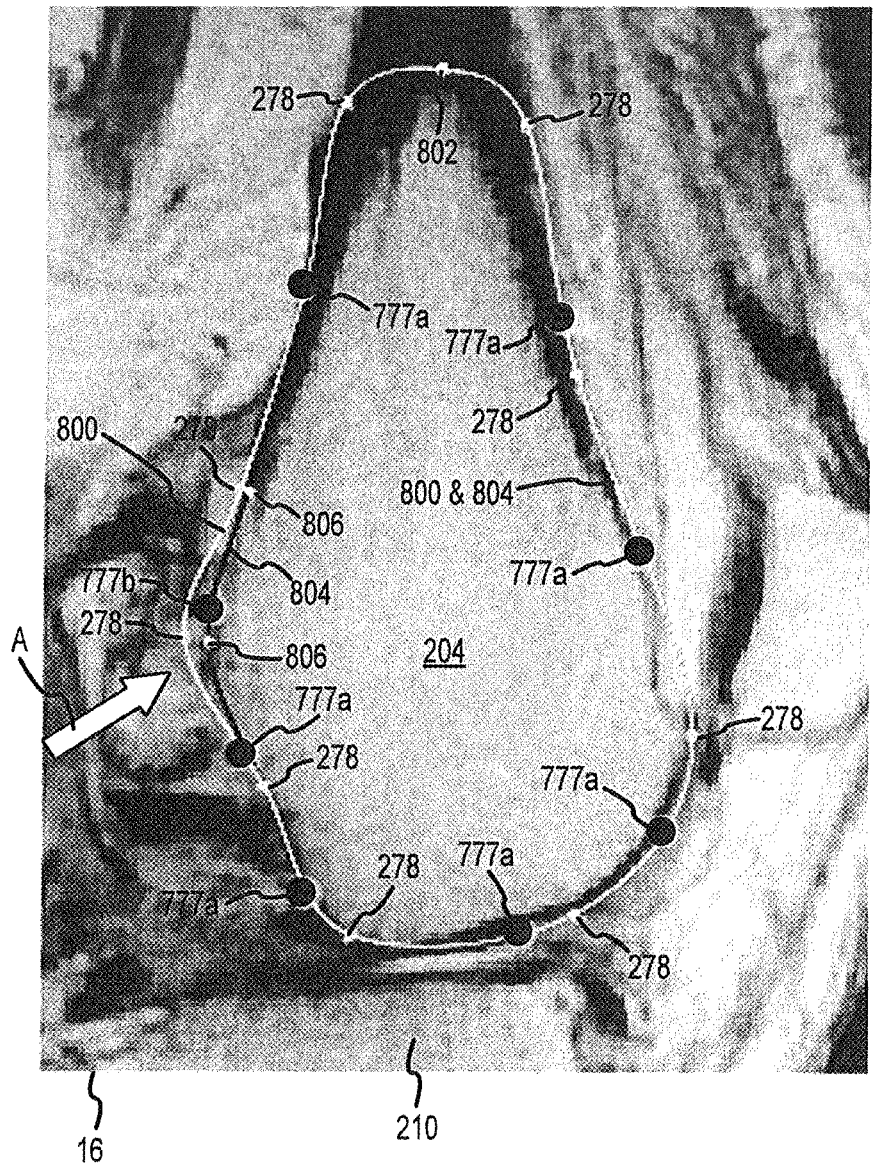
FIG. 40 is an image slice with a spline being modified according to the operations of the flow chart of FIG. 39.

During operation 253 of FIG. 33 the segmentation of the slice 16 of FIG. 40 is identified as being unsatisfactory in the location called out by arrow A in FIG. 40. A new landmark 777*b* is added in the location called out by arrow A per operation 254 and operation 252, or more specifically, operations 774*b*-774*e* of the algorithm of FIG. 39, are repeated to generate a second spline 804, which has control points 806 and extends along both the first landmarks 777*a* and the second landmark 777*b*. As can be understood from FIG. 40, the first spline 800 and the second spline 804 are generally identical and coextensive, except in the region identified by arrow A. The segmentation of the second spline 804 is then approved or disapproved per operation 253. If approved, then the segmentation process of FIG. 33 ends. If disapproved, then the second spline 804 is further modified per operation 254 in a manner similar to as discussed above with respect to FIG. 40.

In one embodiment of operation 254 of FIG. 33, the spline may be simultaneously modified near a new added landmark or near moving landmarks to fit the moving landmarks. In doing so, it may be the case that the user is satisfied with the corrected splines. As a result, the process of FIG. 33 may simply end at operation 254 as if the entirety of operation 252 had been completed and the segmentation was found acceptable at operation 253.

In one embodiment, when a user adds a new landmark into a slice with a spline, the spline is immediately modified using precisely the same algorithm of FIG. 39, namely operations 774*b*-774*e*. When a user moves a landmark, the spline is updated during the motion using operations 774*b*-774*e* of the algorithm of FIG. 39. Adding landmarks (operations 774*g*-774*k* of the algorithm of FIG. 39) is avoided during the motion phase as it may lead to multiple updates during motions, resulting in too many points.

Once the contour lines or splines are successfully segmented from each target image slice, the contour lines or splines are compiled as discussed above into a 3D mesh that may be used as an arthritic bone model 36 (see FIG. 1D) or bone models 22 (see FIG. 1C).

In one embodiment of the registration process discussed above, an optimizer may be used during the registration process to maximize similarity between the open golden mesh and landmarks in the target image (and possibly edges image) by adjusting the parameters of a given transformation model to adjust the location of reference image coordinates in the target image. In one embodiment, the optimizer for a registration operation may use the transformed golden femur data from the previous registration operation as its initial approximation. Then, local optimization techniques may be used to search for a local optimum near the initial starting approximation. This may be done so that any potential matches farther away from the feature of interest (e.g., the femur or tibia in a knee joint) reliably found in an earlier operation may be eliminated.

In operation 770a of FIG. 37, when optimizing the translation transformation, a regular step gradient descent optimizer may be used by one embodiment. Other embodiments may use different optimization techniques.

To find a local minimum, parameter steps may be taken in the direction of the negative of the metric gradient (or the approximate gradient) over the transform parameter space at the current point. This generally optimizes the metric which typically has a local minimum when features of the reference image mapped into corresponding features of the target image have minimal misalignment).

In one embodiment, initial gradient step of 3 millimeters may be specified, a relaxation factor may be set to 0.95 and a maximum of 50 iterations may be used in the regular step gradient descent optimization method to determine the parameters of the translation transformation that results in minimal misalignment between the reference Open Golden Femur mesh and the Landmarks in the target MRI scan.

In operation 770b of FIG. 37, when optimizing the similarity transformation, a regular step gradient descent optimizer may be used again by one embodiment. When applying the regular step gradient descent optimizer to similarity transformation, the result and the convergence rate depend on the proper choice of parameters representing the similarity transforms. A good choice of parameters when used with gradient computations is such that a variation of every parameter by one unit leads to approximately equal displacement of object points. In order to ensure similar displacement of points with respect to three rotational parameters in the similarity transform, the initial center of rotation for the similarity transformation may be specified as the center of a bounding box (or minimum sized cuboid with sides parallel to the coordinate planes) that encloses the feature (e.g., a bone) registered in the translation registration (e.g., operation 770a in FIG. 37). For knee segmentation, scaling coefficients of approximately 40-millimeters may be used for the scaling parameters when bringing the rotational angle parameters together with translation parameters. A scaling coefficient of approximately 40-millimeters may be used because it is approximately half the size of the bone (in the anterior/posterior and medial/lateral directions) of interest and results in a point being moved approximately 40-millimeters when performing a rotation of one radian angle. By the same reason a scaling coefficient of 40 millimeters may be used in the similarity transform scaling parameter together with its translational parameters.

In one embodiment, an initial gradient step of 1.5 millimeters may be specified, a relaxation factor may be set to 0.95 and a maximum of 50 iterations may be performed in the regular step gradient descent optimization method to determine the parameters of the similarity transformation that results in minimal misalignment between the reference open golden template mesh and landmarks in the target MRI scan.

In operation 770c of FIG. 37, when optimizing the affine transformation, a regular step gradient optimizer may be used again by one embodiment. For knee bones, scaling coefficients of approximately 40 millimeters may be used for the matrix coefficients variations when bringing them together with translation parameters. An initial gradient step of 1 millimeter may be specified, the relaxation factor may be set to 0.95 and a maximum of 50 iterations may be performed to determine the parameters of the affine transformation that results in minimal misalignment.

In operation 770e of FIG. 37, when optimizing the B-spline transformation, a modified regular step gradient descent optimizer may be used by one embodiment when searching for the best B-spline deformable transformation. Namely, a combination of regular step gradient descent optimizer with by coordinate descent may be used here. Rather than computing one gradient vector for the transform space and taking a step along it, a separate gradient may be computed for every B-spline transform node. In one embodiment, order three B-splines (with J×K×L control nodes) may be used and J×K×L gradients may be computed, one for each control point. At every iteration, each of the spline nodes may be moved along its respective gradient. This may enable faster convergence of the optimization scheme. A relaxation factor of 0.95 may be used for each spline node. A an initial gradient step of one-millimeter may be set for every B-spline grid node, and a maximum of 50 iterations may be used in the regular step gradient descent optimization method to find the parameters of the B-spline transformation that provides minimal misalignment of the open golden femur mesh and landmarks and feature edges in the target MRI scan.

FIG. 23 depicts a flowchart illustrating one method for generating spline curves outlining the surface of an object of interest in each target MRI slice (e.g., as discussed above with respect to operation 772 of FIG. 36) after the transformed golden femur mesh is found in operation 770e in FIG. 37. Initially, operation 470 intersects the transformed golden femur mesh with a slice of the target scan data. The intersection defines a polyline curve of the surface of the feature (e.g., bone) in each slice. Two or more polyline curves may be generated in a slice when the bone is not very straightly positioned with respect to the slice direction.

A polyline curve is a piecewise linear approximation to a curved feature shape. Generally, this curve should be easy to manipulate with a set of control points. The polyline curve may have many segments, making it more difficult to manipulate the polyline curve (e.g., during operation 254 or 260 of FIG. 6). One embodiment may generate one or more Kochanek splines from the polyline curve. Each spline typically has a smaller number of control points and typically fits the polyline curve with about 0.3-millimeter deviation. See section b. of this Detailed Description for a detailed discussion regarding spline generation.

As discussed above, in one embodiment, the output of the segmentation may be a triangular mesh (e.g., a 3D surface model) of the segmented bone(s) of a joint (e.g., the femur and tibia of a knee joint). The mesh generated generally represents a watertight surface that closely follows the segmentation contour curves of the slices, smoothly interpolates between the segmentation contour curves, and may have a low triangular count. See section b. of this Detailed Description for a detailed discussion regarding mesh generation and the manual adjustment of segmentation splines.

The 3D surface models of the lower end of the femur and the upper end of the tibia of a patient's knee may be used to create arthroplasty jigs and/or implants. For example, the models may be used to create femur and tibia jigs that can be used with a patient's femur and tibia as disclosed in the various U.S. Patent Applications incorporated by reference herein in this Detailed Description and filed by Park and Park et al. The automatic or semi-automatic processes described herein for segmentation of image data to generate 3D bone models may reduce the overall time required to perform a reconstructive surgery to repair a dysfunctional joint and may also provide improved patient outcomes.

Although the present invention has been described with respect to particular embodiments, it should be understood that changes to the described embodiments and/or methods may be made yet still embraced by alternative embodiments of the invention. For example, certain embodiments may operate in conjunction with a MRI or a CT medical imaging system. Yet other embodiments may omit or add operations to the methods and processes disclosed herein. Accordingly, the proper scope of the present invention is defined by the claims herein.

What is claimed is:

1. A method for pre-operative planning for an arthroplasty procedure for a patient bone in an arthroplasty target area, the method comprising:
receiving scan data associated with the patient bone corresponding to the arthroplasty target area, the scan data captured using a medical scanning system;
generating a model of the patient bone from a golden template that has been modified using the scan data, the golden template being associated with an exemplary bone;
generating preoperative planning data from the model, the preoperative planning data corresponding to an arthroplasty implant to repair at least a portion of a joint associated with the patient bone; and
generating a treatment based on the preoperative planning data, the treatment including a bone resectioning plan for the arthroplasty target area to prepare the arthroplasty target area based on the arthroplasty implant.

2. The method of claim 1, wherein the scan data includes image slices of the patient bone.

3. The method of claim 1, wherein the model of the patient bone is generated based on landmarks associated with the patient bone in the scan data.

4. The method of claim 1, wherein the exemplary bone is a bone type that is the same as the patient bone and is representative of what is considered to be non-diseased and non-damaged with respect to the bone type.

5. The method of claim 1, wherein the golden template is modified by mapping the golden template to the scan data.

6. The method of claim 1, wherein the model is modified to represent a non-diseased state of the patient bone.

7. The method of claim 1, wherein the bone resectioning plan includes at least one of cutting, drilling, reaming, or resurfacing the arthroplasty target area.

8. The method of claim 1, wherein one or more machines are guided with a computer based on the bone resectioning plan.

9. A method for pre-operative planning for an arthroplasty procedure for a patient bone in an arthroplasty target area, the method comprising:
receiving scan data associated with the patient bone corresponding to the arthroplasty target area, the scan data captured using a medical scanning system;
identifying one or more landmarks in the scan data;
obtaining golden bone data associated with an exemplary bone;
generating a patient model of at least a portion of the patient bone by modifying the golden bone data using the one or more landmarks in the scan data;
generating a non-diseased state of the patient model; and
generating preoperative planning data from the non-diseased state of the patient model, the preoperative planning data corresponding to an arthroplasty implant to repair at least a portion of a joint associated with the patient bone.

10. The method of claim 9, wherein the repair includes restoring the joint to at least one of natural alignment or zero mechanical axis alignment.

11. The method of claim 9, wherein the scan data includes image slices of the patient bone.

12. The method of claim 9, wherein the golden bone data includes a model of the exemplary bone.

13. The method of claim 9, wherein the golden bone data is modified by mapping the golden bone data to the scan data using the one or more landmarks.

14. The method of claim 9, wherein bone resection planning data is generated based on the preoperative planning data and specifying a treatment to prepare the arthroplasty target area for the arthroplasty implant.

15. A method for pre-operative planning for an arthroplasty procedure for a patient bone in an arthroplasty target area, the method comprising:
receiving scan data associated with the patient bone corresponding to the arthroplasty target area, the scan data captured using a medical scanning system;
generating a patient model of at least a portion of the patient bone from golden bone data that has been modified by mapping the golden bone data to the scan data using one or more landmarks, the golden bone data being associated with an exemplary bone, the patient model corresponding to a non-diseased state of the patient bone; and
generating preoperative planning data from the patient model, the preoperative planning data corresponding to an arthroplasty implant to repair at least a portion of a joint associated with the patient bone.

16. The method of claim 15, wherein the golden bone data includes a model of the exemplary bone.

17. The method of claim 15, wherein the patient model is generated using one or more curves modified to match the one or more landmarks.

18. The method of claim 17, wherein the one or more curves are generated from a golden bone mesh of the golden bone data, the golden bone mesh being deformed to match the one or more landmarks.

19. The method of claim 15, wherein bone resection planning data is generated based on the preoperative planning data and specifying a treatment to prepare the arthroplasty target area for the arthroplasty implant.

20. The method of claim 19, wherein one or more machines are guided with a computer based on the bone resectioning planning data.

* * * * *